US011825838B2

(12) United States Patent
Harschneck et al.

(10) Patent No.: US 11,825,838 B2
(45) Date of Patent: Nov. 28, 2023

(54) TRICYCLIC CARBOXAMIDES FOR CONTROLLING ARTHROPODS

(71) Applicant: Bayer CropScience Aktiengesellschaft, Monheim am Rhein (DE)

(72) Inventors: Tobias Harschneck, Duesseldorf (DE); Alexander Arlt, Cologne (DE); Robert Velten, Langenfeld (DE); Michael Maue, Langenfeld (DE); Kerstin Ilg, Cologne (DE); Werner Hallenbach, Monheim (DE); Ulrich Goergens, Ratingen (DE); Sebastian Horstmann, Leverkusen (DE); Peter Loesel, Leverkusen (DE); Andreas Turberg, Haan (DE)

(73) Assignee: Bayer CropScience Aktiengesellschaft, Monheim am Rhein (DE)

( * ) Notice: Subject to any disclaimer, the term of this patent is extended or adjusted under 35 U.S.C. 154(b) by 227 days.

(21) Appl. No.: 16/498,674

(22) PCT Filed: Mar. 26, 2018

(86) PCT No.: PCT/EP2018/057614
§ 371 (c)(1),
(2) Date: Sep. 27, 2019

(87) PCT Pub. No.: WO2018/177995
PCT Pub. Date: Oct. 4, 2018

(65) Prior Publication Data
US 2021/0106005 A1  Apr. 15, 2021

(30) Foreign Application Priority Data
Mar. 31, 2017  (EP) .................... 17164442

(51) Int. Cl.
*C07D 417/04* (2006.01)
*C07D 409/04* (2006.01)
*C07D 403/04* (2006.01)
*A01N 43/56* (2006.01)
*A01N 43/78* (2006.01)
*A01N 33/26* (2006.01)

(52) U.S. Cl.
CPC ............ *A01N 33/26* (2013.01); *A01N 43/56* (2013.01); *A01N 43/78* (2013.01); *C07D 403/04* (2013.01); *C07D 409/04* (2013.01); *C07D 417/04* (2013.01)

(58) Field of Classification Search
None
See application file for complete search history.

(56) References Cited

U.S. PATENT DOCUMENTS

| 8,685,964 | B2 | 4/2014 | Bretschneider et al. |
| 8,686,004 | B2 | 4/2014 | Bretschneider et al. |
| 8,946,234 | B2 | 2/2015 | Maue et al. |
| 9,044,015 | B2 | 6/2015 | Bretschneider et al. |
| 9,066,518 | B2 | 6/2015 | Bretschneider et al. |
| 9,643,953 | B2 | 5/2017 | Hitchcock et al. |
| 10,208,015 | B2 | 2/2019 | Hallenbach et al. |
| 10,357,036 | B2 | 7/2019 | Harschneck et al. |
| 2011/0166143 | A1 | 7/2011 | Bretschneider et al. |
| 2011/0301181 | A1 | 12/2011 | Maue et al. |
| 2012/0165345 | A1 | 6/2012 | Bretschneider et al. |
| 2014/0148471 | A1 | 5/2014 | Bretschneider et al. |
| 2014/0221362 | A1 | 8/2014 | Bretschneider et al. |
| 2014/0315934 | A1 | 10/2014 | Hitchcock et al. |
| 2015/0099766 | A1 | 4/2015 | Maue et al. |
| 2017/0144988 | A1 | 5/2017 | Hallenbach et al. |
| 2018/0289007 | A1 | 10/2018 | Harschneck et al. |
| 2019/0047982 | A1 | 2/2019 | Jansen et al. |

FOREIGN PATENT DOCUMENTS

| CN | 101337940 A | 1/2009 |
| CN | 102060818 A | 5/2011 |
| CN | 103232431 A | 8/2013 |
| EP | 1911751 A1 | 4/2008 |
| EP | 2594555 A1 | 5/2013 |
| JP | 2010513403 A | 4/2010 |
| JP | 2010508274 A | 10/2012 |
| JP | 2013534530 A | 9/2013 |
| WO | 0007980 A1 | 2/2000 |
| WO | 2004018439 A1 | 3/2004 |
| WO | 2005085216 A1 | 9/2005 |
| WO | 2006043635 A1 | 4/2006 |
| WO | 2008054702 A1 | 5/2008 |
| WO | 2008074835 A1 | 6/2008 |
| WO | 2008098105 A1 | 8/2008 |
| WO | 2008134969 A1 | 11/2008 |
| WO | 2009049851 A1 | 4/2009 |

(Continued)

OTHER PUBLICATIONS

European Search Report for EP 17164442.0, dated Sep. 4, 2017.
European Search Report for EP 17164442.0, dated May 24, 2017.
International Search Report for PCT/EP2018/057614, dated Jul. 30, 2018.
Yang, et al., "Mild and General Conditions for Negishi Cross-Coupling Enabled by the Use of Palladacycle Precatalysts," Angew. Chem. Int. Ed., (2013), vol. 52: 615-619.
Just-Baringo, et al., "Total Synthesis and Stereochemical Assignment of Baringolin," Angew. Chem. Int. Ed., (2013), vol. 52: 7818-7821.

(Continued)

*Primary Examiner* — John Pak
(74) *Attorney, Agent, or Firm* — MCBEE MOORE & VANIK IP, LLC

(57) ABSTRACT

The invention relates, inter alia, to compounds of general formula (I). The invention also relates to methods for synthesizing the compounds of formula (I). The compounds according to the invention are in particular suitable for controlling insects, arachnids and nematodes in agricultural applications and for controlling ectoparasites in veterinary medicine.

19 Claims, No Drawings

(56) References Cited

FOREIGN PATENT DOCUMENTS

| WO | 2009080250 | A2 | 7/2009 | | |
|---|---|---|---|---|---|
| WO | 2009099929 | A1 | 8/2009 | | |
| WO | 2009106441 | A1 | 9/2009 | | |
| WO | 2009112845 | A1 | 9/2009 | | |
| WO | 2010051926 | A2 | 5/2010 | | |
| WO | 2010093885 | A1 | 8/2010 | | |
| WO | 2010121675 | A2 | 10/2010 | | |
| WO | 2011045224 | A1 | 4/2011 | | |
| WO | 2011113756 | A1 | 9/2011 | | |
| WO | 2011149874 | A2 | 12/2011 | | |
| WO | 2012000896 | A2 | 1/2012 | | |
| WO | 201229672 | A1 | 3/2012 | | |
| WO | 2012033390 | A2 | 3/2012 | | |
| WO | 2012038743 | A1 | 3/2012 | | |
| WO | 2012038904 | A1 | 3/2012 | | |
| WO | 2012058176 | A1 | 5/2012 | | |
| WO | 2012069366 | A1 | 5/2012 | | |
| WO | 2012080376 | A1 | 6/2012 | | |
| WO | 2012102387 | A1 | 8/2012 | | |
| WO | 2012107434 | A1 | 8/2012 | | |
| WO | WO-2012102387 | A1 * | 8/2012 | ........... | A01N 43/653 |
| WO | 2012137181 | A1 | 10/2012 | | |
| WO | 2012175474 | A1 | 12/2012 | | |
| WO | 2013079223 | A1 | 6/2013 | | |
| WO | 2013092512 | A1 | 6/2013 | | |
| WO | 2013144213 | A1 | 10/2013 | | |
| WO | 2014114532 | A1 | 7/2014 | | |
| WO | 2014152115 | A1 | 9/2014 | | |
| WO | 2015011281 | A1 | 1/2015 | | |
| WO | 2015193218 | A1 | 12/2015 | | |
| WO | 2016008830 | A1 | 1/2016 | | |
| WO | 2016055947 | A1 | 4/2016 | | |
| WO | 2016174052 | A1 | 11/2016 | | |
| WO | 2017025590 | A1 | 2/2017 | | |
| WO | 2017137338 | A1 | 8/2017 | | |
| WO | 2017137388 | A1 | 8/2017 | | |
| WO | WO-2019030357 | A1 * | 2/2019 | ............. | A01N 25/12 |

OTHER PUBLICATIONS

Potratz, et al., "Thiophene-based donor-acceptor co-oligomers by copper-catalyzed 1,3-dipolar cycloaddition," Beilstein Journal of Organic Chemistry, (2012), vol. 8: 683-692.

Hawker, et al., "Synthesis and evaluation of novel heteroaromatic substrates of GABA aminotransferase," Bioorganic & Medical Chemistry, (2012), vol. 20: 5763-5773.

Goddard, Carl J., "Antiinflammatory 1-Phenylpyrazole-4-Heteroarylalkanoic Acids," J. Heterocyclic Chem., (Oct. 1991), vol. 28: 1607-1612.

Draber, et al., "Chemistry of the Crop Protection Compositions and Pesticides," Springer Verlag, (1970), vol. 2: 401-412.

Mikhed'Kina, et al., "Reaction of Ethyl 4-[(E)-1-Chloro-3-oxoprop-1-en-1-yl]-3,5-dimethyl-1H-pyrrole-2-carboxylate with Hydrazines," Russian Journal of Organic Chemistry, (2009), vol. 45, No. 4: 564-571.

Pin, et al., "Design of α7 nicotinic acetylcholine receptor ligands in quinuclidine, tropane and quinazoline series. Chemistry, molecular modeling, radiochemistry, in vitro and in rats evaluations of a [18F] quinuclidine derivative," European Journal of Medicinal Chemistry, (2014), vol. 82: 214-224.

Clarke, et al., "Condensed Isothiazoles. Part 5. Thieno[2,3-d]isothiazoles and Thieno[3,2-d]isothiazoles," J. Chem. Soc. Perkin 1, (1980), vol. 4: 1029-1037.

Duval, et al., "Rapid Discovery of Triazologenzylidene-Thiazolopyrimidines (TBTP) as CDC25 Phosphatase Inhibitors by Parallel Click Chemistry and in Situ Screening," J. Comb. Chem., (2009), vol. 11: 947-950.

Xia, et al., "A Novel Bitriazolyl Acyclonucleoside Endowed with Dual Antiproliferative and Immunomodulatory Activity," Journal of Medicinal Chemistry, (2012), vol. 55: 5642-5646.

Swapnaja, et al., "Design, synthesis and biological evaluation of diaziridinyl quinone isoxazole hybrids," European Journal of Medicinal Chemistry, (2016), vol. 117: 85-98.

Khan, et al., "Bihetaryls VI1. A 3,4"-Bipyrazolyl from 1H, 4H-Pyrano [2,3-c] Pyrazol-4-One," AFINIDAD XIV, (1988), vol. 414: 173-174.

Wiethan, et al., "Synthesis of tetra-substituted 5-trifluoromethylpyrazoles via sequential halogenation/palladium-catalyzed C—C and C—N cross-coupling," Organic & Biomolecular Chemistry, (2016), vol. 14: 2352-2359.

Baur, et al., "Polydisperse Ethoxylated Fatty Alcohol Surfactants as Accelerators of Cuticular Penetration. 1. Effects of Ethoxy Chain Length and the Size of the Penetrants," Pestic. Sci., (1997), vol. 51:131-152.

Pokhodylo, et al., "Synthesis of ethyl 4,5-disubstitued 2-azido-3-thiophenecarboxylates and use in the synthesis of thieno[3,2-e][1,2,3]triazolo[1,5-a]pyrimidin-5(4H)-ones," Tetrahedron, (2009), vol. 65: 2678-2683.

Siddiki, et al., "One pot synthesis of aromatic azide using sodium nitrite and hydrazine hydrate," Tetrahedron Letters, (2013), vol. 54: 1294-1297.

Pesticide Manual, http://www.alanwood.net/pesticides, (2019).

"Absolute stereochemistry of Cyclopentanecarboxylic acid", Answer 3-6, 8, 12, 15 of 36 Registry Copyright 2022 ACS on STN, Chemical Library.

STN Registry, CAS No. 2026783-88-8, Nov. 8, 2016.
STN Registry, CAS No. 2026674-19-9, Nov. 8, 2016.
STN Registry, CAS No. 1938347-03-5, Jun. 24, 2016.
STN Registry, CAS No. 1828327-89-4, Dec. 13, 2015.
STN Registry, CAS No. 1828002-68-1, Dec. 13, 2015.
STN Registry, CAS No. 1627262-24-1, Sep. 28, 2014.
STN Registry, CAS No. 1570100-00-3, Mar. 19, 2014.
STN Registry, CAS No. 1252349-58-8, Nov. 10, 2010.
STN Registry, CAS Nos. 1340923-51-4, 1340891-80-6, 1340816-62-7, 1340816-53-6, and 1340693-10-8.
STN Registry, CAS No. 1575597-38-4 (Mar. 28, 2014).

* cited by examiner

TRICYCLIC CARBOXAMIDES FOR CONTROLLING ARTHROPODS

CROSS-REFERENCE TO RELATED APPLICATIONS

This application is the National Stage entry of International Application No. PCT/EP2018/057614, filed 26 Mar. 2018, which claims priority to European Patent Application No. 17164442.0, filed 31 Mar. 2017.

BACKGROUND

Field

The present application relates to novel compounds, to methods for preparation thereof and to use thereof for controlling animal pests, in particular arthropods and especially insects, arachnids and nematodes.

Description of Related Art

It is known that particular halogen-substituted compounds have insecticidal activity (EP 1 911 751, WO2012/069366, WO2012/080376, WO2012/107434 and WO2012/175474).

WO 2011/113756 discloses triazole derivatives having insecticidal activity.

In addition, it is known that certain halogen-substituted compounds have cytokine-inhibitory activities (WO 2000/07980).

Modern crop protection compositions have to meet many demands, for example in relation to the level, duration and spectrum of their action and possible use. Questions of toxicity and of combinability with other active ingredients or formulation auxiliaries play a role, as does the question of the cost and complexity involved in the synthesis of an active ingredient. In addition, resistances can occur. For all these reasons, the search for novel crop protection agents can never be considered to be complete, and there is a constant need for novel compounds having properties improved over the known compounds at least in relation to individual aspects.

SUMMARY

It was an object of the present invention to provide compounds which broaden the spectrum of the pesticides in various aspects and/or improve their activity.

It has now been found that, surprisingly, particular halogen-substituted compounds and salts thereof have biological properties and are especially suitable for controlling animal pests, and therefore have particularly good usability in the agrochemical sector and in the animal health sector.

Similar compounds have already become known from WO 2010/051926, WO 2012/102387, WO 2012/000896, WO 2011/045224, WO 2008/074835.

Embodiments of the Compounds According to the Invention

One aspect of the present invention relates to novel halogen-substituted compounds which have insecticidal, acaricidal and/or parasiticidal activity and are of the general formula (I)

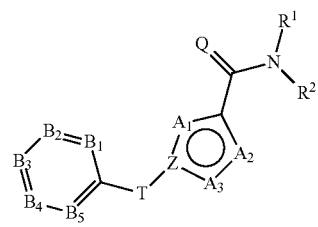

in which $R^1$ is H, optionally in each case mutually independently substituted by one or more substituents selected from amino, hydroxyl, halogen, nitro, cyano, isocyano, mercapto, isothiocyanato, $C_1$-$C_4$-carboxyl, carbonamide, $SF_5$, aminosulfonyl, $C_1$-$C_4$-alkyl, $C_3$-$C_4$-cycloalkyl, $C_2$-$C_4$-alkenyl, $C_5$-$C_6$-cycloalkenyl, $C_2$-$C_4$-alkynyl, N-mono-$C_1$-$C_4$-alkylamino, N,N-di-$C_1$-$C_4$-alkylamino, N—$C_1$-$C_4$-alkanoylamino, $C_1$-$C_4$-alkoxy, $C_2$-$C_4$-alkenyloxy, $C_2$-$C_4$-alkynyloxy, $C_3$-$C_4$-cycloalkoxy, $C_5$-$C_6$-cycloalkenyloxy, $C_1$-$C_4$-alkoxycarbonyl, $C_2$-$C_4$-alkenyloxycarbonyl, $C_2$-$C_4$-alkynyloxycarbonyl, $C_6$-,$C_{10}$-,$C_{14}$-aryloxycarbonyl, $C_1$-$C_4$-alkanoyl, $C_2$-$C_4$-alkenylcarbonyl, $C_2$-$C_4$-alkynylcarbonyl, $C_6$-,$C_{10}$-,$C_{14}$-arylcarbonyl, $C_1$-$C_4$-alkylsulfanyl, $C_3$-$C_4$-cycloalkylsulfanyl, $C_1$-$C_4$-alkylthio, $C_2$-$C_4$-alkenylthio, $C_5$-$C_6$-cycloalkenylthio, $C_2$-$C_4$-alkynylthio, $C_1$-$C_4$-alkylsulfenyl and $C_1$-$C_4$-alkylsulfinyl, wherein both enantiomers of the $C_1$-$C_4$-alkylsulfanyl group are included, $C_1$-$C_4$-alkylsulfonyl, N-mono-$C_1$-$C_4$-alkylaminosulfonyl, N,N-di-$C_1$-$C_4$ alkylaminosulfonyl, $C_1$-$C_4$ alkylphosphinyl, $C_1$-$C_4$-alkylphosphonyl, wherein for $C_1$-$C_4$-alkylphosphinyl or $C_1$-$C_4$-alkylphosphonyl both enantiomers are included, N—$C_1$-$C_4$-alkylamanocarbonyl, N,N-di-$C_1$-$C_4$-alkylaminocarbonyl, N—$C_1$-$C_4$-alkanoylaminocarbonyl, N—$C_1$-$C_4$-alkanoyl-N—$C_1$-$C_4$-alkylaminocarbonyl, $C_6$-,$C_{10}$-,$C_{14}$-aryl, $C_6$-,$C_{10}$-,$C_{14}$-aryloxy, benzyl, benzyloxy, benzylthio, $C_6$-,$C_{10}$-,$C_{14}$-arylthio, $C_6$-,$C_{10}$-,$C_{14}$-arylamino, benzylamino, heterocyclyl and trialkylsilyl, having substituents linked by a double bond such as $C_1$-$C_4$-alkylidene (e.g. methylidene or ethylidene), an oxo group-substituted or an imino group-substituted $C_1$-$C_6$-alkyl, $C_2$-$C_6$-alkenyl, $C_2$-$C_6$-alkynyl, $C_3$-$C_7$-cycloalkyl, $C_1$-$C_6$-alkylcarbonyl, $C_1$-$C_6$-alkoxycarbonyl, $C_6$-,$C_{10}$-,$C_{14}$-aryl($C_1$-$C_3$)-alkyl, 3, 4, 5, 6, 7, 8, 9 or 10-membered heterocyclyl (e.g. thietanyl such as thiethanyl-3-yl, oxidothiethane such as 1-oxidothietan-3-yl, or dioxidothiethane such as 1,1-dioxidothietan-3-yl) or 3, 4, 5, 6, 7, 8, 9 or 10-membered-heterocyclyl($C_1$-$C_3$)-alkyl, preferably $C_3$-$C_7$-cycloalkyl optionally substituted by halogen or cyano, or $C_6$-,$C_{10}$-,$C_{14}$-aryl($C_1$-$C_3$)-alkyl, wherein $C_6$-,$C_{10}$-,$C_{14}$-aryl may optionally be substituted mutually independently by one or more substituents selected from amino, hydroxyl, halogen, nitro, cyano, isocyano, mercapto and $C_1$-$C_4$-alkyl, or $C_1$-$C_6$-alkylcarbonyl;

more preferably $C_3$-cycloalkyl optionally substituted by cyano (especially cyclopropyl or 1-CN-cyclopropyl) or $C_6$-aryl($C_1$-$C_3$)-alkyl (especially —$CH_2$-$C_6H_5$);

$R^2$ is H or optionally mutually independently substituted by one or more substituents selected from amino, hydroxyl, halogen, nitro, cyano, mercapto, $C_1$-$C_4$-carboxyl, carbonamide, aminosulfonyl, $C_1$-$C_4$-alkyl, $C_3$-$C_4$-cycloalkyl, $C_2$-$C_4$-alkenyl, $C_5$-$C_6$-cycloalkenyl, $C_2$-$C_4$-alkynyl, N-mono-$C_1$-$C_4$-alkylamino, N,N-di-$C_1$-$C_4$-alkylamino, N—$C_1$-$C_4$-alkanoylamino, $C_1$-$C_4$-alkoxy, $C_2$-$C_4$-alkenyloxy, $C_2$-$C_4$-alkynyloxy, $C_3$-$C_4$-cycloalkoxy, $C_5$-$C_6$-cycloalkenyloxy, $C_1$-$C_4$-alkoxycarbonyl, $C_2$-$C_4$-alkenyloxycarbonyl, $C_2$-$C_4$-alkynyloxycarbonyl, $C_6$-,$C_{10}$-,$C_{14}$-aryloxycarbonyl, $C_1$-$C_4$-alkanoyl, $C_2$-$C_4$-alkenylcarbonyl, $C_2$-$C_4$-alkynylcarbonyl, $C_6$-,$C_{10}$-,$C_{14}$-arylcarbonyl, $C_1$-$C_4$-alkylsulfanyl, $C_3$-$C_4$-cycloalkylsulfanyl, $C_1$-$C_4$-alkylthio, $C_2$-$C_4$-alkenylthio, $C_5$-$C_6$-cycloalkenylthio, $C_2$-$C_4$-alkynylthio, $C_1$-$C_4$-alkylsulfenyl and $C_1$-$C_4$-alkylsulfinyl, wherein both enantiomers of the $C_1$-$C_4$-alkylsulfinyl group are included, $C_1$-$C_4$-alkylsulfonyl, N-mono-$C_1$-$C_4$-alkylaminosulfonyl, N,N-di-$C_1$-$C_4$-alkylaminosulfonyl, $C_1$-$C_4$-alkylphosphinyl, $C_1$-$C_4$-alkylphosphonyl, wherein both enantiomers are included for $C_1$-$C_4$-alkylphosphinyl or $C_1$-$C_4$-alkylphosphonyl, N—$C_1$-$C_4$-alkylaminocarbonyl, N,N-di-$C_1$-$C_4$-alkylaminocarbonyl, N—$C_1$-$C_4$-alkanoylaminocarbonyl, N—$C_1$-$C_4$-alkanoyl-N—$C_1$-$C_4$-alkylaminocarbonyl, $C_6$-,$C_{10}$-,$C_{14}$-aryl, $C_6$-,$C_{10}$-,$C_{14}$-aryloxy, benzyloxy, benzylthio, $C_6$-,$C_{10}$-,$C_{14}$-arylthio, $C_6$-,$C_{10}$-,$C_{14}$-arylamino, benzylamino, heterocyclyl and trialkylsilyl, having substituents linked by a double bond such as $C_1$-$C_4$-alkylidene (e.g. methylidene or ethylidene) or an oxo group-substituted $C_1$-$C_6$-alkyl (preferably H or —$CH_3$);

the moieties $A_1$, $A_2$ and $A_3$ are each independently N, O, $CR^3$, S or N—$R^4$, preferably N, $CR^3$, S or N—$R^4$, wherein $A_1$, $A_2$, $A_3$, Z and the carbon atom of the ring form an aromatic system;

$R^3$ is each independently H, Cl, F, I, Br or optionally halogenated $C_1$-$C_4$-alkyl, preferably methyl;

$R^4$ is each independently H or optionally halogenated $C_1$-$C_4$-alkyl, preferably methyl;

Q is O or S, preferably O;

Z is C or N; preferably C;

$B_1$ and $B_5$ are each independently N or C—$R^5$ and $B_2$, $B_3$ and $B_4$ are each independently C—$R^5$, wherein $R^5$ is each independently H, halogen, cyano, nitro, $SF_5$, in each case optionally substituted by one or more substituents selected from amino, hydroxyl, halogen, nitro, cyano, isocyano, mercapto, isothiocyanato, $C_1$-$C_4$-carboxyl, carbonamide, $SF_5$, aminosulfonyl, $C_1$-$C_4$-alkyl, $C_3$-$C_4$-cycloalkyl, $C_2$-$C_4$-alkenyl, $C_5$-$C_6$-cycloalkenyl, $C_2$-$C_4$-alkynyl, N-mono-$C_1$-$C_4$-alkylamino, N,N-di-$C_1$-$C_4$-alkylamino, N—$C_1$-$C_4$-alkanoylamino, $C_1$-$C_4$-alkoxy, $C_2$-$C_4$-alkenyloxy, $C_2$-$C_4$-alkynyloxy, $C_3$-$C_4$-cycloalkoxy, $C_5$-$C_6$-cycloalkenyloxy, $C_1$-$C_4$-alkoxycarbonyl, $C_2$-$C_4$-alkenyloxycarbonyl, $C_2$-$C_4$-alkynyloxycarbonyl, $C_6$-,$C_{10}$-,$C_{14}$-aryloxycarbonyl, $C_1$-$C_4$-alkanoyl, $C_2$-$C_4$-alkenylcarbonyl, $C_2$-$C_4$-alkynylcarbonyl, $C_6$-,$C_{10}$-,$C_{14}$-arylcarbonyl, $C_1$-$C_4$-alkylsulfanyl, $C_3$-$C_4$-cycloalkylsulfanyl, $C_1$-$C_4$-alkylthio, $C_2$-$C_4$-alkenylthio, $C_5$-$C_6$-cycloalkenylthio, $C_2$-$C_4$-alkynylthio, $C_1$-$C_4$-alkylsulfenyl and $C_1$-$C_4$-alkylsulfinyl, wherein both enantiomers of the $C_1$-$C_4$-alkylsulfenyl group are included, $C_1$-$C_4$-alkylsulfonyl, N-mono-$C_1$-$C_4$-alkylaminosulfonyl, N,N-di-$C_1$-$C_4$-alkylaminosulfonyl, $C_1$-$C_4$-alkylphosphinyl, $C_1$-$C_4$-alkylphosphonyl, wherein both enantiomers are included for $C_1$-$C_4$-alkylphosphinyl or $C_1$-$C_4$-alkylphosphonyl, N—$C_1$-$C_4$-alkylaminocarbonyl, N,N-di-$C_1$-$C_4$-alkylaminocarbonyl, N—$C_1$-$C_4$-alkanoylaminocarbonyl, N—$C_1$-$C_4$-alkanoyl-N—$C_1$-$C_4$-alkylaminocarbonyl, $C_6$-,$C_{10}$-,$C_{14}$-aryl, $C_6$-,$C_{10}$-,$C_{14}$-aryloxy, benzyl, benzyloxy, benzylthio, $C_6$-,$C_{10}$-,$C_{14}$-arylthio, $C_6$-,$C_{10}$-,$C_{14}$-arylamino, benzylamino, heterocyclyl and trialkylsilyl, having substituents linked by a double bond such as $C_1$-$C_4$-alkylidene (e.g. methylidene or ethylidene), an oxo group-substituted or an imino group-substituted $C_1$-$C_6$-alkyl, $C_3$-$C_6$-cycloalkyl, $C_1$-$C_6$-alkoxy, N—$C_1$-$C_6$-alkoxyimino-$C_1$-$C_3$ alkyl, $C_1$-$C_6$-alkylsulfanyl, $C_1$-$C_6$-alkylsulfinyl, $C_1$-$C_6$-alkylsulfonyl, N—$C_1$-$C_6$-alkylamino or NA-di-$C_1$-$C_6$-alkylamino;

T is one of the 5-membered heteroaromatic systems T1-T4 and T6 shown below, where the bond to

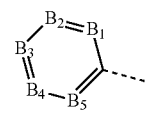

is marked with a hash #,

T1

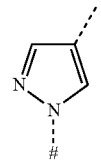

T2

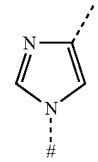

T3

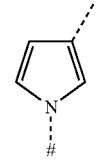

T4

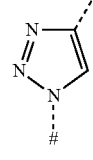

T6

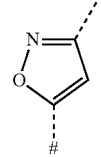

and salts, N-oxides and tautomeric forms of the compounds of the formula (I). In a preferred embodiment, R2 is H or methyl.

DETAILED DESCRIPTION OF A PREFERRED EMBODIMENT

A preferred embodiment of the present invention relates to compounds of formula (I) described above, wherein $R^2$ is H or methyl.

A further preferred embodiment relates to compounds of formula (I) described above, wherein T is T1, T2 or T4, more preferably T1.

A further preferred embodiment relates to compounds of formula (I) described above, wherein $R^1$ is cyclopropyl optionally substituted by cyano (preferably cyclopropyl or 1-CN-cyclopropyl) or $C_6$-aryl($C_1$-$C_3$)-alkyl (preferably —$CH_2$-$C_6H_5$). $R^1$ is particularly preferably benzyl, cyclopropyl or 1-CN-cyclopropyl, especially preferably cyclopropyl or 1-CN-cyclopropyl.

A further preferred embodiment relates to compounds of formula (I) described above, wherein Q is O.

A further preferred embodiment relates to compounds of formula (I) described above, wherein $A_3$ is S.

A further preferred embodiment relates to compounds of formula (I) described above, wherein $A_3$ is S, Z is C, $A_2$ is C-(optionally halogenated $C_1$-$C_4$-alkyl) (preferably C—$CH_3$), C—H or C-Hal, in which Hal is Cl, Br, or I, preferably Br or Cl, and $A_1$ is C—H or N. In a further preferred embodiment, $A_3$ is S, Z is C, $A_2$ is C-Hal, in which Hal is Cl, Br, or I, and $A_1$ is C—H. In a further preferred embodiment $A_1$ is S, Z is C, $A_2$ is C—H or C-Hal, in which Hal is Cl, Br, or I, preferably $C_1$, and $A_1$ is N.

A further preferred embodiment relates in this case to compounds of formula (I) described above, wherein $A_1$ is S, preferably in which $A_1$ is S, $A_2$ is C—H or C-Hal, preferably C-Hal, in which Hal is $C_1$, Br, or I, preferably Br or Cl, even more preferably Cl, Z is C, and $A_3$ is C—H.

A further preferred embodiment relates in this case to compounds of formula (I) described above, wherein $A_3$ is O.

A further preferred embodiment relates in this case to compounds of formula (I) described above, wherein $A_3$ is O, Z is C, $A_1$ is C—H and $A_2$ is C-Hal, in which Hal is Cl, Br, or I, preferably Cl.

A further preferred embodiment relates in this case to compounds of formula (I) described above, wherein $A_3$ is C—H, $A_1$ is S, Z is C and $A_2$ is C-Hal, in which Hal is Cl, Br, or I, preferably Cl.

A further preferred embodiment relates in this case to compounds of formula (I) described above, wherein $A_3$ is C—H or C-Hal, in which Hal is Cl, Br, or I, preferably $C_1$, $A_2$ is N—H or N—($C_1$-$C_4$-alkyl) (preferably N—($C_1$-$C_4$-alkyl), more preferably N—$CH_3$), $A_1$ is C—H, C—Hal, in which Hal is Cl, Br, or I, preferably $C_1$, or C—($C_1$-$C_4$-alkyl), more preferably in which $A_3$ is C—H or C—$C_1$, $A_2$ is N—$CH_3$, $A_1$ is C—H.

A further preferred embodiment relates in this case to compounds of formula (I) described above, wherein Z is C, $A_1$ is N, $A_2$ is S and $A_3$ is C—H.

A further preferred embodiment relates in this case to compounds of formula (I) described above, in which $B_1$ and $B_5$ are in each case C—H, C—$CH_3$ or C-Hal, preferably C—Cl. Particularly preferably in which $B_1$ and $B_5$ are in each case C—Cl.

A further preferred embodiment relates in this case to compounds of formula (I) described above, in which $B_2$ and $B_4$ are in each case C—H.

A further preferred embodiment relates in this case to compounds of formula (I) described above, in which $B_3$ is $CR^5$ and $R^5$ is perhalogenated $C_1$-$C_4$-alkyl, preferably perfluorinated $C_1$-$C_4$-alkyl, more preferably perfluorinated propyl.

A further preferred embodiment relates in this case to compounds of the formula (Ia)

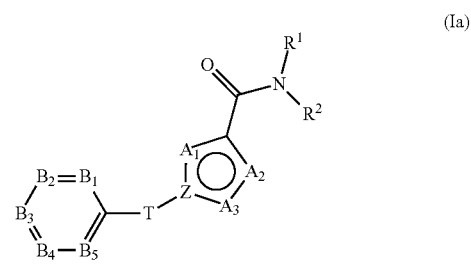

(Ia)

in which $B_1$ to $B_5$, $A_1$ to $A_3$, Z, $R^1$, $R^2$ and T are as defined herein for compounds of the formula (I) and preferred embodiments thereof.

A further preferred embodiment relates in this case to compounds of the formula (Ib)

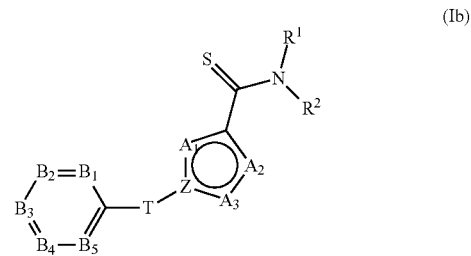

(Ib)

in which $B_1$ to $B_5$, $A_1$ to $A_3$, Z, $R^1$, $R^2$ and T are as defined herein for compounds of the formula (I) and preferred embodiments thereof.

Further preferred embodiments relate in each case to compounds of the formulae (1c), (1d) and (1f) to (1k), in which each of the optionally occurring symbols $A_1$ to $A_3$, $B_1$ to $B_5$, T, Z, $R^1$ to $R^4$, if not explicitly defined for one of these formulae, are as defined herein for compounds of the formula (I) and preferred embodiments thereof and "alk" is $C_1$-$C_4$-alkyl, "Hal" is chlorine or bromine and V is $C_1$-$C_4$-alkoxy or N($R^1R^2$).

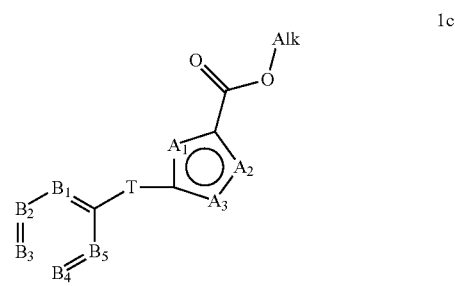

1c

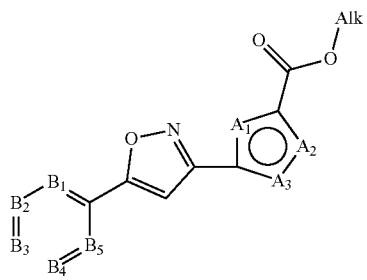
1d

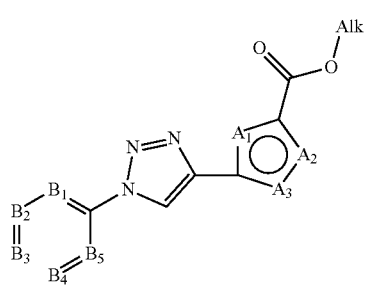
1f

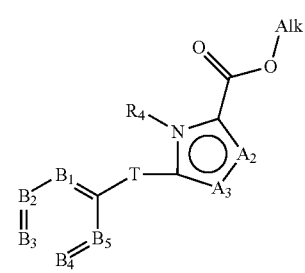
1g

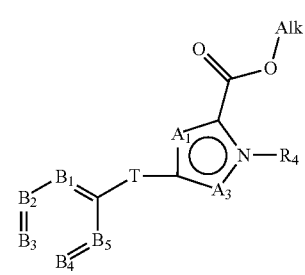
1h

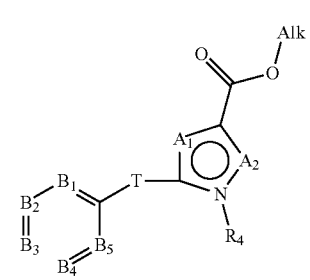
1i

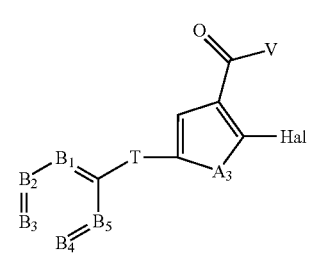
1j

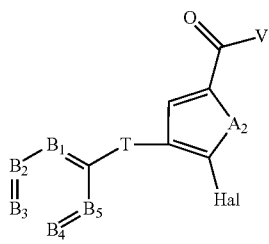
1k

A further preferred embodiment relates in this case to compounds of the formula (I'a)

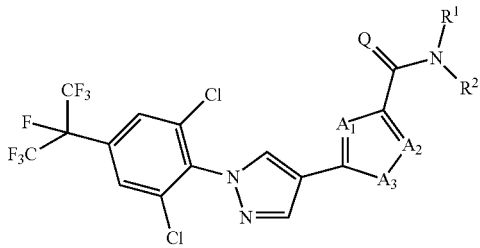
(I'a)

in which Q, $R^1$, $R^2$, $A_1$, $A_2$ and $A_3$ are as defined herein for compounds of the formula (I) and preferred embodiments thereof.

A further preferred embodiment relates in this case to compounds according to the formula (I'b)

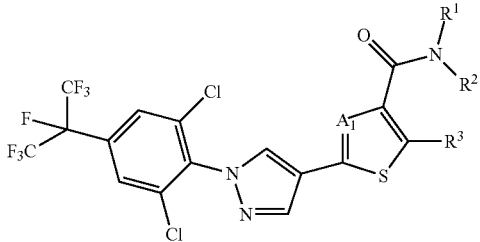
(I'b)

in which $A_1$ is N or C—H and $R^3$ is defined as described herein, preferably $C_1$-$C_4$-alkyl, C—H or C-Hal, in which Hal is Cl, Br, or I, preferably Br or Cl, particularly preferably $R^3$ is $CH_3$, and otherwise $R^1$ and $R^2$ are defined as described herein.

A further preferred embodiment relates in this case to compounds according to the formula (I'c)

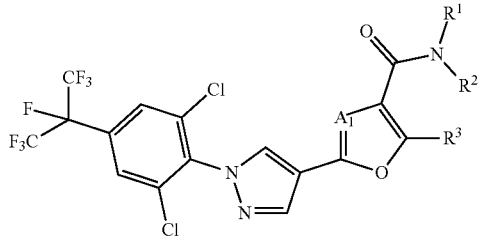
(I'c)

in which $A_1$ is C—H and $R_3$ is preferably C—Cl and otherwise $R^1$ and $R^2$ are defined as described herein.

A further preferred embodiment relates in this case to compounds according to the formula (I'd)

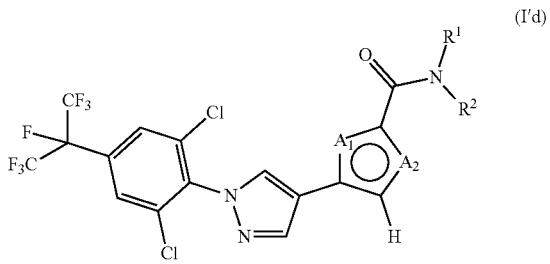

in which $A_1$ is C—$R^3$, preferably C—H, if $A_2$ is N-(halogenated $C_1$-$C_4$-alkyl) or N—($C_1$-$C_4$-alkyl); or $A_1$ is N if $A_2$ is S and otherwise $R^1$ and $R^2$ are defined as described herein.

$R^2$ in one of the formulae (I'a), (I'b), (I'c) and (I'd) is preferably H or $CH_3$ and $R^1$ is cyclopropyl optionally substituted by CN (such as cyclopropyl or 1-CN-cyclopropyl).

A further aspect relates to an insecticidal composition comprising at least one compound of the formula (I) or of a formula derived from formula (I) as described above, and an extender and/or a surface-active substance.

A further aspect relates to a method for protecting transgenic or conventional seed and the plant that arises therefrom from infestation by pests, characterized in that the seed is treated with at least one compound of formula (I) described above.

A further aspect relates to the use of compounds of formula (I) described above for controlling pests.

A further aspect relates to seed, in which a compound of formula (I) described above has been applied to the seed as a constituent of a coating or as a further layer or further layers in addition to a coating.

A further aspect relates to a method for protecting transgenic or conventional seed and the plant that arises therefrom from infestation by pests, characterized in that the seed is treated with at least one compound of the formula (I) or a formula derived from formula (I) as described herein.

Yet a further aspect relates to the use of compounds of the formula (I) or a formula derived from formula (I) as described herein or of an insecticidal composition as described herein for controlling pests.

A further aspect relates to the use of compounds of the formula (I) or a formula derived from formula (I) as described herein in vector control.

Yet a further aspect relates to seed in which a compound of the formula (I) or a formula derived from formula (I) as described herein has been applied to the seed as a constituent of a coating or as a further layer or further layers in addition to a coating.

Accordingly, a further aspect relates to a method for applying a coating comprising at least one compounds of the formula (I) or a formula derived from formula (I) as described herein or for applying a compounds of the formula (I) or a formula derived from formula (I) as described herein, which is applied to seed as a layer or further layers in addition to a coating, comprising the steps of a) mixing seeds with a coating material consisting of or comprising a compounds of the formula (I) or a formula derived from formula (I) as described herein, b) enriching the coated seed composition obtained, c) drying the enriched seed composition obtained, d) dis- or deagglomerating the dried seed composition obtained.

Depending on the nature of the substituents, the compounds of the formula (I) or a formula derived from formula (I) described here may optionally be in the form of geometric and/or optically active isomers or corresponding isomer mixtures in different compositions. The invention relates both to the pure isomers and to the isomer mixtures.

The compounds according to the invention can also be present as metal complexes.

Definitions

The person skilled in the art is aware that, if not stated explicitly, the expressions "a" or "an" as used in the present application may, depending on the situation, mean "one (1)", "one (1) or more" or "at least one (1)".

Structures having a variable number of possible carbon atoms (C atoms) may be referred to in the present application as $C_{lower\ limit\ of\ carbon\ atoms}$-$C_{upper\ limit\ of\ carbon\ atoms}$ structures ($C_{LL}$-$C_{UL}$ structures), in order thus to be stipulated more specifically. Example: an alkyl group may consist of 3 to 10 carbon atoms and in that case corresponds to $C_3$-$C_{10}$-alkyl. Ring structures composed of carbon atoms and heteroatoms may be referred to as "LL- to UL-membered" structures. One example of a 6-membered ring structure is toluene (a 6-membered ring structure substituted by a methyl group).

It is obvious to the person skilled in the art that examples given in the present application are not to be considered as limiting, but rather merely describe some embodiments in more detail.

In composite substituents (e.g. hydroxyalkyl or alkoxy or alkylcarbonyl), the second-mentioned substituent is in each case bonded to the basic structure (e.g. hydroxymethyl: —$CH_2$—OH or methoxy: —O—$CH_3$ or methylcarbonyl: —C(=O)—$CH_3$).

In the definitions of the symbols given in the above formulae, collective terms which are generally representative of the following substituents were used:

Halogen refers to the elements of the 7th main group, preferably fluorine, chlorine, bromine and iodine, more preferably fluorine, chlorine and bromine.

According to the invention, "alkyl"—on its own or as part of a chemical group—represents straight-chain or branched hydrocarbons preferably having 1 to 6 carbon atoms, for example methyl, ethyl, n-propyl, isopropyl, n-butyl, isobutyl, s-butyl, t-butyl, pentyl, 1-methylbutyl, 2-methylbutyl, 3-methylbutyl, 1,2-dimethylpropyl, 1,1-dimethylpropyl, 2,2-dimethylpropyl, 1-ethylpropyl, hexyl, 1-methylpentyl, 2-methylpentyl, 3-methylpentyl, 4-methylpentyl, 1,2-dimethylpropyl, 1,3-dimethylbutyl, 1,4-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl and 2-ethylbutyl. Preference is also given to alkyls having 1 to 4 carbon atoms such as, inter alia, methyl, ethyl, n-propyl, isopropyl, n-butyl, isobutyl, s-butyl or t-butyl. The alkyl groups according to the invention may be substituted by one or more identical or different radicals.

According to the invention, "alkenyl"—on its own or as part of a chemical group—represents straight-chain or branched hydrocarbons preferably having 2 to 6 carbon atoms and at least one double bond, for example vinyl, 2-propenyl, 2-butenyl, 3-butenyl, 1-methyl-2-propenyl, 2-methyl-2-propenyl, 2-pentenyl, 3-pentenyl, 4-pentenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-2-butenyl, 1,2-dimethyl-3-butenyl, 1,3-dimethyl-2-butenyl, 2,2-dimethyl-3-butenyl, 2,3-dimethyl-2-butenyl, 2,3-dimethyl-3-butenyl, 1-ethyl-2-butenyl, 1-ethyl-3-butenyl, 2-ethyl-2-butenyl, 2-ethyl-3-butenyl, 1,1,2-trimethyl-2-propenyl, 1-ethyl-1-methyl-2-propenyl and 1-ethyl-2-methyl-2-propenyl. Preference is also given to alkenyls having 2 to 4 carbon atoms such as, inter alia, 2-propenyl, 2-butenyl or 1-methyl-2-propenyl. The alkenyl groups according to the invention may be substituted by one or more identical or different radicals.

According to the invention, "alkynyl"—on its own or as part of a chemical group—represents straight-chain or branched hydrocarbons preferably having 2 to 6 carbon atoms and at least one triple bond, for example 2-propynyl, 2-butynyl, 3-butynyl, 1-methyl-2-propynyl, 2-pentynyl, 3-pentynyl, 4-pentynyl, 1-methyl-3-butynyl, 2-methyl-3-butynyl, 1-methyl-2-butynyl, 1,1-dimethyl-2-propynyl, 1-ethyl-2-propynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-4-pentynyl, 4-methyl-2-pentynyl, 1,1-dimethyl-3-butynyl, 1,2-dimethyl-3-butynyl, 2,2-dimethyl-3-butynyl, 1-ethyl-3-butynyl, 2-ethyl-3-butynyl, 1-ethyl-1-methyl-2-propynyl and 2,5-hexadiynyl. Preference is also given to alkynyls having 2 to 4 carbon atoms such as, inter alia, ethynyl, 2-propynyl or 2-butynyl-2-propenyl. The alkynyl groups according to the invention may be substituted by one or more identical or different radicals.

According to the invention, "cycloalkyl"—alone or as part of a chemical group—represents mono-, bi- or tricyclic hydrocarbons, preferably having 3 to 10 carbons, for example cyclopropyl, cyclobutyl, cyclopentyl, cyclohexyl, cycloheptyl, cyclooctyl, bicyclo[2.2.1]heptyl, bicyclo[2.2.2]octyl or adamantyl. Preference is also given to cycloalkyls having 3, 4, 5, 6 or 7 carbon atoms such as, inter alia, cyclopropyl or cyclobutyl. The cycloalkyl groups according to the invention may be substituted by one or more identical or different radicals.

According to the invention, "alkylcycloalkyl" represents mono-, bi- or tricyclic alkylcycloalkyl preferably having 4 to 10 or 4 to 7 carbon atoms, for example methylcyclopropyl, ethylcyclopropyl, isopropylcyclobutyl, 3-methylcyclopentyl and 4-methylcyclohexyl. Preference is also given to alkylcycloalkyls having 4, 5 or 7 carbon atoms such as, inter alia, ethylcyclopropyl or 4-methylcyclohexyl. The alkylcycloalkyl groups according to the invention may be substituted by one or more identical or different radicals.

According to the invention, "cycloalkylalkyl" represents mono-, bi- or tricyclic cycloalkylalkyl preferably having 4 to 10 or 4 to 7 carbon atoms such as, for example, cyclopropylmethyl, cyclobutylmethyl, cyclopentylmethyl, cyclohexylmethyl and cyclopentylethyl. Preference is also given to cycloalkylalkyls having 4, 5 or 7 carbon atoms such as, inter alia, cyclopropylmethyl or cyclobutylmethyl. The cycloalkylalkyl groups according to the invention may be substituted by one or more identical or different radicals.

According to the invention, "hydroxyalkyl" represents a straight-chain or branched alcohol preferably having 1 to 6 carbon atoms such as, for example, methanol, ethanol, n-propanol, isopropanol, n-butanol, isobutanol, s-butanol and t-butanol. Preference is also given to hydroxyalkyl groups having 1 to 4 carbon atoms. The hydroxyalkyl groups according to the invention may be substituted by one or more identical or different radicals.

According to the invention, "alkoxy" represents a straight-chain or branched —O-alkyl preferably having 1 to 6 carbon atoms such as, for example, methoxy, ethoxy, n-propoxy, isopropoxy, n-butoxy, isobutoxy, s-butoxy and t-butoxy. Preference is also given to alkoxy groups having 1 to 4 carbon atoms. The alkoxy groups according to the invention may be substituted by one or more identical or different radicals.

According to the invention, "alkylsulfanyl" represents straight-chain or branched S-alkyl preferably having 1 to 6 carbon atoms such as, for example, methylthio, ethylthio, n-propylthio, isopropylthio, n-butylthio, isobutylthio, s-butylthio and t-butylthio. Preference is also given to alkylsulfanyl groups having 1 to 4 carbon atoms. The alkylsulfanyl groups according to the invention may be substituted by one or more identical or different radicals.

According to the invention, "alkylsulfanyl" represents straight-chain or branched alkylsulfinyl preferably having 1 to 6 carbon atoms such as, for example, methylsulfinyl, ethylsulfinyl, n-propylsulfinyl, isopropylsulfinyl, n-butylsulfinyl, isobutylsulfinyl, s-butylsulfinyl and t-butylsulfinyl. Preference is also given to alkylsulfinyl groups having 1 to 4 carbon atoms. The alkylsulfinyl groups according to the invention may be substituted by one or more identical or different radicals.

According to the invention, "alkylsulfonyl" represents straight-chain or branched alkylsulfonyl preferably having 1 to 6 carbon atoms such as, for example, methylsulfonyl, ethylsulfonyl, n-propylsulfonyl, isopropylsulfonyl, n-butylsulfonyl, isobutylsulfonyl, s-butylsulfonyl and t-butylsulfonyl. Preference is also given to alkylsulfonyl groups having 1 to 4 carbon atoms. The alkylsulfonyl groups according to the invention may be substituted by one or more identical or different radicals.

According to the invention, "alkylcarbonyl" represents straight-chain or branched alkyl-C(=O) preferably having 2 to 7 carbon atoms such as methylcarbonyl, ethylcarbonyl, n-propylcarbonyl, isopropylcarbonyl, s-butylcarbonyl and t-butylcarbonyl. Preference is also given to alkylcarbonyls having 1 to 4 carbon atoms. The alkylcarbonyls according to the invention may be substituted by one or more identical or different radicals.

According to the invention, "cycloalkylcarbonyl" represents straight-chain or branched cycloalkylcarbonyl preferably having 3 to 10 carbon atoms in the cycloalkyl moiety such as, for example, cyclopropylcarbonyl, cyclobutylcarbonyl, cyclopentylcarbonyl, cyclohexylcarbonyl, cycloheptylcarbonyl, cyclooctylcarbonyl, bicyclo[2.2.1]heptyl, bicyclo[2.2.2]octylcarbonyl and adamantylcarbonyl. Preference is also given to cycloalkylcarbonyl having 3, 5 or 7 carbon atoms in the cycloalkyl moiety. The cycloalkylcarbonyl groups according to the invention may be substituted by one or more identical or different radicals.

According to the invention, "alkoxycarbonyl"—alone or as a constituent of a chemical group—represents straight-chain or branched alkoxycarbonyl, preferably having 1 to 6 carbon atoms or having 1 to 4 carbon atoms in the alkoxy moiety such as, for example, methoxycarbonyl, ethoxycarbonyl, n-propoxycarbonyl, isopropoxycarbonyl, s-butoxycarbonyl and t-butoxycarbonyl. The alkoxycarbonyl groups according to the invention may be substituted by one or more identical or different radicals.

According to the invention, "alkylaminocarbonyl" represents straight-chain or branched alkylaminocarbonyl having preferably 1 to 6 carbon atoms or 1 to 4 carbon atoms in the alkyl moiety, for example methylaminocarbonyl, ethylaminocarbonyl, n-propylaminocarbonyl, isopropylaminocarbonyl, s-butylaminocarbonyl and t-butylaminocarbonyl. The alkylaminocarbonyl groups according to the invention may be substituted by one or more identical or different radicals.

According to the invention, "N,N-dialkylaminocarbonyl" represents straight-chain or branched N,N-dialkylaminocarbonyl having preferably 1 to 6 carbon atoms or 1 to 4 carbon atoms in the alkyl moiety, such as, for example, N,N-dimethylaminocarbonyl, N,N-diethylaminocarbonyl, N,N-di(n-propylamino)carbonyl, N,N-di(isopropylamino)carbonyl and N,N-di-(s-butylamino)carbonyl. The N,N-dialkylaminocarbonyl groups according to the invention may be substituted by one or more identical or different radicals.

According to the invention, "aryl" represents a mono-, bi- or polycyclic aromatic system having preferably 6 to 14, in particular 6 to 10 ring carbon atoms such as, for example, phenyl, naphthyl, anthryl, phenanthrenyl, preferably phenyl. In addition, aryl also represents polycyclic systems such as tetrahydronaphthyl, indenyl, indanyl, fluorenyl, biphenyl, where the bonding site is on the aromatic system. The aryl groups according to the invention may be substituted by one or more identical or different radicals.

Examples of substituted aryls are the arylalkyls, which may likewise be substituted by one or more identical or different radicals in the $C_1$-$C_4$-alkyl and/or $C_6$-$C_{14}$-aryl moiety. Examples of such arylalkyls include benzyl and 1-phenylethyl.

According to the invention, "heterocycle", "heterocyclic ring" or "heterocyclic ring system" represents a carbocyclic ring system having at least one ring in which at least one carbon atom is replaced by a heteroatom, preferably by a heteroatom from the group consisting of N, O, S, P, B, Si, Se, and which is saturated, unsaturated or heteroaromatic and may this be unsubstituted or substituted, where the bonding site is on a ring atom. Unless defined differently, the heterocyclic ring contains preferably 3 to 9 ring atoms, especially 3 to 6 ring atoms, and one or more, preferably 1 to 4, especially 1, 2 or 3, heteroatoms in the heterocyclic ring, preferably from the group consisting of N, O, and S, although no two oxygen atoms should be directly adjacent. The heterocyclic rings usually contain not more than 4 nitrogen atoms and/or not more than 2 oxygen atoms and/or not more than 2 sulfur atoms. If the heterocyclyl radical or the heterocyclic ring is optionally substituted, it may be fused to other carbocyclic or heterocyclic rings. In the case of optionally substituted heterocyclyl, the invention also embraces polycyclic systems, for example 8-azabicyclo[3.2.1]octanyl or 1-azabicyclo[2.2.1]heptyl. In the case of optionally substituted heterocyclyl, the invention also embraces spirocyclic systems, for example 1-oxa-5-azaspiro[2.3]hexyl.

Heterocyclyl groups according to the invention are, for example, piperidinyl, piperazinyl, morpholinyl, thiomorpholinyl, dihydropyranyl, tetrahydropyranyl, dioxanyl, pyrrolinyl, pyrrolidinyl, imidazolinyl, imidazolidinyl, thiazolidinyl, oxazolidinyl, dioxolanyl, dioxolyl, pyrazolidinyl, tetrahydrofuranyl, dihydrofuranyl, oxetanyl, oxiranyl, azetidinyl, aziridinyl, oxazetidinyl, oxaziridinyl, oxazepanyl, oxazinanyl, azepanyl, oxopyrrolidinyl, dioxopyrrolidinyl, oxomorpholinyl, oxopiperazinyl and oxepanyl.

Heterocyclene, i.e. heteroaromatic systems, has a particular meaning. According to the invention, the expression "heteroaryl" represents heteroaromatic compounds, i.e. fully unsaturated aromatic heterocyclic compounds covered by the above definition of heterocycles, preferably 5- to 7-membered rings having 1 to 3, preferably 1 or 2, identical or different heteroatoms from the abovementioned group. Heteroaryls according to the invention are, for example, furyl, thienyl, pyrazolyl, imidazolyl, 1,2,3- and 1,2,4-triazolyl, isoxazolyl, thiazolyl, isothiazolyl, 1,2,3-, 1,3,4-, 1,2,4- and 1,2,5-oxadiazolyl, azepinyl, pyrrolyl, pyridyl, pyridazinyl, pyrimidinyl, pyrazinyl, 1,3,5-, 1,2,4- and 1,2,3-triazinyl, 1,2,4-, 1,3,2-, 1,3,6- and 1,2,6-oxazinyl, oxepinyl, thiepinyl, 1,2,4-triazolonyl and 1,2,4-diazepinyl. The heteroaryl groups according to the invention may also be substituted by one or more identical or different radicals. The expression "(optionally) substituted" groups/substituents, such as a substituted alkyl, alkenyl, alkynyl, alkoxy, alkylsulfanyl, alkylsulfinyl, alkylsulfonyl, cycloalkyl, aryl, phenyl, benzyl, heterocyclyl and heteroaryl radical, signify for example a substituted radical derived from an unsubstituted base structure, wherein the substituents are for example one (1) substituent or more than one substituents, preferably 1, 2, 3, 4, 5, 6, or 7, selected from a group consisting of amino, hydroxy, halogen, nitro, cyano, isocyano, mercapto, isothiocyanato, $C_1$-$C_4$-carboxy, carbonamide, $SF_5$, aminosulfonyl, $C_1$-$C_4$-alkyl, $C_3$-$C_4$-cycloalkyl, $C_2$-$C_4$-alkenyl, $C_5$-$C_6$-cycloalkenyl, $C_2$-$C_4$-alkynyl, N-mono-$C_1$-$C_4$-alkylamino, N,N-di-$C_1$-$C_4$-alkylamino, N—$C_1$-$C_4$-alkanoylamino, $C_1$-$C_4$-alkoxy, $C_2$-$C_4$-alkenyloxy, $C_2$-$C_4$-alkynyloxy, $C_3$-$C_4$-cycloalkoxy, $C_5$-$C_6$-cycloalkenyloxy, $C_1$-$C_4$-alkoxycarbonyl, $C_2$-$C_4$-alkenyloxycarbonyl, $C_2$-$C_4$-alkynyloxycarbonyl, $C_6$-,$C_{10}$-,$C_{14}$-aryloxycarbonyl, $C_1$-$C_4$-alkanoyl, $C_2$-$C_4$-alkenylcarbonyl, $C_2$-$C_4$-alkynylcarbonyl, $C_6$-,$C_{10}$-,$C_{14}$-arylcarbonyl, $C_1$-$C_4$-alkylsulfanyl, $C_3$-$C_4$-cycloalkylsulfanyl, $C_1$-$C_4$-alkylthio, $C_2$-$C_4$-alkenylthio, $C_5$-$C_6$-cycloalkenylthio, $C_2$-$C_4$-alkynylthio, $C_1$-$C_4$-alkylsulfenyl and $C_1$-$C_4$-alkylsulfinyl, wherein both enantiomers of the $C_1$-$C_4$-alkylsulfinyl group are included, $C_1$-$C_4$-alkylsulfonyl, N-mono-$C_1$-$C_4$-alkylaminosulfonyl, N,N-di-$C_1$-$C_4$-alkylaminosulfonyl, $C_1$-$C_4$-alkylphosphinyl, $C_1$-$C_4$-alkylphosphonyl, wherein for $C_1$-$C_4$-alkylphosphinyl and $C_1$-$C_4$-alkylphosphonyl both enantiomers are included, N—$C_1$-$C_4$-alkylaminocarbonyl, N,N-di-$C_1$-$C_4$-alkylaminocarbonyl, N—$C_1$-$C_4$-alkanoylaminocarbonyl, N—$C_1$-$C_4$-alkanoyl-N—$C_1$-$C_4$-alkylaminocarbonyl, $C_6$-,$C_{10}$-,$C_{14}$-aryl, $C_6$-,$C_{10}$-,$C_{14}$-aryloxy, benzyl, benzyloxy, benzylthio, $C_6$-,$C_{10}$-,$C_{14}$-arylthio, $C_6$-,$C_{10}$-,$C_{14}$-arylamino, benzylamino, heterocyclyl and trialkylsilyl, substituents attached by a double bond such as $C_1$-$C_4$-alkylidene (e.g. methylidene or ethylidene), an oxo group, an imino group and also a substituted imino group. Particularly preferred substituted groups are halogenated groups. These may have one or more halogen substituents, but these groups also have at least one C—H bond, or may be perhalogenated.

The substituents mentioned by way of example ("first substituent level") may, if they contain hydrocarbonaceous components, optionally be further substituted therein ("second substituent level"), for example by one or more of the substituents each independently selected from halogen, hydroxyl, amino, nitro, cyano, isocyano, azido, acylamino, an oxo group and an imino group. The term "(optionally) substituted" group preferably embraces just one or two substituent levels.

The inventive halogen-substituted chemical groups or halogenated groups (for example alkyl or alkoxy) are mono- or polysubstituted by halogen up to the maximum possible number of substituents. Such groups are also referred to as halo groups (for example haloalkyl). In the case of poly-substitution by halogen, the halogen atoms may be identical or different, and may all be bonded to one carbon atom or may be bonded to a plurality of carbon atoms. Here, halogen represents in particular fluorine, chlorine, bromine or iodine, preferably fluorine, chlorine or bromine and more preferably fluorine or Cl. More particularly, halogen-substituted groups are monohalocycloalkyl such as 1-fluorocyclopropyl, 2-fluorocyclopropyl or 1-fluorocyclobutyl, monohaloalkyl such as 2-chloroethyl, 2-fluoroethyl, 1-chloroethyl, 1-fluoroethyl, chloromethyl, or fluoromethyl; perhaloalkyl such as trichloromethyl or trifluoromethyl or $CF_2CF_3$, polyhaloalkyl such as difluoromethyl, 2-fluoro-2-chloroethyl, dichloromethyl, 1,1,2,2-tetrafluoroethyl or 2,2,2-trifluoroethyl. Further examples of haloalkyls are trichloromethyl, chlorodifluoromethyl, dichlorofluoromethyl, chloromethyl, bromomethyl, 1-fluoroethyl, 2-fluoroethyl, 2,2-difluoroethyl, 2,2,2-trifluoroethyl, 2,2,2-trichloroethyl, 2-chloro-2,2-difluoroethyl, pentafluoroethyl, 3,3,3-trifluoropropyl and pentafluoro-t-butyl. Preference is given to haloalkyl groups having 1 to 4 carbon atoms and 1 to 9, preferably 1 to 5, identical or different halogen atoms selected from fluorine, chlorine and bromine. Particular preference is given to haloalkyls having 1 or 2 carbon atoms and 1 to 5 identical or different halogen atoms selected from fluorine and chlorine, such as, inter alia, difluoromethyl, trifluoromethyl or 2,2-difluoroethyl. Further examples of compounds substituted by halogen are haloalkoxy such as $OCF_3$, $OCHF_2$, $OCH_2F$, $OCF_2CF_3$, $OCH_2CF_3$, $OCH_2CHF_2$ and $OCH_2CH_2Cl$, haloalkylsulfanyls such as difluoromethylthio, trifluoromethylthio, trichloromethylthio, chlorodifluoromethylthio, 1-fluoroethylthio, 2-fluoroethylthio, 2,2-difluoroethylthio, 1,1,2,2-tetrafluoroethylthio, 2,2,2-trifluoroethylthio or 2-chloro-1,1,2-trifluoroethylthio, haloalkylsulfinyls such as difluoromethylsulfinyl, trifluoromethylsulfinyl, trichloromethylsulfinyl, chlorodifluoromethylsulfinyl, 1-fluoroethylsulfinyl, 2-fluoroethylsulfinyl, 2,2-difluoroethylsulfinyl, 1,1,2,2-tetrafluoroethylsulfinyl, 2,2,2-trifluorethylsulfinyl and 2-chloro-1,1,2-trifluoroethylsulfinyl, haloalkylsulfinyls such as difluoromethylsulfinyl, trifluoromethylsulfinyl, trichloromethylsulfinyl, chlorodifluoromethylsulfinyl, 1-fluoroethylsulfinyl, 2-fluoroethylsulfinyl, 2,2-difluoroethylsulfinyl, 1,1,2,2-tetrafluoroethylsulfinyl, 2,2,2-trifluoroethylsulfinyl and 2-chloro-1,1,2-trifluoroethylsulfinyl, haloalkylsulfonyl groups such as difluoromethylsulfonyl, trifluoromethylsulfonyl, trichloromethylsulfonyl, chlorodifluoromethylsulfonyl, 1-fluoroethylsulfonyl, 2-fluoroethylsulfonyl, 2,2-difluoroethylsulfonyl, 1,1,2,2-tetrafluoroethylsulfonyl, 2,2,2-trifluoroethylsulfonyl and 2-chloro-1,1,2-trifluoroethylsulfonyl.

In the case of radicals having carbon atoms, preference is given to those having 1 to 4 carbon atoms, especially 1 or 2 carbon atoms. Preference is generally given to substituents from the group of halogen, for example fluorine and chlorine, $(C_1-C_4)$alkyl, preferably methyl or ethyl, $(C_1-C_4)$haloalkyl, preferably trifluoromethyl, $(C_1-C_4)$alkoxy, preferably methoxy or ethoxy, $(C_1-C_4)$haloalkoxy, nitro and cyano. Particular preference is given here to the substituents methyl, methoxy, fluorine and chlorine.

Substituted amino such as mono- or disubstituted amino is a radical from the group of the substituted amino radicals N-substituted, for example, by one or two identical or different radicals from the group of alkyl, hydroxyl, amino, alkoxy, acyl and aryl; preferably N-mono- and N,N-dialkylamino (e.g. methylamino, ethylamino, N,N-dimethylamino, N,N-diethylamino, N,N-di-n-propylamino, N,N-diisopropylamino or N,N-dibutylamino), N-mono- or N,N-dialkoxyalkylamino groups (e.g. N-methoxymethylamino, N-methoxyethylamino, N,N-di(methoxymethyl)amino or N,N-di(methoxyethyl)amino), N-mono- and N,N-diarylamino, such as optionally substituted anilines, acylamino, N,N-diacylamino, N-alkyl-N-arylamino, N-alkyl-N-acylamino and saturated N-heterocycles; preference is given to alkyl radicals having 1 to 4 carbon atoms; aryl is preferably phenyl or substituted phenyl; acyl is as defined further down, preferably $(C_1-C_4)$alkanoyl. The same applies to substituted hydroxylamino or hydrazino.

According to the invention, the term "cyclic amino groups" embraces heteroaromatic or aliphatic ring systems having one or more nitrogen atoms. The heterocycles are saturated or unsaturated, consist of one or more optionally fused ring systems and optionally include further heteroatoms, for example one or two nitrogen, oxygen and/or sulfur atoms. In addition, the term also embraces groups having a Spiro ring or a bridged ring system. The number of atoms which form the cyclic amino group is not limited and may be, for example, in the case of a one-ring system 3 to 8 ring atoms, and in the case of a two-ring system 7 to 11 atoms.

Examples of cyclic amino groups having saturated and unsaturated monocyclic groups having a nitrogen atom as heteroatom include 1-azetidinyl, pyrrolidino, 2-pyrrolidin-1-yl, 1-pyrrolyl, piperidino, 1,4-dihydropyrazin-1-yl, 1,2,5,6-tetrahydropyrazin-1-yl, 1,4-dihydropyridin-1-yl, 1,2,5,6-tetrahydropyridin-1-yl, homopiperidinyl; examples of cyclic amino groups having saturated and unsaturated monocyclic groups having two or more nitrogen atoms as heteroatoms include 1-imidazolidinyl, 1-imidazolyl, 1-pyrazolyl, 1-triazolyl, 1-tetrazolyl, 1-piperazinyl, 1-homopiperazinyl, 1,2-dihydropiperazin-1-yl, 1,2-dihydropyrimidin-1-yl, perhydropyrimidin-1-yl, 1,4-diazacycloheptan-1-yl; examples of cyclic amino groups having saturated and unsaturated monocyclic groups having one or two oxygen atoms and one to three nitrogen atoms as heteroatoms, for example oxazolidin-3-yl, 2,3-dihydroisoxazol-2-yl, isoxazol-2-yl, 1,2,3-oxadiazin-2-yl, morpholino, examples of cyclic amino groups having saturated and unsaturated monocyclic groups having one to three nitrogen atoms and one to two sulfur atoms as heteroatoms include thiazolidin-3-yl, isothiazolin-2-yl, thiomorpholino, or dioxothiomorpholino; examples of cyclic amino groups having saturated and unsaturated fused cyclic groups include indol-1-yl, 1,2-dihydrobenzimidazol-1-yl, perhydropyrrolo[1.2-a]pyrazin-2-yl; examples of cyclic amino groups having spirocyclic groups include 2-azaspiro[4.5]decan-2-yl; examples of cyclic amino groups having bridged heterocyclic groups include 2-azabicyclo[2.2.1]heptan-7-yl.

Substituted amino also includes quaternary ammonium compounds (salts) having four organic substituents on the nitrogen atom.

Optionally substituted phenyl is preferably phenyl which is unsubstituted or mono- or polysubstituted, preferably up to trisubstituted, by identical or different radicals from the group of halogen, $(C_1-C_4)$-alkyl, $(C_1-C_4)$-alkoxy, $(C_1-C_4)$-alkoxy-$(C_1-C_4)$-alkoxy, $(C_1-C_4)$-alkoxy-$(C_1-C_4)$-alkyl, $(C_1-C_4)$-haloalkyl, $(C_1-C_4)$-haloalkoxy, $(C_1-C_4)$-alkylsulfanyl, $(C_1-C_4)$-haloalkylsulfanyl, cyano, isocyano and nitro, for example o-, m- and p-tolyl, dimethylphenyls, 2-, 3- and 4-chlorophenyl, 2-, 3- and 4-fluorophenyl, 2-, 3- and 4-trifluoromethyl- and -trichloromethylphenyl, 2,4-, 3,5-, 2,5- and 2,3-dichlorophenyl, o-, m- and p-methoxyphenyl, 4-heptafluorophenyl.

Optionally substituted cycloalkyl is preferably cycloalkyl, which is unsubstituted or mono- or polysubstituted, preferably up to trisubstituted, by identical or different radicals from the group of halogen, cyano, $C_1$-$C_4$-alkyl, $C_1$-$C_4$-alkoxy, $C_1$-$C_4$-alkoxy-$C_1$-$C_4$-alkoxy, $C_1$-$C_4$-alkoxy-$C_1$-$C_4$-alkyl, $C_1$-$C_4$-haloalkyl and $C_1$-$C_4$-haloalkoxy, especially substituted by one or two $C_1$-$C_4$-alkyl radicals.

Optionally substituted heterocyclyl is preferably heterocyclyl which is unsubstituted or mono- or polysubstituted, preferably up to trisubstituted, by identical or different radicals from the group of halogen, cyano, $C_1$-$C_4$-alkyl, $C_1$-$C_4$-alkoxy, $C_1$-$C_4$-alkoxy-$C_1$-$C_4$-alkoxy, $C_1$-$C_4$-alkoxy-$C_1$-$C_4$-alkyl, $C_1$-$C_4$-haloalkyl, $C_1$-$C_4$-haloalkoxy, nitro and oxo, especially mono- or polysubstituted by radicals from the group of halogen, $C_1$-$C_4$-alkyl, $C_1$-$C_4$-alkoxy, $C_1$-$C_4$-haloalkyl and oxo, most preferably substituted by one or two $C_1$-$C_4$-alkyl radicals.

Examples of alkyl-substituted heteroaryl groups are furylmethyl, thienylmethyl, pyrazolylmethyl, imidazolylmethyl, 1,2,3- and 1,2,4-triazolylmethyl, isoxazolylmethyl, thiazolylmethyl, isothiazolylmethyl, 1,2,3-, 1,3,4-, 1,2,4- and 1,2,5-oxadiazolylmethyl, azepinylmethyl, pyrrolylmethyl, pyridylmethyl, pyridazinylmethyl, pyrimidinylmethyl, pyrazinylmethyl, 1,3,5-, 1,2,4- and 1,2,3-triazinylmethyl, 1,2,4-, 1,3,2-, 1,3,6- and 1,2,6-oxazinylmethyl, oxepinylmethyl, thiepinylmethyl and 1,2,4-di azepinylmethyl.

Inventive compounds may occur in preferred embodiments. Individual embodiments described herein may be combined with one another. Not included are combinations which contravene the laws of nature and which the person skilled in the art would therefore rule out on the basis of his/her expert knowledge. Ring structures having three or more adjacent oxygen atoms, for example, are excluded.

Isomers

Depending on the nature of the substituents, the compounds of the formula (I) may take the form of geometric and/or optically active isomers or corresponding isomer mixtures in different compositions. These stereoisomers are, for example, enantiomers, diastereomers, atropisomers or geometric isomers. The invention therefore encompasses pure stereoisomers and any desired mixtures of these isomers.

Methods and Uses

The invention also relates to methods for controlling animal pests, in which compounds of the formula (I) are allowed to act on animal pests and/or their habitat. The control of the animal pests is preferably carried out in agriculture and forestry, and in material protection. This preferably excludes methods for surgical or therapeutic treatment of the human or animal body and diagnostic methods carried out on the human or animal body.

The invention further relates to the use of the compounds of the formula (I) as pesticides, especially crop protection agents.

In the context of the present application, the term "pesticide" also always encompasses the term "crop protection agent".

The compounds of the formula (I), given good plant tolerance, favourable homeotherm toxicity and good environmental compatibility, are suitable for protecting plants and plant organs against biotic and abiotic stress factors, for increasing harvest yields, for improving the quality of the harvested material and for controlling animal pests, especially insects, arachnids, helminths, nematodes and molluscs, which are encountered in agriculture, in horticulture, in animal husbandry, in aquatic cultures, in forests, in gardens and leisure facilities, in the protection of stored products and of materials, and in the hygiene sector.

In the context of the present patent application, the term "hygiene" is understood as meaning the entirety of all measures, processes and procedures whose aim it is to prevent disorders—in particular infective diseases—and to serve to keep humans, animals and/or the environment healthy and/or to maintain cleanliness. According to the invention, this includes in particular measures for cleaning, disinfecting and sterilizing, for example, textiles or hard surfaces, mainly made of glass, wood, concrete, porcelain, ceramic, plastic or else of metal(s), and keeping them clean of hygiene pests and/or their faeces. Excluded according to the invention are in this respect again processes for the surgical or therapeutic treatment of the human or animal body and diagnostic processes undertaken on the human or animal body.

The term "hygiene sector" thus includes all areas, technical fields and commercial utilizations in which such hygiene measures, processes and procedures are of importance, for example hygiene in kitchens, bakeries, airports, baths, swimming pools, shopping centres, hotels, hospitals, stables, etc.

Accordingly, the term "hygiene pest" is understood as meaning one or more animal pests whose presence in the hygiene sector is problematic, in particular for health reasons. Accordingly, the main aim is to minimize or prevent hygiene pests or contact therewith in the hygiene sector. This can be effected, in particular, by using a pesticide, where the agent can be employed both prophylactically and only in the case of infestation to control the pest. It is also possible to use agents which act by avoiding or reducing contact with the pest. Hygiene pests are, for example, the organisms mentioned below.

Thus, the term "hygiene protection" includes all actions which serve to maintain and/or improve such hygiene measures, processes and procedures.

The compounds of the formula (I) can preferably be used as pesticides. They are active against normally sensitive and resistant species and also against all or specific stages of development. The abovementioned pests include:

Pests from the phylum of the Arthropoda, especially from the class of the Arachnida, for example *Acarus* spp., for example *Acarus siro*, *Aceria kuko*, *Aceria sheldoni*, *Aculops* spp., *Aculus* spp., for example *Aculus fockeui*, *Aculus schlechtendali*, *Amblyomma* spp., *Amphitetranychus viennensis*, *Argas* spp., *Boophilus* spp., *Brevipalpus* spp., for example *Brevipalpus phoenicis*, *Bryobia graminum*, *Bryobia praetiosa*, *Centruroides* spp., Chorioptes spp., *Dermanyssus gallinae*, *Dermatophagoides pteronyssinus*, *Dermatophagoides farinae*, *Dermacentor* spp., *Eotetranychus* spp., for example *Eotetranychus hicoriae*, *Epitrimerus pyri*, *Eutetranychus* spp., for example *Eutetranychus banksi*, *Eriophyes* spp., for example *Eriophyes pyri*, *Glycyphagus domesticus*, *Halotydeus destructor*, *Hemitarsonemus* spp., for example *Hemitarsonemus latus* (=*Polyphagotarsonemus latus*), *Hyalomma* spp., *Ixodes* spp., *Latrodectus* spp., *Loxosceles* spp., *Neutrombicula autumnalis*, *Nuphersa* spp., *Oligonychus* spp., for example *Oligonychus coffeae*, *Oligonychus coniferarum*, *Oligonychus ilicis*, *Oligonychus indicus*, *Oligonychus mangiferus*, *Oligonychus pratensis*, *Oligonychus punicae*, *Oligonychus yothersi*, *Ornithodorus* spp., *Ornithonyssus* spp., *Panonychus* spp., for example *Panonychus citri* (=*Metatetranychus citri*), *Panonychus ulmi* (=*Metatetranychus ulmi*), *Phyllocoptruta oleivora*, *Platytetranychus multidigituli*, *Polyphagotarsonemus latus*, *Psoroptes* spp., *Rhipicephalus* spp., *Rhizoglyphus* spp., *Sarcoptes* spp., *Scorpio maurus*, *Steneotarsonemus* spp., *Steneotarsonemus spinki*, *Tarsonemus* spp., for example *Tarsonemus confusus*, *Tarsonemus pallidus*, *Tetranychus* spp., for example *Tetranychus canadensis*, *Tetranychus cinna-*

*barinus, Tetranychus turkestani, Tetranychus urticae, Trombicula alfreddugesi, Vaejovis* spp., *Vasates lycopersici;* from the class of the Chilopoda, for example *Geophilus* spp., *Scutigera* spp.;

from the order or the class of the Collembola, for example *Onychiurus armatus;* Sminthurus *viridis;* from the class of the Diplopoda, for example *Blaniulus guttulatus;* from the class of the Insecta, for example from the order of the Blattodea, for example *Blatta orientalis, Blattella asahinai, Blattella germanica, Leucophaea maderae, Loboptera decipiens, Neostylopyga rhombifolia, Panchlora* spp., *Parcoblatta* spp., *Periplaneta* spp., for example *Periplaneta americana, Periplaneta australasiae, Pycnoscelus surinamensis, Supella longipalpa;* from the order of the Coleoptera, for example *Acalymma vittatum, Acanthoscelides obtectus, Adoretus* spp., *Aethina tumida, Agelastica alni, Agriotes* spp., for example *Agriotes linneatus, Agriotes mancus, Alphitobius diaperinus, Amphimallon solstitialis, Anobium punctatum, Anoplophora* spp., *Anthonomus* spp., for example *Anthonomus grandis, Anthrenus* spp., *Apion* spp., *Apogonia* spp., *Atomaria* spp., for example *Atomaria linearis, Attagenus* spp., *Buis caerulescens, Bruchidius obtectus, Bruchus* spp., for example *Bruchus pisorum, Bruchus rufimanus, Cassida* spp., *Cerotoma trifurcata, Ceutorrhynchus* spp., for example *Ceutorrhynchus assimilis, Ceutorrhynchus quadridens, Ceutorrhynchus rapae, Chaetocnema* spp., for example *Chaetocnema confinis, Chaetocnema denticulata, Chaetocnema ectypa, Cleonus mendicus, Conoderus* spp., *Cosmopolites* spp., for example *Cosmopolites sordidus, Costelytra zealandica, Ctenicera* spp., *Curculio* spp., for example *Curculio caryae, Curculio caryatrypes, Curculio obtusus, Curculio sayi, Cryptolestes ferrugineus, Cryptolestes pusillus, Cryptorhynchus lapathi, Cryptorhynchus mangiferae, Cylindrocopturus* spp., *Cylindrocopturus adspersus, Cylindrocopturus furnissi, Dermestes* spp., *Diabrotica* spp., for example *Diabrotica balteata, Diabrotica barberi, Diabrotica undecimpunctata howardi, Diabrotica undecimpunctata undecimpunctata, Diabrotica virgifera virgifera, Diabrotica virgifera zeae, Dichocrocis* spp., *Dicladispa armigera, Diloboderus* spp., *Epicaerus* spp., *Epilachna* spp., for example *Epilachna borealis, Epilachna varivestis, Epitrix* spp., for example *Epitrix cucumeris, Epitrix fuscula, Epitrix hirtipennis, Epitrix subcrinita, Epitrix tuberis, Faustinus* spp., *Gibbium psylloides, Gnathocerus cornutus, Hellula undalis, Heteronychus arator, Heteronyx* spp., *Hylamorpha elegans, Hylotrupes bajulus, Hypera postica, Hypomeces squamosus, Hypothenemus* spp., for example *Hypothenemus hampei, Hypothenemus obscurus, Hypothenemus pubescens, Lachnosterna consanguinea, Lasioderma serricorne, Latheticus oryzae, Lathridius* spp., *Lema* spp., *Leptinotarsa decemlineata, Leucoptera* spp., for example *Leucoptera coffeella, Lissorhoptrus oryzophilus, Listronotus (=Hyperodes)* spp., *Lixus* spp., *Luperodes* spp., *Luperomorpha xanthodera, Lyctus* spp., *Megascelis* spp., *Melanotus* spp., for example *Melanotus longulus oregonensis, Meligethes aeneus, Melolontha* spp., for example *Melolontha melolontha, Migdolus* spp., *Monochamus* spp., *Naupactus xanthographus, Necrobia* spp., *Neogalerucella* spp., *Niptus hololeucus, Oryctes rhinoceros, Oryzaephilus surinamensis, Oryzaphagus oryzae, Otiorhynchus* spp., for example *Otiorhynchus cribricollis, Otiorhynchus ligustici, Otiorhynchus ovatus, Otiorhynchus rugosostriarus, Otiorhynchus sulcatus, Oulema* spp., for example *Oulema melanopus, Oulema oryzae, Oxycetonia jucunda, Phaedon cochleariae, Phyllophaga* spp., *Phyllophaga helleri, Phyllotreta* spp., for example *Phyllotreta armoraciae, Phyllotreta pusilla, Phyllotreta ramosa, Phyllotreta striolata, Popillia japonica, Premnotrypes* spp., *Prostephanus truncatus, Psylliodes* spp., for example *Psylliodes affinis, Psylliodes chrysocephala, Psylliodes punctulata, Ptinus* spp., *Rhizobius ventralis, Rhizopertha dominica, Rhynchophorus* spp., *Rhynchophorus ferrugineus, Rhynchophorus palmarum, Sinoxylon perforans, Sitophilus* spp., for example *Sitophilus granarius, Sitophilus linearis, Sitophilus oryzae, Sitophilus zeamais, Sphenophorus* spp., *Stegobium paniceum, Sternechus* spp., for example *Sternechus paludatus, Symphyletes* spp., *Tanymecus* spp., for example *Tanymecus dilaticollis, Tanymecus indicus, Tanymecus palliatus, Tenebrio molitor, Tenebrioides mauretanicus, Tribolium* spp., for example *Tribolium audax, Tribolium castaneum, Tribolium confusum, Trogoderma* spp., *Tychius* spp., *Xylotrechus* spp., *Zabrus* spp., for example *Zabrus tenebrioides;* from the order of the Dermaptera, for example *Anisolabis maritime, Forficula auricularia, Labidura riparia;* from the order of the Diptera, for example *Aedes* spp., for example *Aedes aegypti, Aedes albopictus, Aedes sticticus, Aedes vexans, Agromyza* spp., for example *Agromyza frontella, Agromyza parvicornis, Anastrepha* spp., *Anopheles* spp., for example *Anopheles quadrimaculatus, Anopheles gambiae, Asphondylia* spp., *Bactrocera* spp., for example *Bactrocera cucurbitae, Bactrocera dorsalis, Bactrocera oleae, Bibio hortulanus, Calliphora erythrocephala, Calliphora vicina, Ceratitis capitata, Chironomus* spp., *Chrysomya* spp., *Chrysops* spp., *Chrysozona pluvialis, Cochliomya* spp., *Contarinia* spp., for example *Contarinia johnsoni, Contarinia nasturtii, Contarinia pyrivora, Contarinia schulzi, Contarinia sorghicola, Contarinia tritici, Cordylobia anthropophaga, Cricotopus sylvestris, Culex* spp., for example *Culex pipiens, Culex quinquefasciatus, Culicoides* spp., *Culiseta* spp., *Cuterebra* spp., *Dacus oleae, Dasineura* spp., for example *Dasineura brassicae, Delia* spp., for example *Delia antiqua, Delia coarctata, Delia florilega, Delia platura, Delia radicum, Dermatobia hominis, Drosophila* spp., for example *Drosphila melanogaster, Drosophila suzukii, Echinocnemus* spp., *Euleia heraclei, Fannia* spp., *Gasterophilus* spp., *Glossina* spp., *Haematopota* spp., *Hydrellia* spp., *Hydrellia griseola, Hylemya* spp., *Hippobosca* spp., *Hypoderma* spp., *Liriomyza* spp., for example *Liriomyza brassicae, Liriomyza huidobrensis, Liriomyza sativae, Lucilia* spp., for example *Lucilia cuprina, Lutzomyia* spp., *Mansonia* spp., *Musca* spp., for example *Musca domestica, Musca domestica vicina, Oestrus* spp., *Oscinella frit, Paratanytarsus* spp., *Paralauterborniella subcincta, Pegomya* or *Pegomyia* spp., for example *Pegomya betae, Pegomya hyoscyami, Pegomya rubivora, Phlebotomus* spp., *Phorbia* spp., *Phormia* spp., *Piophila casei, Platyparea poeciloptera, Prodiplosis* spp., *Psila rosae, Rhagoletis* spp., for example *Rhagoletis cingulata, Rhagoletis completa, Rhagoletis fausta, Rhagoletis indifferens, Rhagoletis mendax, Rhagoletis pomonella, Sarcophaga* spp., *Simulium* spp., for example *Simulium meridionale, Stomoxys* spp., *Tabanus* spp., *Tetanops* spp., Tipula spp., for example Tipula paludosa, Tipula simplex, Toxotrypana curvicauda;

from the order of the Hemiptera for example Acizzia acaciaebaileyanae, Acizzia dodonaeae, Acizzia uncatoides, Acrida turrita, Acyrthosiphon spp., for example Acyrthosiphon pisum, Acrogonia spp., Aeneolamia spp., Agonoscena spp., Aleurocanthus spp., Aleyrodes proletella, Aleurolobus barodensis, Aleurothrixus floccosus, Allocaridara malayensis, Amrasca spp., for example Amrasca bigutulla, Amrasca devastans, Anuraphis cardui, Aonidiella spp., for example Aonidiella aurantii, Aonidiella citrina, Aonidiella inornata, Aphanostigma piri, Aphis spp., for example Aphis citricola, Aphis craccivora, Aphis fabae, Aphis forbesi, Aphis glycines, Aphis gossypii, Aphis hederae, Aphis illinoisensis, Aphis middletoni, Aphis nasturtii, Aphis nerii, Aphis pomi, Aphis spiraecola, Aphis viburniphila, Arboridia apicalis, Arytainilla spp., Aspidiella spp., Aspidiotus spp., for example Aspidiotus nerii, Atanus spp., Aulacorthum solani, Bemisia tabaci, Blastopsylla occidentalis, Boreioglycaspis melaleucae, Brachycaudus helichrysi, Brachycolus spp., Brevicoryne brassicae, Cacopsylla spp., for example Cacopsylla pyricola, Calligypona marginata, Capulinia spp., Carneocephala fulgida, Ceratovacuna lanigera, Cercopidae, Ceroplastes spp., Chaetosiphon fragaefolii, Chionaspis tegalensis, Chlorita onukii, Chondracris rosea, Chromaphis juglandicola, Chrysomphalus aonidum, Chrysomphalus ficus, Cicadulina mbila, Coccomytilus halli, Coccus spp., for example Coccus hesperidum, Coccus longulus, Coccus pseudomagnoliarum, Coccus viridis, Cryptomyzus ribis, Cryptoneossa spp., Ctenarytaina spp., Dalbulus spp., Dialeurodes chittendeni, Dialeurodes citri, Diaphorina citri, Diaspis spp., Diuraphis spp., Doralis spp., Drosicha spp., Dysaphis spp., for example Dysaphis apiifolia, Dysaphis plantaginea, Dysaphis tulipae, Dysmicoccus spp., Empoasca spp., for example Empoasca abrupta, Empoasca fabae, Empoasca maligna, Empoasca solana, Empoasca stevensi, Eriosoma spp., for example Eriosoma americanum, Eriosoma lanigerum, Eriosoma pyricola, Erythroneura spp., Eucalyptolyma spp., Euphyllura spp., Euscelis bilobatus, Ferrisia spp., Fiorinia spp., Furcaspis oceanica, Geococcus coffeae, Glycaspis spp., Heteropsylla cubana, Heteropsylla spinulosa, Homalodisca coagulata, Hyalopterus arundinis, Hyalopterus pruni, Icerya spp., for example Icerya purchasi, Idiocerus spp., Idioscopus spp., Laodelphax striatellus, Lecanium spp., for example Lecanium corni (=Parthenolecanium corni), Lepidosaphes spp., for example Lepidosaphes ulmi, Lipaphis erysimi, Lopholeucaspis japonica, Lycorma delicatula, Macrosiphum spp., for example Macrosiphum euphorbiae, Macrosiphum lilii, Macrosiphum rosae, Macrosteles facifrons, Mahanarva spp., Melanaphis sacchari, Metcalfiella spp., Metcalfa pruinosa, Metopolophium dirhodum, Monellia costalis, Monelliopsis pecanis, Myzus spp., for example Myzus ascalonicus, Myzus cerasi, Myzus ligustri, Myzus ornatus, Myzus persicae, Myzus nicotianae, Nasonovia ribisnigri, Neomaskellia spp., Nephotettix spp., for example Nephotettix cincticeps, Nephotettix nigropictus, Nettigoniclla spectra, Nilaparvata lugens, Oncometopia spp., Orthezia praelonga, Oxya chinensis, Pachypsylla spp., Parabemisia myricae, Paratrioza spp., for example Paratrioza cockerelli, Parlatoria spp., Pemphigus spp., for example Pemphigus bursarius, Pemphigus populivenae, Peregrinus maidis, Perkinsiella spp., Phenacoccus spp., for example Phenacoccus madeirensis, Phloeomyzus passerinii, Phorodon humuli, Phylloxera spp., for example Phylloxera devastatrix, Phylloxera notabilis, Pinnaspis aspidistrae, Planococcus spp., for example Planococcus citri, Prosopidopsylla flava, Protopulvinaria pyriformis, Pseudaulacaspis pentagona, Pseudococcus spp., for example Pseudococcus calceolariae, Pseudococcus comstocki, Pseudococcus longispinus, Pseudococcus maritimus, Pseudococcus viburni, Psyllopsis spp., Psylla spp., for example Psylla buxi, Psylla mali, Psylla pyri, Pteromalus spp., Pulvinaria spp., Pyrilla spp., Quadraspidiotus spp., for example Quadraspidiotus juglansregiae, Quadraspidiotus ostreaeformis, Quadraspidiotus perniciosus, Quesada gigas, Rastrococcus spp., Rhopalosiphum spp., for example Rhopalosiphum maidis, Rhopalosiphum oxyacanthae, Rhopalosiphum padi, Rhopalosiphum rufiabdominale, Saissetia spp., for example Saissetia coffeae, Saissetia miranda, Saissetia neglecta, Saissetia oleae, Scaphoideus titanus, Schizaphis graminum, Selenaspidus articulatus, Sipha flava, Sitobion avenae, Sogata spp., Sogatella furcifera, Sogatodes spp., Stictocephala festina, Siphoninus phillyreae, Tenalaphara malayensis, Tetragonocephela spp., Tinocallis caryaefoliae, Tomaspis spp., Toxoptera spp., for example Toxoptera aurantii, Toxoptera citricidus, Trialeurodes vaporariorum, Trioza spp., for example Trioza diospyri, Typhlocyba spp., Unaspis spp., Viteus vitifolii, Zygina spp.;

from the suborder of the Heteroptera, for example Aelia spp., Anasa tristis, Antestiopsis spp., Boisea spp., Blissus spp., Calocoris spp., Campylomma livida, Cavelerius spp., Cimex spp., for example Cimex adjunctus, Cimex hemipterus, Cimex lectularius, Cimex pilosellus, Collaria spp., Creontiades dilutus, Dasynus piperis, Dichelops furcatus, Diconocoris hewetti, Dysdercus spp., Euschistus spp., for example Euschistus heros, Euschistus servus, Euschistus tristigmus, Euschistus variolarius, Eurydema spp., Eurygaster spp., Halyomorpha halys, Heliopeltis spp., Horcias nobilellus, Leptocorisa spp., Leptocorisa varicornis, Leptoglossus occidentalis, Leptoglossus phyllopus, Lygocoris spp., for example Lygocoris pabulinus, Lygus spp., for example Lygus elisus, Lygus hesperus, Lygus lineolaris, Macropes excavatus, Megacopta cribraria, Miridae, Monalonion atratum, Nezara spp., for example Nezara viridula, Nysius spp., Oebalus spp., Pentomidae, Piesma quadrata, Piezodorus spp., for example Piezodorus guildinii, Psallus spp., Pseudacysta persea, Rhodnius spp., Sahlbergella singularis, Scaptocoris castanea, Scotinophora spp., Stephanitis nashi, Tibraca spp., Triatoma spp.;

from the order of the Hymenoptera, for example Acromyrmex spp., Athalia spp., for example Athalia rosae, Atta spp., Camponotus spp., Dolichovespula spp., Diprion spp., for example Diprion similis, Hoplocampa spp., for example Hoplocampa cookei, Hoplocampa testudinea, Lasius spp., Linepithema (Iridiomyrmex) humile, Monomorium pharaonis, Paratrechina spp., Paravespula spp., Plagiolepis spp., Sirex spp., Solenopsis invicta, Tapinoma spp., Technomyrmex albipes, Urocerus spp., Vespa spp., for example Vespa crabro, Wasmannia auropunctata, Xeris spp.;

from the order of the Isopoda, for example Armadillidium vulgare, Oniscus asellus, Porcellio scaber;

from the order of the Isoptera, for example Coptotermes spp., for example Coptotermes formosanus, Cornitermes cumulans, Cryptotermes spp., Incisitermes spp., Kalotermes spp., Microtermes obesi, Nasutitermes spp., Odontotermes spp., Porotermes spp., Reticulitermes spp., for example Reticulitermes flavipes, Reticulitermes hesperus;

from the order of the Lepidoptera, for example Achroia grisella, Acronicta major, Adoxophyes spp., for example Adoxophyes orana, Aedia leucomelas, Agrotis spp., for example Agrotis segetum, Agrotis ipsilon, Alabama spp., for example Alabama argillacea, Amyelois transitella, Anarsia spp., Anticarsia spp., for example Anticarsia gemmatalis, Argyroploce spp., Autographa spp., Barathra brassicae, Blastodacna atra, Borbo cinnara, Bucculatrix thurberiella, Bupalus piniarius, Busseola spp., Cacoecia spp., Caloptilia theivora, Capua reticulana, Carpocapsa pomonella, Carposina niponensis, Cheimatobia brumata, Chilo spp., for example Chilo plejadellus, Chilo suppressalis, Choreutis pariana, Choristoneura spp., Chrysodeixis chalcites, Clysia ambiguella, Cnaphalocerus spp., Cnaphalocrocis medinalis, Cnephasia spp., Conopomorpha spp., Conotrachelus spp., Copitarsia spp., Cydia spp., for example Cydia nigricana, Cydia pomonella, Dalaca noctuides, Diaphania spp., Diparopsis spp., Diatraea saccharalis, Earias spp., Ecdytolopha aurantium, Elasmopalpus lignosellus, Eldana saccharina, Ephestia spp., for example Ephestia elutella, Ephestia kuehniella, Epinotia spp., Epiphyas postvittana, Erannis spp., Erschoviella musculana, Etiella spp., Eudocima spp., Eulia spp., Eupoecilia ambiguella, Euproctis spp., for example Euproctis chrysorrhoea, Euxoa spp., Feltia spp., Galleria mellonella, Gracillaria spp., Grapholitha spp., for example Grapholita molesta, Grapholita prunivora, Hedylepta spp., Helicoverpa spp., for example Helicoverpa armigera, Helicoverpa zea, Heliothis spp., for example Heliothis virescens, Hofmannophila pseudospretella, Homoeosoma spp., Homona spp., Hyponomeuta padella, Kakivoria flavofasciata, Lampides spp., Laphygma spp., Laspeyresia molesta, Leucinodes orbonalis, Leucoptera spp., for example Leucoptera coffeella, Lithocolletis spp., for example Lithocolletis blancardella, Lithophane antennata, Lobesia spp., for example Lobesia botrana, Loxagrotis albicosta, Lymantria spp., for example Lymantria dispar, Lyonetia spp., for example Lyonetia clerkella, Malacosoma neustria, Maruca testulalis, Mamestra brassicae, Melanitis leda, Mocis spp., Monopis obviella, Mythimna separata, Nemapogon cloacellus, Nymphula spp., Oiketicus spp., Omphisa spp., Operophtera spp., Oria spp., Orthaga spp., Ostrinia spp., for example Ostrinia nubilalis, Panolis flammea, Parnara spp., Pectinophora spp., for example Pectinophora gossypiella, Perileucoptera spp., Phthorimaea spp., for example Phthorimaea operculella, Phyllocnistis citrella, Phyllonorycter spp., for example Phyllonorycter blancardella, Phyllonorycter crataegella, Pieris spp., for example Pieris rapae, Platynota stultana, Plodia interpunctella, Plusia spp., Plutella xylostella (=Plutella maculipennis), Prays spp., Prodenia spp., Protoparce spp., Pseudaletia spp., for example Pseudaletia unipuncta, Pseudoplusia includens, Pyrausta nubilalis, Rachiplusia nu, Schoenobius spp., for example Schoenobius bipunctifer, Scirpophaga spp., for example Scirpophaga innotata, Scotia segetum, Sesamia spp., for example Sesamia inferens, Sparganothis spp., Spodoptera spp., for example Spodoptera eradiana, Spodoptera exigua, Spodoptera frugiperda, Spodoptera praefica, Stathmopoda spp., Stenoma spp., Stomopteryx subsecivella, Synanthedon spp., Tecia solanivora, Thaumetopoea spp., Thermesia gemmatalis, Tinea cloacella, Tinea pellionella, Tineola bisselliella, Tortrix spp., Trichophaga tapetzella, Trichoplusia spp., for example Trichoplusia ni, Tryporyza incertulas, Tuta absoluta, Virachola spp.;

from the order of the Orthoptera or Saltatoria, for example Acheta domesticus, Dichroplus spp., Gryllotalpa spp., for example Gryllotalpa gryllotalpa, Hieroglyphus spp., Locusta spp., for example Locusta migratoria, Melanoplus spp., for example Melanoplus devastator, Paratlanticus ussuriensis, Schistocerca gregaria;

from the order of the Phthiraptera, for example Damalinia spp., Haematopinus spp., Linognathus spp., Pediculus spp., Phylloxera vastatrix, Phthirus pubis, Trichodectes spp.;

from the order of the Psocoptera, for example Lepinotus spp., Liposcelis spp.;

from the order of the Siphonaptera, for example Ceratophyllus spp., Ctenocephalides spp., for example Ctenocephalides canis, Ctenocephalides felis, Pulex irritans, Tunga penetrans, Xenopsylla cheopis;

from the order of the Thysanoptera, for example Anaphothrips obscurus, Baliothrips biformis, Chaetanaphothrips leeuweni, Drepanothrips reuteri, Enneothrips flavens, Frankliniella spp., for example Frankliniella fusca, Frankliniella occidentalis, Frankliniella schultzei, Frankliniella tritici, Frankliniella vaccinii, Frankliniella williamsi, Haplothrips spp., Heliothrips spp., Hercinothrips femoralis, Kakothrips spp., Rhipiphorothrips cruentatus, Scirtothrips spp., Taeniothrips cardamomi, Thrips spp., for example Thrips palmi, Thrips tabaci;

from the order of the Zygentoma (=Thysanura), for example Ctenolepisma spp., Lepisma saccharina, Lepismodes inquilinus, Thermobia domestica;

from the class of the Symphyla, for example Scutigerella spp., for example Scutigerella immaculata; pests from the phylum of the Mollusca, in particular from the class of the Bivalvia, for example Dreissena spp;

and also from the class of the Gastropoda, for example Arion spp., for example Arion ater rufus, Biomphalaria spp., Bulinus spp., Deroceras spp., for example Deroceras laeve, Galba spp., Lymnaea spp., Oncomelania spp., Pomacea spp., Succinea spp.;

Animal and human parasites from the phyla of the Platyhelminthes and Nematoda, for example Aelurostrongylus spp., Amidostomum spp., Ancylostoma spp, for example Ancylostoma duodenale, Ancylostoma ceylanicum, Acylostoma braziliensis, Angiostrongylus spp., Anisakis spp., Anoplocephala spp., Ascaris spp., Ascaridia spp., Baylisascaris spp., Brugia spp., for example Brugia malayi, Brugia timori, Bunostomum spp., Capillaria spp., Chabertia spp., Clonorchis spp., Cooperia spp., Crenosoma spp., Cyathostoma spp., Dicrocoelium spp., Dictyocaulus spp., for example Dictyocaulus filaria, Diphyllobothrium spp., for example Diphyllobothrium latum, Dipylidium spp., Dirofilaria spp., Dracunculus spp., for example Dracunculus medinensis, Echinococcus spp., for example Echinococcus granulosus, Echinococcus multilocularis, Echinostoma spp., Enterobius spp., for example Enterobius vermicularis, Eucoleus spp., Fasciola spp., Fascioloides spp., Fasciolopsis spp., Filaroides spp., Gongylonema spp., Gyrodactylus spp., Habronema spp., Haemonchus spp., Heligmosomoides spp., Heterakis spp., Hymenolepis spp., for example Hyme-

*nolepis nana*, Hyostrongylus spp., Litomosoides spp., *Loa* spp., for example *Loa Loa, Metastrongylus* spp., *Metorchis* spp., *Mesocestoides* spp., *Moniezia* spp., Muellerius spp., *Necator* spp., Nematodirus spp., Nippostrongylus spp., Oesophagostomum spp., Ollulanus spp., Onchocerca spp., for example Onchocerca *volvulus, Opisthorchis* spp., Oslerus spp., Ostertagia spp., *Oxyuris* spp., Paracapillaria spp., Parafilaria spp., Paragonimus spp., *Paramphistomum* spp., Paranoplocephala spp., Parascaris spp., Passalurus spp., Protostrongylus spp., *Schistosoma* spp., *Setaria* spp., Spirocerca spp., Stephanofilaria spp., *Stephanurus* spp., *Strongyloides* spp., for example *Strongyloides fuelleborni, Strongyloides stercoralis, Strongylus* spp., Syngamus spp., *Taenia* spp., for example *Taenia saginata, Taenia solium*, Teladorsagia spp., Thelazia spp., Toxascaris spp., Toxocara spp., Trichinella spp., for example Trichinella *spiralis*, Trichinella *nativa*, Trichinella *britovi*, Trichinella *nelsoni*, Trichinella *pseudopsiralis, Trichobilharzia* spp., Trichostrongylus spp., Trichuris spp., for example Trichuris *trichiura, Uncinaria* spp., Wuchereria spp., for example Wuchereria *bancrofti;*

Plant pests from the phylum of the Nematoda, i.e. plant-parasitic nematodes, in particular Aglenchus spp., for example Aglenchus *agricola, Anguina* spp., for example *Anguina tritici*, Aphelenchoides spp., for example Aphelenchoides *arachidis*, Aphelenchoides *fragariae*, Belonolaimus spp., for example Belonolaimus *gracilis*, Belonolaimus *longicaudatus*, Belonolaimus *nortoni*, Bursaphelenchus spp., for example Bursaphelenchus *cocophilus*, Bursaphelenchus *eremus*, Bursaphelenchus *xylophilus*, Cacopaurus spp., for example Cacopaurus *pestis*, Criconemella spp., for example Criconemella *curvata*, Criconemella *onoensis*, Criconemella *ornata*, Criconemella *rusium*, Criconemella xenoplax (=*Mesocriconema xenoplax*), Criconemoides spp., for example Criconemoides *ferniae*, Criconemoides *onoense*, Criconemoides *ornatum*, Ditylenchus spp., for example Ditylenchus *dipsaci*, Dolichodorus spp., Globodera spp., for example Globodera *pallida*, Globodera *rostochiensis*, Helicotylenchus spp., for example Helicotylenchus dihystera, Hemicriconemoides spp., Hemicycliophora spp., *Heterodera* spp., for example *Heterodera avenae, Heterodera glycines, Heterodera schachtii, Hirschmaniella* spp., Hoplolaimus spp., Longidorus spp., for example Longidorus *africanus*, Meloidogyne spp., for example Meloidogyne chitwoodi, Meloidogyne *fallax*, Meloidogyne *hapla*, Meloidogyne *incognita*, Meloinema spp., Nacobbus spp., Neotylenchus spp., Paralongidorus spp., Paraphelenchus spp., Paratrichodorus spp., for example Paratrichodorus *minor*, Paratylenchus spp., Pratylenchus spp., for example Pratylenchus *penetrans*, Pseudohalenchus spp., Psilenchus spp., Punctodera spp., Quinisulcius spp., Radopholus spp., for example Radopholus *citrophilus*, Radopholus *similis*, Rotylenchulus spp., Rotylenchus spp., Scutellonema spp., Subanguina spp., Trichodorus spp., for example Trichodorus *obtusus*, Trichodorus *primitivus*, Tylenchorhynchus spp., for example Tylenchorhynchus *annulatus*, Tylenchulus spp., for example Tylenchulus *semipenetrans*, Xiphinema spp., for example Xiphinema *index*.

In addition, it is possible to control, from the sub-kingdom of the Protozoa, the order of the Coccidia, for example Eimeria spp.

Nematodes

In the present context, the term "nematodes" comprises all species of the phylum Nematoda and here in particular species that act as parasites on plants or fungi (for example species of the order Aphelenchida, Meloidogyne, Tylenchida and others) or else on humans and animals (for example species of the orders Trichinellida, Tylenchida, Rhabditida and Spirurida) or cause damage in or on these living organisms, and also other parasitic helminths.

A nematicide in crop protection, as described herein, is capable of controlling nematodes.

The term "controlling nematodes" means killing the nematodes or preventing or impeding their development or their growth or preventing or impeding their penetration into or their sucking on plant tissue.

Here, the efficacy of the compounds is determined by comparing mortalities, gall formation, cyst formation, nematode density per volume of soil, nematode density per root, number of nematode eggs per volume of soil, mobility of the nematodes between a plant or plant part treated with the compound of the formula (I) or the treated soil and an untreated plant or plant part or the untreated soil (100%). Preferably, the reduction achieved is 25-50% in comparison to an untreated plant, plant part or the untreated soil, more preferably 51-79% and most preferably the complete eradication or the complete prevention of development and growth of the nematodes by a reduction of 80 to 100% is achieved. The control of nematodes as described herein also comprises the control of proliferation of the nematodes (development of cysts and/or eggs). Compounds of the formula (I) can also be used to keep the plants or animals healthy, and they can be employed curatively, preventatively or systemically for the control of nematodes.

The person skilled in the art knows methods for determining mortalities, gall formation, cyst formation, nematode density per volume of soil, nematode density per root, number of nematode eggs per volume of soil, mobility of the nematodes.

The use of a compound of the formula (I) may keep the plant healthy and also comprises a reduction of the damage caused by nematodes and an increase of the harvest yield.

In the present context, the term "nematodes" refers to plant nematodes which comprise all nematodes which damage plants. Plant nematodes comprise phytoparasitic nematodes and soil-borne nematodes. The phytoparasitic nematodes include ectoparasites such as Xiphinema spp., Longidorus spp. and Trichodorus spp.; semiparasites such as Tylenchulus spp.; migratory endoparasites such as Pratylenchus spp., Radopholus spp. and Scutellonema spp.; non-migratory parasites such as *Heterodera* spp., Globodera spp. and Meloidogyne spp., and also stem and leaf endoparasites such as Ditylenchus spp., Aphelenchoides spp. and Hirschmaniella spp. Particularly damaging root-parasitic soil nematodes are, for example, cyst-forming nematodes of the genera *Heterodera* or Globodera, and/or root gall nematodes of the genus Meloidogyne. Damaging species of these genera are, for example, Meloidogyne *incognita, Heterodera glycines* (soya bean cyst nematode), Globodera *pallida* and Globodera *rostochiensis* (potato cyst nematode), these species being controlled effectively by the compounds described in the present text. However, the use of the compounds described in the present text is by no means restricted to these genera or species, but also extends in the same manner to other nematodes.

The plant nematodes include, for example, Aglenchus *agricola, Anguina tritici*, Aphelenchoides *arachidis*, Aphelenchoides *fragaria*, and the stem and leaf endoparasites Aphelenchoides spp., Belonolaimus *gracilis*, Belonolaimus *longicaudatus*, Belonolaimus *nortoni*, Bursaphelenchus *cocophilus*, Bursaphelenchus *eremus*, Bursaphelenchus *xylophilus* and Bursaphelenchus spp., Cacopaurus *pestis*, Criconemella *curvata*, Criconemella *onoensis*, Criconemella *ornata*, Criconemella *rusium*, Criconemella *xenoplax* (=Mesocriconema xenoplax) and Criconemella spp., Criconemoides ferniae, Criconemoides *onoense*, Criconemoides *ornatum* and Criconemoides spp., Ditylenchus *destructor*, Ditylenchus *dipsaci*, Ditylenchus myceliophagus and also the stem and leaf endoparasites Ditylenchus spp., Dolichodorus *heterocephalus*, Globodera *pallida* (=*Heterodera pallida*), Globodera *rostochiensis* (potato cyst nematode), Globodera *solanacearum*, Globodera *tabacum*, Globodera *virginia* and the non-migratory cyst-forming parasites Globodera spp., Helicotylenchus digonicus, Helicotylenchus dihystera, Helicotylenchus erythrine, Helicotylenchus *multicinctus*, Helicotylenchus nannus, Helicotylenchus pseudorobustus and Helicotylenchus spp., Hemicriconemoides, Hemicycliophora *arenaria*, Hemicycliophora *nudata*, Hemicycliophora *parvana*, *Heterodera avenae*, *Heterodera cruciferae*, *Heterodera glycines* (soya bean cyst nematode), *Heterodera oryzae*, *Heterodera schachtii*, *Heterodera zeae* and the non-migratory cyst-forming parasites *Heterodera* spp., Hirschmaniella *gracilis*, Hirschmaniella *oryzae*, Hirschmaniella *spinicaudata* and the stem and leaf endoparasites Hirschmaniella spp., Hoplolaimus aegyptii, Hoplolaimus *californicus*, Hoplolaimus *columbus*, Hoplolaimus *galeatus*, Hoplolaimus *indicus*, Hoplolaimus magnistylus, Hoplolaimus *pararobustus*, Longidorus *africanus*, Longidorus breviannulatus, Longidorus *elongatus*, Longidorus laevicapitatus, Longidorus vineacola and the ectoparasites Longidorus spp., Meloidogyne acronea, Meloidogyne *africana*, Meloidogyne *arenaria*, Meloidogyne *arenaria* thamesi, Meloidogyne artiella, Meloidogyne chitwoodi, Meloidogyne *coffeicola*, Meloidogyne *ethiopica*, Meloidogyne *exigua*, Meloidogyne *fallax*, Meloidogyne *graminicola*, Meloidogyne *graminis*, Meloidogyne *hapla*, Meloidogyne *incognita*, Meloidogyne *incognita acrita*, Meloidogyne *javanica*, Meloidogyne *kikuyensis*, Meloidogyne *minor*, Meloidogyne *naasi*, Meloidogyne *paranaensis*, Meloidogyne thamesi and the non-migratory parasites Meloidogyne spp., Meloinema spp., Nacobbus *aberrans*, Neotylenchus vigissi, Paraphelenchus pseudoparietinus, Paratrichodorus allius, Paratrichodorus *lobatus*, Paratrichodorus *minor*, Paratrichodorus *nanus*, Paratrichodorus *porosus*, Paratrichodorus *teres* and Paratrichodorus spp., Paratylenchus *hamatus*, Paratylenchus *minutus*, Paratylenchus *projectus* and Paratylenchus spp., Pratylenchus *agilis*, Pratylenchus *alleni*, Pratylenchus *andinus*, Pratylenchus *brachyurus*, Pratylenchus *cerealis*, Pratylenchus *coffeae*, Pratylenchus *crenatus*, Pratylenchus *delattrei*, Pratylenchus *giibbicaudatus*, Pratylenchus *goodeyi*, Pratylenchus *hamatus*, Pratylenchus *hexincisus*, Pratylenchus *loosi*, Pratylenchus *neglectus*, Pratylenchus *penetrans*, Pratylenchus *pratensis*, Pratylenchus *scribneri*, Pratylenchus *teres*, Pratylenchus *thornei*, Pratylenchus *vulnus*, Pratylenchus *zeae* and the migratory endoparasites Pratylenchus spp., Pseudohalenchus *minutus*, Psilenchus *magnidens*, Psilenchus *tumidus*, Punctodera *chalcoensis*, Quinisulcius *acutus*, Radopholus citrophilus, Radopholus *similis*, the migratory endoparasites Radopholus spp., Rotylenchulus *borealis*, Rotylenchulus *parvus*, Rotylenchulus *reniformis* and Rotylenchulus spp., Rotylenchus *laurentinus*, Rotylenchus *macrodoratus*, Rotylenchus *robustus*, Rotylenchus *uniformis* and Rotylenchus spp., Scutellonema *brachyurum*, Scutellonema bradys, Scutellonema clathricaudatum and the migratory endoparasites Scutellonema spp., Subanguina radiciola, Tetylenchus *nicotianae*, Trichodorus *cylindricus*, Trichodorus *minor*, Trichodorus *primitivus*, Trichodorus *proximus*, Trichodorus *similis*, Trichodorus *sparsus* and the ectoparasites Trichodorus spp., Tylenchorhynchus *agri*, Tylenchorhynchus *brassicae*, Tylenchorhynchus *clarus*, Tylenchorhynchus *claytoni*, Tylenchorhynchus *digitatus*, Tylenchorhynchus *ebriensis*, Tylenchorhynchus *maximus*, Tylenchorhynchus *nudus*, Tylenchorhynchus *vulgaris* and Tylenchorhynchus spp., Tylenchulus *semipenetrans* and the semiparasites Tylenchulus spp., Xiphinema *americanum*, Xiphinema *brevicolle*, Xiphinema *dimorphicaudatum*, Xiphinema *index* and the ectoparasites Xiphinema spp.

Nematodes for the control of which a compound of the formula (I) may be used include nematodes of the genus Meloidogyne such as the Southern root-knot nematode (Meloidogyne *incognita*), the Javanese root-knot nematode (Meloidogyne *javanica*), the Northern root-knot nematode (Meloidogyne *hapla*) and the peanut root-knot nematode (Meloidogyne *arenaria*); nematodes of the genus Ditylenchus such as the potato rot nematode (Ditylenchus *destructor*) and stem and bulb eelworm (Ditylenchus *dipsaci*); nematodes of the genus Pratylenchus such as the cob root-lesion nematode (Pratylenchus *penetrans*), the chrysanthemum root-lesion nematode (Pratylenchus *fallax*), the coffee root nematode (Pratylenchus *coffeae*), the tea root nematode (Pratylenchus *loosi*) and the walnut root-lesion nematode (Pratylenchus *vulnus*); nematodes of the genus Globodera such as the yellow potato cyst nematode (Globodera *rostochiensis*) and the white potato cyst nematode (Globodera *pallida*); nematodes of the genus Heterodera such as the soya bean cyst nematode (*Heterodera glycines*) and the beet cyst eelworm (*Heterodera schachtii*); nematodes of the genus Aphelenchoides such as the rice white-tip nematode (Aphelenchoides *besseyi*), the chrysanthemum nematode (Aphelenchoides ritzemabosi) and the strawberry nematode (Aphelenchoides *fragariae*); nematodes of the genus Aphelenchus such as the fungivorous nematode (Aphelenchus *avenae*); nematodes of the genus Radopholus, such as the burrowing nematode (Radopholus *similis*); nematodes of the genus Tylenchulus such as the citrus root nematode (Tylenchulus semipenetrans); nematodes of the genus Rotylenchulus such as the reniform nematode (Rotylenchulus *reniformis*); tree-dwelling nematodes such as the pine wood nematode (Bursaphelenchus *xylophilus*) and the red ring nematode (Bursaphelenchus *cocophilus*) and the like.

Plants for the protection of which a compound of the formula (I) can be used include plants such as cereals (for example rice, barley, wheat, rye, oats, maize and the like), beans (soya bean, azuki bean, bean, broadbean, peas, peanuts and the like), fruit trees/fruits (apples, citrus species, pears, grapevines, peaches, Japanese apricots, cherries, walnuts, almonds, bananas, strawberries and the like), vegetable species (cabbage, tomato, spinach, broccoli, lettuce, onions, spring onion, pepper and the like), root crops (carrot, potato, sweet potato, radish, lotus root, turnip and the like), plants for industrial raw materials (cotton, hemp, paper mulberry, mitsumata, rape, beet, hops, sugar cane, sugar beet, olive, rubber, palm trees, coffee, tobacco, tea and the like), cucurbits (pumpkin, cucumber, watermelon, melon and the like), meadow plants (cocksfoot, sorghum, timothy-grass, clover, alfalfa and the like), lawn grasses (mascarene grass, bentgrass and the like), spice plants etc. (lavender, rosemary, thyme, parsley, pepper, ginger and the like) and flowers (chrysanthemums, rose, orchid and the like).

The compounds of the formula (I) are particularly suitable for controlling coffee nematodes, in particular Pratylenchus *brachyurus*, Pratylenchus *coffeae*, Meloidogyne *exigua*, Meloidogyne *incognita*, Meloidogyne *coffeicola*, Helicotylenchus spp. and also Meloidogyne *paranaensis*, Rotylenchus spp., Xiphinema spp., Tylenchorhynchus spp. and Scutellonema spp.

The compounds of the formula (I) are particularly suitable for controlling potato nematodes, in particular Pratylenchus *brachyurus*, Pratylenchus *pratensis*, Pratylenchus *scribneri*, Pratylenchus *penetrans*, Pratylenchus *coffeae*, Ditylenchus *dipsaci* and also Pratylenchus *alleni*, Pratylenchus *andinus*, Pratylenchus *cerealis*, Pratylenchus *crenatus*, Pratylenchus *hexincisus*, Pratylenchus *loosi*, Pratylenchus *neglectus*, Pratylenchus *teres*, Pratylenchus *thornei*, Pratylenchus *vulnus*, Belonolaimus *longicaudatus*, Trichodorus *cylindricus*, Trichodorus *primitivus*, Trichodorus *proximus*, Trichodorus *similis*, Trichodorus *sparsus*, Paratrichodorus *minor*, Paratrichodorus allius, Paratrichodorus *nanus*, Paratrichodorus *teres*, Meloidogyne *arenaria*, Meloidogyne *fallax*, Meloidogyne *hapla*, Meloidogyne *thamesi*, Meloidogyne *incognita*, Meloidogyne *chitwoodi*, Meloidogyne *javanica*, Nacobbus *aberrans*, Globodera *rostochiensis*, Globodera *pallida*, Ditylenchus *destructor*, Radopholus *similis*, Rotylenchulus *reniformis*, Neotylenchus vigissi, Paraphelenchus pseudoparietinus, Aphelenchoides *fragariae* and Meloinema spp.

The compounds of the formula (I) are particularly suitable for controlling tomato nematodes, in particular Meloidogyne *arenaria*, Meloidogyne *hapla*, Meloidogyne *javanica*, Meloidogyne *incognita*, Pratylenchus *penetrans* and also Pratylenchus *brachyurus*, Pratylenchus *coffeae*, Pratylenchus *scribneri*, Pratylenchus *vulnus*, Paratrichodorus *minor*, Meloidogyne *exigua*, Nacobbus *aberrans*, Globodera *solanacearum*, Dolichodorus *heterocephalus* and Rotylenchulus reniformis.

The compounds of the formula (I) are particularly suitable for controlling cucumber plant nematodes, in particular Meloidogyne *arenaria*, Meloidogyne *hapla*, Meloidogyne *javanica*, Meloidogyne *incognita*, Rotylenchulus *reniformis* and Pratylenchus *thornei*.

The compounds of the formula (I) are particularly suitable for controlling cotton nematodes, in particular Belonolaimus *longicaudatus*, Meloidogyne *incognita*, Hoplolaimus *columbus*, Hoplolaimus *galeatus* and Rotylenchulus *reniformis*.

The compounds of the formula (I) are particularly suitable for controlling maize nematodes, in particular Belonolaimus *longicaudatus*, Paratrichodorus *minor* and also Pratylenchus *brachyurus*, Pratylenchus *delattrei*, Pratylenchus hexincisus, Pratylenchus *penetrans*, Pratylenchus *zeae*, (Belonolaimus *gracilis*), Belonolaimus *nortoni*, Longidorus breviannulatus, Meloidogyne *arenaria*, Meloidogyne *arenaria* thamesi, Meloidogyne *graminis*, Meloidogyne *incognita*, Meloidogyne *incognita* acrita, Meloidogyne *javanica*, Meloidogyne *naasi, Heterodera avenae, Heterodera oryzae, Heterodera zeae*, Punctodera *chalcoensis*, Ditylenchus *dipsaci*, Hoplolaimus aegyptii, Hoplolaimus magnistylus, Hoplolaimus galeatus, Hoplolaimus *indicus*, Helicotylenchus digonicus, Helicotylenchus dihystera, Helicotylenchus *pseudorobustus*, Xiphinema americanum, Dolichodorus *heterocephalus*, Criconemella ornata, Criconemella *onoensis*, Radopholus similis, Rotylenchulus *borealis*, Rotylenchulus *parvus*, Tylenchorhynchus *agri*, Tylenchorhynchus *clarus*, Tylenchorhynchus *claytoni*, Tylenchorhynchus *maximus*, Tylenchorhynchus *nudus*, Tylenchorhynchus *vulgaris*, Quinisulcius *acutus*, Paratylenchus *minutus*, Hemicycliophora parvana, Aglenchus *agricola, Anguina tritici*, Aphelenchoides *arachidis*, Scutellonema *brachyurum* and Subanguina radiciola.

The compounds of the formula (I) are particularly suitable for controlling soya bean nematodes, in particular Pratylenchus *brachyurus*, Pratylenchus *pratensis*, Pratylenchus *penetrans*, Pratylenchus *scribneri*, Belonolaimus *longicaudatus, Heterodera glycines*, Hoplolaimus *columbus* and also Pratylenchus *coffeae*, Pratylenchus hexincisus, Pratylenchus *neglectus*, Pratylenchus *crenatus*, Pratylenchus *alleni*, Pratylenchus *agilis*, Pratylenchus *zeae*, Pratylenchus *vulnus*, (Belonolaimus *gracilis*), Meloidogyne *arenaria*, Meloidogyne *incognita*, Meloidogyne *javanica*, Meloidogyne *hapla*, Hoplolaimus *columbus*, Hoplolaimus *galeatus* and Rotylenchulus *reniformis*.

The compounds of the formula (I) are particularly suitable for controlling tobacco nematodes, in particular Meloidogyne *incognita*, Meloidogyne *javanica* and also Pratylenchus *brachyurus*, Pratylenchus *pratensis*, Pratylenchus hexincisus, Pratylenchus *penetrans*, Pratylenchus *neglectus*, Pratylenchus *crenatus*, Pratylenchus *thornei*, Pratylenchus *vulnus*, Pratylenchus *zeae*, Longidorus *elongatu*, Paratrichodorus *lobatus*, Trichodorus spp., Meloidogyne *arenaria*, Meloidogyne *hapla*, Globodera *tabacum*, Globodera *solanacearum*, Globodera *virginiae*, Ditylenchus *dipsaci*, Rotylenchus spp., Helicotylenchus spp., Xiphinema *americanum*, Criconemella spp., Rotylenchulus *reniformis*, Tylenchorhynchus *claytoni*, Paratylenchus spp. and Tetylenchus *nicotianae*.

The compounds of the formula (I) are particularly suitable for controlling citrus nematodes, in particular Pratylenchus *coffeae* and also Pratylenchus *brachyurus*, Pratylenchus *vulnus*, Belonolaimus *longicaudatus*, Paratrichodorus *minor*, Paratrichodorus *porosus*, Trichodorus, Meloidogyne *incognita*, Meloidogyne *incognita acrita*, Meloidogyne *javanica*, Rotylenchus macrodoratus, Xiphinema *americanum*, Xiphinema *brevicolle*, Xiphinema *index*, Criconemella spp., Hemicriconemoides, Radopholus *similis* and Radopholus *citrophilus*, Hemicycliophora *arenaria*, Hemicycliophora *nudata* and Tylenchulus semipenetrans.

The compounds of the formula (I) are particularly suitable for controlling banana nematodes, in particular Pratylenchus *coffeae*, Radopholus *similis* and also Pratylenchus giibbicaudatus, Pratylenchus *loosi*, Meloidogyne spp., Helicotylenchus *multicinctus*, Helicotylenchus dihystera and Rotylenchulus spp.

The compounds of the formula (I) are particularly suitable for controlling pineapple nematodes, in particular Pratylenchus *zeae*, Pratylenchus *pratensis*, Pratylenchus *brachyurus*, Pratylenchus *goodeyi*, Meloidogyne spp., Rotylenchulus *reniformis* and also Longidorus *elongatus*, Longidorus laevicapitatus, Trichodorus *primitivus*, Trichodorus *minor, Heterodera* spp., Ditylenchus myceliophagus, Hoplolaimus *californicus*, Hoplolaimus *pararobustus*, Hoplolaimus *indicus*, Helicotylenchus dihystera, Helicotylenchus *nannus*, Helicotylenchus *multicinctus*, Helicotylenchus erythrine, Xiphinema dimorphicaudatum, Radopholus *similis*, Tylenchorhynchus *digitatus*, Tylenchorhynchus *ebriensis*, Paratylenchus *minutus*, Scutellonema clathricaudatum, Scutellonema bradys, Psilenchus *tumidus*, Psilenchus *magnidens*, Pseudohalenchus *minutus*, Criconemoides ferniae, Criconemoides *onoense* and Criconemoides *ornatum*.

The compounds of the formula (I) are particularly suitable for controlling grapevine nematodes, in particular Pratylenchus *vulnus*, Meloidogyne *arenaria*, Meloidogyne *incognita*, Meloidogyne *javanica*, Xiphinema *americanum*, Xiphinema *index* and also Pratylenchus *pratensis*, Pratylenchus *scribneri*, Pratylenchus *neglectus*, Pratylenchus *brachyurus*, Pratylenchus *thornei* and Tylenchulus semipenetrans.

The compounds of the formula (I) are particularly suitable for controlling nematodes in tree crops—pome fruit, in particular Pratylenchus *penetrans* and from Pratylenchus *vulnus*, Longidorus *elongatus*, Meloidogyne *incognita* and Meloidogyne *hapla*.

The compounds of the formula (I) are particularly suitable for controlling nematodes in tree crops—stone fruit, in particular Pratylenchus *penetrans*, Pratylenchus *vulnus*, Meloidogyne *arenaria*, Meloidogyne *hapla*, Meloidogyne *javanica*, Meloidogyne *incognita*, Criconemella *xenoplax* and from Pratylenchus *brachyurus*, Pratylenchus *coffeae*, Pratylenchus *scribneri*, Pratylenchus *zeae*, Belonolaimus *longicaudatus*, Helicotylenchus *dihystera*, Xiphinema *americanum*, Criconemella *curvata*, Tylenchorhynchus *claytoni*, Paratylenchus *hamatus*, Paratylenchus *projectus*, Scutellonema *brachyurum* and Hoplolaimus *galeatus*.

The compounds of the formula (I) are particularly suitable for controlling nematodes in tree crops, sugar cane and rice, in particular Trichodorus spp., Criconemella spp. and from Pratylenchus spp., Paratrichodorus spp., Meloidogyne spp., Helicotylenchus spp., Tylenchorhynchus spp., Aphelenchoides spp., *Heterodera* spp., Xiphinema spp. and Cacopaurus *pestis*.

In the present context, the term "nematodes" also refers to nematodes damaging humans or animals.

Specific nematode species harmful to humans or to animals are:

Trichinellida, for example: Trichuris spp., *Capillaria* spp., Paracapillaria spp., Eucoleus spp., Trichomosoides spp., Trichinella spp.

from the order of Tylenchida, for example: *Micronema* spp., *Strongyloides* spp.

from the order of Rhabditida, for example: *Strongylus* spp., Triodontophorus spp., Oesophagodontus spp., *Trichonema* spp., Gyalocephalus spp., Cylindropharynx spp., Poteriostomum spp., Cyclococercus spp., Cylicostephanus spp., Oesophagostomum spp., *Chabertia* spp., Stephanurus spp., Ancylostoma spp., *Uncinaria* spp., *Necator* spp., Bunostomum spp., *Globocephalus* spp., Syngamus spp., Cyathostoma spp., Metastrongylus spp., Dictyocaulus spp., Muellerius spp., Protostrongylus spp., Neostrongylus spp., Cystocaulus spp., Pneumostrongylus spp., Spicocaulus spp., Elaphostrongylus spp., Parelaphostrongylus spp., Crenosoma spp., Paracrenosoma spp., Oslerus spp., Angiostrongylus spp., Aelurostrongylus spp., Filaroides spp., Parafilaroides spp., Trichostrongylus spp., Haemonchus spp., Ostertagia spp., Teladorsagia spp., Marshallagia spp., *Cooperia* spp., Nippostrongylus spp., Heligmosomoides spp., Nematodirus spp., Hyostrongylus spp., *Obeliscoides* spp., Amidostomum spp., Ollulanus spp.

From the order of Spirurida, for example: *Oxyuris* spp., Enterobius spp., Passalurus spp., Syphacia spp., Aspiculuris spp., Heterakis spp.; *Ascaris* spp., Toxascaris spp., Toxocara spp., Baylisascaris spp., Parascaris spp., Anisakis spp., Ascaridia spp.; Gnathostoma spp., Physaloptera spp., Thelazia spp., Gongylonema spp., Habronema spp., Parabronema spp., Draschia spp., *Dracunculus* spp.; Stephanofilaria spp., Parafilaria spp., *Setaria* spp., *Loa* spp., *Dirofilaria* spp., Litomosoides spp., Brugia spp., Wuchereria spp., Onchocerca spp., Spirocerca spp.;

Many known nematicides also act against other parasitic helminths and are therefore used for controlling worms—not necessarily belonging to the group Nematoda—which are parasites in humans and animals. The present invention also relates to the use of the compounds of the formula (I) as anthelmintic medicaments. The pathogenic endoparasitic helminths include Platyhelmintha (e.g. Monogenea, cestodes and trematodes), Acanthocephala and Pentastoma. The following helminths may be mentioned as being preferred:

Monogenea: for example: *Gyrodactylus* spp., *Dactylogyrus* spp., Polystoma spp.

Cestodes: from the order of the Pseudophyllidea, for example: *Diphyllobothrium* spp., *Spirometra* spp., *Schistocephalus* spp., *Ligula* spp., *Bothridium* spp., Diphlogonoporus spp.

from the order of Cyclophyllida, for example: *Mesocestoides* spp., Anoplocephala spp., Paranoplocephala spp., *Moniezia* spp., Thysanosoma spp., Thysaniezia spp., Avitellina spp., *Stilesia* spp., Cittotaenia spp., Andyra spp., *Bertiella* spp., *Taenia* spp., *Echinococcus* spp., Hydatigera spp., Davainea spp., *Raillietina* spp., *Hymenolepis* spp., *Echinolepis* spp., *Echinocotyle* spp., *Diorchis* spp., *Dipylidium* spp., Joyeuxiella spp., Diplopylidium spp.

Trematodes: from the class of the Digenea, for example: *Diplostomum* spp., *Posthodiplostomum* spp., *Schistosoma* spp., *Trichobilharzia* spp., *Ornithobilharzia* spp., *Austrobilharzia* spp., *Gigantobilharzia* spp., *Leucochloridium* spp., *Brachylaima* spp., *Echinostoma* spp., *Echinoparyphium* spp., *Echinochasmus* spp., *Hypoderaeum* spp., *Fasciola* spp., *Fascioloides* spp., *Fasciolopsis* spp., *Cyclocoelum* spp., Typhlocoelum spp., *Paramphistomum* spp., Calicophoron spp., Cotylophoron spp., Gigantocotyle spp., Fischoederius spp., Gastrothylacus spp., *Notocotylus* spp., *Catatropis* spp., *Plagiorchis* spp., *Prosthogonimus* spp., Dicrocoelium spp., Eurytrema spp., Troglotrema spp., Paragonimus spp., Collyriclum spp., Nanophyetus spp., *Opisthorchis* spp., Clonorchis spp., *Metorchis* spp., *Heterophyes* spp., *Metagonimus* spp.

Acanthocephala: from the order of the Oligacanthorhynchida, for example: *Macracanthorhynchus* spp., *Prosthenorchis* spp.; from the order Polymorphida for example: *Filicollis* spp.; from the order Moniliformida for example: *Moniliformis* spp.

From the order of the Echinorhynchida, for example, *Acanthocephalus* spp., *Echinorhynchus* spp., *Leptorhynchoides* spp.

Pentastoma: from the order of the Porocephalida, for example, *Linguatula* spp.

In the veterinary field and in animal husbandry, the administration of the compounds of the formula (I) is carried out in a known manner, directly or enterally, parenterally, dermally or nasally in the form of suitable use forms. Administration may be prophylactic or therapeutic.

The compounds of the formula (I) can, as the case may be, at certain concentrations or application rates, also be used as herbicides, safeners, growth regulators or agents to improve plant properties, as microbicides or gametocides, for example as fungicides, antimycotics, bactericides, virucides (including agents against viroids) or as agents against MLO (*mycoplasma*-like organisms) and RLO (*rickettsia*-like organisms). They can, as the case may be, also be used as intermediates or precursors for the synthesis of further active compounds.

Formulations

The present invention further relates to formulations and use forms prepared therefrom as pesticides, for example drench, drip and spray liquors, comprising at least one compound of the formula (I). Optionally, the use forms comprise further pesticides and/or adjuvants which improve action, such as penetrants, e.g. vegetable oils, for example rapeseed oil, sunflower oil, mineral oils, for example paraffin oils, alkyl esters of vegetable fatty acids, for example rapeseed oil methyl ester or soya oil methyl ester, or alkanol alkoxylates and/or spreaders, for example alkylsiloxanes and/or salts, for example organic or inorganic ammonium or phosphonium salts, for example ammonium sulfate or diammonium hydrogenphosphate and/or retention promoters, for example dioctyl sulfosuccinate or hydroxypropylguar polymers and/or humectants, for example glycerol and/or fertilizers, for example ammonium-, potassium- or phosphorus-containing fertilizers.

Customary formulations are, for example, water-soluble liquids (SL), emulsion concentrates (EC), emulsions in water (EW), suspension concentrates (SC, SE, FS, OD), water-dispersible granules (WG), granules (GR) and capsule concentrates (CS); these and further possible formulation types are described, for example, by Crop Life International and in Pesticide Specifications, Manual on development and use of FAO and WHO specifications for pesticides, FAO Plant Production and Protection Papers—173, prepared by the FAO/WHO Joint Meeting on Pesticide Specifications, 2004, ISBN: 9251048576. The formulations, in addition to one or more compounds of the formula (I), optionally comprise further agrochemically active ingredients.

Preference is given to formulations or use forms comprising auxiliaries, for example extenders, solvents, spontaneity promoters, carriers, emulsifiers, dispersants, frost protection agents, biocides, thickeners and/or further auxiliaries, for example adjuvants. An adjuvant in this context is a component which enhances the biological effect of the formulation, without the component itself having any biological effect. Examples of adjuvants are agents which promote retention, spreading, attachment to the leaf surface or penetration.

These formulations are prepared in a known way, for example by mixing the compounds of the formula (I) with auxiliaries such as, for example, extenders, solvents and/or solid carriers and/or other auxiliaries such as, for example, surfactants. The formulations are produced either in suitable facilities or else before or during application.

The auxiliaries used may be substances suitable for imparting special properties, such as certain physical, technical and/or biological properties, to the formulation of the compounds of the formula (I), or to the use forms prepared from these formulations (for example ready-to-use pesticides such as spray liquors or seed dressing products).

Suitable extenders are, for example, water, polar and nonpolar organic chemical liquids, for example from the classes of the aromatic and non-aromatic hydrocarbons (such as paraffins, alkylbenzenes, alkylnaphthalenes, chlorobenzenes), the alcohols and polyols (which, if appropriate, may also be substituted, etherified and/or esterified), the ketones (such as acetone, cyclohexanone), esters (including fats and oils) and (poly)ethers, the simple and substituted amines, amides, lactams (such as N-alkylpyrrolidones) and lactones, the sulfones and sulfoxides (such as dimethyl sulfoxide).

If the extender utilized is water, it is also possible to use, for example, organic solvents as auxiliary solvents. Liquid solvents are essentially: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulfoxide, and water.

In principle, it is possible to use all suitable solvents. Examples of suitable solvents are aromatic hydrocarbons, such as xylene, toluene or alkylnaphthalenes, chlorinated aromatic or aliphatic hydrocarbons, such as chlorobenzene, chloroethylene or methylene chloride, aliphatic hydrocarbons, such as cyclohexane, paraffins, mineral oil fractions, mineral and vegetable oils, alcohols, such as methanol, ethanol, isopropanol, butanol or glycol and their ethers and esters, ketones such as acetone, methyl ethyl ketone, methyl isobutyl ketone or cyclohexanone, strongly polar solvents, such as dimethyl sulfoxide, and also water.

In principle, it is possible to use all suitable carriers. Useful carriers especially include: for example ammonium salts and ground natural minerals such as kaolins, clays, talc, chalk, quartz, attapulgite, montmorillonite or diatomaceous earth, and synthetic minerals such as finely divided silica, alumina and natural or synthetic silicates, resins, waxes and/or solid fertilizers. It is likewise possible to use mixtures of such carriers. Useful carriers for granules include: for example crushed and fractionated natural rocks such as calcite, marble, pumice, sepiolite, dolomite, and synthetic granules of inorganic and organic flours, and also granules of organic material such as sawdust, paper, coconut shells, maize cobs and tobacco stalks.

It is also possible to use liquefied gaseous extenders or solvents. Especially suitable are those extenders or carriers which are gaseous at standard temperature and under atmospheric pressure, for example aerosol propellants such as halogenated hydrocarbons, and also butane, propane, nitrogen and carbon dioxide.

Examples of emulsifiers and/or foam formers, dispersants or wetting agents having ionic or nonionic properties or mixtures of these surface-active substances are salts of polyacrylic acid, salts of lignosulfonic acid, salts of phenolsulfonic acid or naphthalenesulfonic acid, polycondensates of ethylene oxide with fatty alcohols or with fatty acids or with fatty amines, with substituted phenols (preferably alkylphenols or arylphenols), salts of sulfosuccinic esters, taurine derivatives (preferably alkyl taurates), phosphoric esters of polyethoxylated alcohols or phenols, fatty acid esters of polyols, and derivatives of the compounds containing sulfates, sulfonates and phosphates, for example alkylaryl polyglycol ethers, alkylsulfonates, alkyl sulfates, arylsulfonates, protein hydrolysates, lignosulfite waste liquors and methylcellulose. The presence of a surfactant is advantageous if one of the compounds of the formula (I) and/or one of the inert carriers is insoluble in water and if the application takes place in water.

Further auxiliaries which may be present in the formulations and the use forms derived therefrom are dyes such as inorganic pigments, for example iron oxide, titanium oxide and Prussian Blue, and organic dyes such as alizarin dyes, azo dyes and metal phthalocyanine dyes, and nutrients and trace nutrients such as salts of iron, manganese, boron, copper, cobalt, molybdenum and zinc.

Additional components which may be present are stabilizers, such as cold stabilizers, preservatives, antioxidants, light stabilizers, or other agents which improve chemical and/or physical stability. Foam generators or antifoams may also be present.

In addition, the formulations and the use forms derived therefrom may also comprise, as additional auxiliaries, stickers such as carboxymethylcellulose and natural or synthetic polymers in the form of powders, granules or latices, such as gum arabic, polyvinyl alcohol and polyvinyl acetate, or else natural phospholipids such as cephalins and lecithins and synthetic phospholipids. Further auxiliaries may be mineral and vegetable oils.

It is possible if appropriate for still further auxiliaries to be present in the formulations and the use forms derived therefrom. Examples of such additives are fragrances, protective colloids, binders, adhesives, thickeners, thixotropic agents, penetrants, retention promoters, stabilizers, sequestrants, complexing agents, humectants, spreaders. In general, the compounds of the formula (I) can be combined with any solid or liquid additive commonly used for formulation purposes.

Useful retention promoters include all those substances which reduce dynamic surface tension, for example dioctyl sulfosuccinate, or increase viscoelasticity, for example hydroxypropylguar polymers.

Useful penetrants in the present context are all those substances which are typically used to improve the penetration of agrochemically active compounds into plants. Penetrants are defined in this context by their ability to penetrate from the (generally aqueous) application liquor and/or from the spray coating into the cuticle of the plant and hence increase the mobility of the active ingredients in the cuticle. The method described in the literature (Baur et al., 1997, Pesticide Science 51, 131-152) can be used for determining this property. Examples include alcohol alkoxylates such as coconut fatty ethoxylate (10) or isotridecyl ethoxylate (12), fatty acid esters, for example rapeseed oil methyl ester or soya oil methyl ester, fatty amine alkoxylates, for example tallowamine ethoxylate (15), or ammonium and/or phosphonium salts, for example ammonium sulfate or diammonium hydrogenphosphate.

The formulations preferably comprise between 0.00000001% and 98% by weight of the compound of the formula (I), more preferably between 0.01% and 95% by weight of the compound of the formula (I), most preferably between 0.5% and 90% by weight of the compound of the formula (I), based on the weight of the formulation.

The content of the compound of the formula (I) in the use forms prepared from the formulations (in particular pesticides) may vary within wide ranges. The concentration of the compound of the formula (I) in the use forms may typically be between 0.00000001% and 95% by weight of the compound of the formula (I), preferably between 0.00001% and 1% by weight, based on the weight of the use form. Application is accomplished in a customary manner appropriate for the use forms.

Mixtures

The compounds of the formula (I) can also be used in a mixture with one or more suitable fungicides, bactericides, acaricides, molluscicides, nematicides, insecticides, microbiological agents, beneficial organisms, herbicides, fertilizers, bird repellents, phytotonics, sterilants, safeners, semiochemicals and/or plant growth regulators, in order thus, for example, to broaden the spectrum of action, prolong the period of action, enhance the rate of action, prevent repellency or prevent evolution of resistance. In addition, active ingredient combinations of this kind can improve plant growth and/or tolerance to abiotic factors, for example high or low temperatures, to drought or to elevated water content or soil salinity. It is also possible to improve flowering and fruiting performance, optimize germination capacity and root development, facilitate harvesting and improve yields, influence maturation, improve the quality and/or the nutritional value of the harvested products, prolong storage life and/or improve the processability of the harvested products.

In addition, the compounds of the formula (I) may be present in a mixture with other active ingredients or semiochemicals such as attractants and/or bird repellents and/or plant activators and/or growth regulators and/or fertilizers. Likewise, the compounds of the formula (I) can be used in mixtures with agents to improve plant properties, for example growth, yield and quality of the harvested material.

In a particular embodiment according to the invention, the compounds of the formula (I) are present in formulations or in the use forms prepared from these formulations in a mixture with further compounds, preferably those as described below.

If one of the compounds mentioned below can occur in different tautomeric forms, these forms are also included even if not explicitly mentioned in each case.

Insecticides/Acaricides/Nematicides

The active ingredients specified here with their common names are known and are described for example in "The Pesticide Manual", 16th ed., British Crop Protection Council 2012, or can be searched for on the Internet (e.g. http//www.alanwood.net/pesticides).

(1) Acetylcholinesterase (AChE) inhibitors, for example carbamates, e.g. alanycarb, aldicarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, triazamate, trimethacarb, XMC and xylylcarb; or organophosphates, e.g. acephate, azamethiphos, azinphos-ethyl, azinphos-methyl, cadusafos, chlorethoxyfos, chlorfenvinphos, chlormephos, chloropyrifos, chloropyrifos-methyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, imicyafos, isofenphos, isopropyl O-(methoxyaminothiophosphoryl) salicylate, isoxathion, malathion, mecarbam, methamidophos, methidathion, mevinphos, monocrotophos, naled, omethoate, oxydemetonmethyl, parathion, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, triclorfon and vamidothion.

(2) GABA-gated chloride channel antagonists, for example cyclodiene-organochlorines, e.g. chlordane and endosulfan or phenylpyrazoles (fiproles), e.g. ethiprole and fipronil.

(3) Sodium channel modulators/voltage-gated sodium channel blockers, for example pyrethroids, e.g. acrinathrin, allethrin, d-cis-trans allethrin, d-trans allethrin, bifenthrin, bioallethrin, bioallethrin S-cyclopentenyl isomer, bioresmethrin, cycloprothrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin [(1R)-trans isomers], deltamethrin, empenthrin [(EZ)-(1R) isomers], esfenvalerate, etofenprox, fenpropathrin, fenvalerate, flucythrinate, flumethrin, tau-fluvalinate, halfenprox, imiprothrin, kadethrin, momfluorothrin, permethrin, phenothrin [(1R)-trans isomer], prallethrin, pyrethrins (pyrethrum), resmethrin, silafluofen, tefluthrin, tetramethrin, tetramethrin [(1R) isomers)], tralomethrin and transfluthrin or DDT or methoxychlor.

(4) Nicotinergic acetylcholine receptor (nAChR) agonists, for example neonicotinoids, e.g. acetamiprid, clothianidin, dinotefuran, imidacloprid, nitenpyram, thiacloprid and thiamethoxam or nicotine or sulfoxaflor or flupyradifurone.

(5) Nicotinergic acetylcholine receptor (nAChR) allosteric activators, for example spinosyns, e.g. spinetoram and spinosad.

(6) Chloride channel activators, for example avermectins/milbemycins, e.g. abamectin, emamectin benzoate, lepimectin and milbemectin.

(7) Juvenile hormone mimics, for example, juvenile hormone analogues, e.g. hydroprene, kinoprene and methoprene or fenoxycarb or pyriproxyfen.

(8) Active ingredients having unknown or nonspecific mechanisms of action, for example
alkyl halides, e.g. methyl bromide and other alkyl halides; or chloropicrine or sulfuryl fluoride or borax or tartar emetic.

(9) Selective antifeedants, e.g. pymetrozine or flonicamid.

(10) Mite growth inhibitors, e.g. clofentezine, hexythiazox and diflovidazin or etoxazole.

(11) Microbial disruptors of insect midgut membranes, e.g. *Bacillus thuringiensis* subspecies *israelensis*, *Bacillus sphaericus*, *Bacillus thuringiensis* subspecies *aizawai*, *Bacillus thuringiensis* subspecies kurstaki, *Bacillus thuringiensis* subspecies tenebrionis, and BT plant proteins: Cry1Ab, Cry1Ac, Cry1Fa, Cry2Ab, mCry3A, Cry3Ab, Cry3Bb, Cry34/35Ab 1.

(12) Oxidative phosphorylation inhibitors, ATP disruptors, for example diafenthiuron or organotin compounds, e.g. azocyclotin, cyhexatin and fenbutatin oxide or propargite or tetradifon.

(13) Uncouplers of oxidative phosphorylation via disruption of the H proton gradient, for example chlorfenapyr, DNOC and sulfluramid.

(14) Nicotinic acetylcholine receptor antagonists, for example bensultap, cartap hydrochloride, thiocyclam, and thiosultap-sodium.

(15) Inhibitors of chitin biosynthesis, type 0, for example bistrifluron, chlorfluazuron, diflubenzuron, flucycloxuron, flufenoxuron, hexaflumuron, lufenuron, novaluron, noviflumuron, teflubenzuron and triflumuron.

(16) Inhibitors of chitin biosynthesis, type 1, for example buprofezin.

(17) Moulting disruptors (especially for Diptera, i.e. dipterans), for example cyromazine.

(18) Ecdysone receptor agonists, for example chromafenozide, halofenozide, methoxyfenozide and tebufenozide.

(19) Octopaminergic agonists, for example amitraz.

(20) Complex III electron transport inhibitors, for example hydramethylnon or acequinocyl or fluacrypyrim.

(21) Complex I electron transport inhibitors, for example METI acaricides, e.g. fenazaquin, fenpyroximate, pyrimidifen, pyridaben, tebufenpyrad and tolfenpyrad or rotenone (Derris).

(22) Voltage-gated sodium channel blockers, for example indoxacarb or metaflumizone.

(23) Inhibitors of acetyl-CoA carboxylase, for example tetronic and tetramic acid derivatives, e.g. spirodiclofen, spiromesifen and spirotetramat.

(24) Complex IV electron transport inhibitors, for example phosphines, e.g. aluminium phosphide, calcium phosphide, phosphine and zinc phosphide or cyanide.

(25) Complex II electron transport inhibitors, for example cyenopyrafen and cyflumetofen.

(28) Ryanodine receptor effectors, for example diamides, e.g. chlorantraniliprole, cyantraniliprole and flubendiamide.

Further active compounds having an unknown or unclear mechanism of action, for example afidopyropen, afoxolaner, azadirachtin, benclothiaz, benzoximate, bifenazate, broflanilide, bromopropylate, quinomethionate, cryolite, cyclaniliprole, cycloxaprid, cyhalodiamide, dicloromezotiaz, dicofol, diflovidazin, flometoquin, fluazaindolizine, fluensulfone, flufenerim, flufenoxystrobin, flufiprole, fluhexafon, fluopyram, fluralaner, fluxametamide, fufenozide, guadipyr, heptafluthrin, imidaclothiz, iprodione, lotilaner, meperfluthrin, paichongding, pyflubumide, pyridalyl, pyrifluquinazon, pyriminostrobin, sarolaner, tetramethylfluthrin, tetraniliprole, tetrachlorantraniliprole, tioxazafen, thiofluoximate, triflumezopyrim and iodomethane; and additionally preparations based on *Bacillus firmus* (I-1582, BioNeem, Votivo), and the following known active compounds: 1-{2-fluoro-4-methyl-5-[(2,2,2-trifluoroethyl)sulfinyl]phenyl}-3-(trifluoromethyl)-1H-1,2,4-triazole-5-amine (known from WO2006/043635), {1'-[(2E)-3-(4-chlorophenyl)prop-2-en-1-yl]-5-fluorospiro[indole-3,4'-piperidin]-1(2H)-yl}(2-chloropyridin-4-yl)methanone (known from WO2003/106457), 2-chloro-N-[2-{1-[(2E)-3-(4-chlorophenyl)prop-2-en-1-yl]piperidin-4-yl}-4-(trifluoromethyl)phenyl] isonicotinamide (known from WO2006/003494), 3-(2,5-dimethylphenyl)-4-hydroxy-8-methoxy-1,8-diazaspiro[4.5]dec-3-en-2-one (known from WO2009/049851), 3-(2,5-dimethylphenyl)-8-methoxy-2-oxo-1,8-diazaspiro[4.5]dec-3-en-4-yl ethyl carbonate (known from WO2009/049851), 4-(but-2-yn-1-yloxy)-6-(3,5-dimethylpiperidin-1-yl)-5-fluoropyrimidine (known from WO2004/099160), 4-(but-2-yn-1-yloxy)-6-(3-chlorophenyl)pyrimidine (known from WO2003/076415), PF1364 (CAS Reg. No. 1204776-60-2), methyl 2-[2-({[3-bromo-1-(3-chloropyridin-2-yl)-1H-pyrazol-5-yl]carbonyl}amino)-5-chloro-3-methylbenzoyl]-2-methylhydrazinecarboxylate (known from WO2005/085216), methyl 2-[2-({[3-bromo-1-(3-chloropyridin-2-yl)-1H-pyrazol-5-yl]carbonyl}amino)-5-cyano-3-methylbenzoyl]-2-ethylhydrazinecarboxylate (known from WO2005/085216), methyl 2-[2-({[3-bromo-1-(3-chloropyridin-2-yl)-1H-pyrazol-5-yl]carbonyl}amino)-5-cyano-3-methylbenzoyl]-2-methylhydrazinecarboxylate (known from WO2005- /085216), methyl 2-[3,5-dibromo-2-({[3-bromo-1-(3-chloropyridin-2-yl)-1H-pyrazol-5-yl]carbonyl}amino)benzoyl]-2-ethylhydrazinecarboxylate (known from WO2005/085216), N-[2-(5-amino-1,3,4-thiadiazol-2-yl)-4-chloro-6-methylphenyl]-3-bromo-1-(3-chloropyridin-2-yl)-1H-pyrazole-5-carboxamide (known from CN102057925), 4-[5-(3,5-dichlorophenyl)-5-(trifluoromethyl)-4,5-dihydro-1,2-oxazol-3-yl]-2-methyl-N-(1-oxidothietan-3-yl)benzamide (known from WO2009/080250), N-[(2E)-1-[(6-chloropyridin-3-yl)methyl]pyridin-2(1H)-ylidene]-2,2,2-trifluoroacetamide (known from WO2012/029672), 1-[(2-chloro-1,3-thiazol-5-yl)methyl]-4-oxo-3-phenyl-4H-pyrido[1,2-a]pyrimidin-1-ium-2-olate (known from WO2009/099929), 1-[(6-chloropyridin-3-yl)methyl]-4-oxo-3-phenyl-4H-pyrido[1,2-a]pyrimidin-1-ium-2-olate (known from WO2009/099929), 4-(3-{2,6-dichloro-4-[(3,3-dichloroprop-2-en-1-yl)oxy]phenoxy}propoxy)-2-methoxy-6-(trifluoromethyl)pyrimidine (known from CN101337940), N-[2-(tertbutylcarbamoyl)-4-chloro-6-methylphenyl]-1-(3-chloropyridin-2-yl)-3-(fluoromethoxy)-1H-pyrazole-5-carboxamide (known from WO2008/134969, butyl [2-(2,4-dichlorophenyl)-3-oxo-4-oxaspiro[4.5]dec-1-en-1-yl]carbonate (known from CN 102060818), 3E)-3-[1-[(6-chloro-3-pyridyl)methyl]-2-pyridylidene]-1,1,1-trifluoropropan-2-one (known from WO2013/144213, N-(methylsulfonyl)-6-[2-(pyridin-3-yl)-1,3-thiazol-5-yl]pyridine-2-carboxamide (known from WO2012/000896), N-[3-(benzylcarbamoyl)-4-chlorophenyl]-1-methyl-3-(pentafluoroethyl)-4-(trifluoromethyl)-1H-pyrazole-5-carboxamide (known from WO-2010/051926), 5-bromo-4-chloro-N-[4-chloro-2-methyl-6-(methylcarbamoyl)phenyl]-2-(3-chloro-2-pyridyl)pyrazole-3-carboxamide (known from CN103232431).

Fungicides

The active ingredients specified herein by their common name are known and described, for example, in the "Pesticide Manual" or on the Internet (for example: http://www.alanwood.net/pesticides).

All the fungicidal mixing components listed in classes (1) to (15) may optionally form salts with corresponding bases or acids if suitable functional groups are present. In addition, the fungicidal mixing components listed in classes (1) to (15) also include tautomeric forms if tautomerism is possible.

1) Inhibitors of the ergosterol biosynthesis, for example (1.01) aldimorph, (1.02) azaconazole, (1.03) bitertanol, (1.04) bromuconazole, (1.05) cyproconazole, (1.06) diclobutrazole, (1.07) difenoconazole, (1.08) diniconazole, (1.09) diniconazole-M, (1.10) dodemorph, (1.11) dodemorph acetate, (1.12) epoxiconazole, (1.13) etaconazole, (1.14) fenarimol, (1.15) fenbuconazole, (1.16) fenhexamide, (1.17) fenpropidin, (1.18) fenpropimorph, (1.19) fluquinconazole, (1.20) flurprimidol, (1.21) flusilazole, (1.22) flutriafol, (1.23) furconazole, (1.24) furconazole-cis, (1.25) hexaconazole, (1.26) imazalil, (1.27) imazalil sulfate, (1.28) imibenconazole, (1.29) ipconazole, (1.30) metconazole, (1.31) myclobutanil, (1.32) naftifine, (1.33) nuarimol, (1.34) oxpoconazole, (1.35) paclobutrazole, (1.36) pefurazoate, (1.37) penconazole, (1.38) piperalin, (1.39) prochloraz, (1.40) propiconazole, (1.41) prothioconazole, (1.42) pyributicarb, (1.43) pyrifenox, (1.44) quinconazole, (1.45) simeconazole, (1.46) spiroxamine, (1.47) tebuconazole, (1.48) terbinafin, (1.49) tetraconazole, (1.50) triadimefon, (1.51) triadimenol, (1.52) tridemorph, (1.53) triflumizole, (1.54) triforin, (1.55) triticonazole, (1.56) uniconazole, (1.57) uniconazole-p, (1.58) viniconazole, (1.59) voriconazole, (1.60) 1-(4-chlorophenyl)-2-(1H-1,2,4-triazol-1-yl)cycloheptanol, (1.61) 1-(2,2-dimethyl-2,3-dihydro-1H-inden-1-yl)-1H-imidazole-5-carboxylic acid methyl ester, (1.62) N'-{5-(difluoromethyl)-2-methyl-4-[3-(trimethylsilyl)propoxy]phenyl}-N-ethyl-N-methylimidoformamide, (1.63) N-ethyl-N-methyl-N'-{2-methyl-5-(trifluoromethyl)-4-[3-(trimethylsilyl)propoxy]phenyl}imido formamide, (1.64) O-[1-(4-methoxyphenoxy)-3,3-dimethylbutan-2-yl]-1H-imidazole-1-carbothioate, (1.65) pyrisoxazole, (1.66) 2-{[3-(2-chlorophenyl)-2-(2,4-difluorophenyl)oxiran-2-yl]methyl}-2,4-dihydro-3H-1,2,4-triazole-3-thione, (1.67) 1-{[3-(2-chlorophenyl)-2-(2,4-difluorophenyl)oxiran-2-yl]methyl}-1H-1,2,4-triazol-5-ylthiocyanate, (1.68) 5-(allylsulfanyl)-1-{[3-(2-chlorophenyl)-2-(2,4-difluorophenyl)oxiran-2-yl]methyl}-1H-1,2,4-triazole, (1.69) 2-[1-(2,4-dichlorophenyl)-5-hydroxy-2,6,6-trimethylheptan-4-yl-2,4-dihydro-3H-1,2,4-triazole-3-thione, (1.70) 2-{[rel(2R, 3S)-3-(2-chlorophenyl)-2-(2,4-difluorophenyl)oxiran-2-yl]methyl}-2,4-dihydro-3H-1,2,4-triazole-3-thione, (1.71) {[rel(2R,3R)-3-(2-chlorophenyl)-2-(2,4-difluorophenyl)oxiran-2-yl]methyl}-2,4-dihydro-3H-1,2,4-triazole-3-thione, (1.72) 1-{[rel(2R,3S)-3-(2-chlorophenyl)-2-(2,4-difluorophenyl)oxiran-2-yl]methyl}-1H-1,2,4-triazol-5-ylthiocyanate, (1.73) 1-{[rel(2R, 3R)-3-(2-chlorophenyl)-2-(2,4-difluorophenyl)oxiran-2-yl]methyl}-1H-1,2,4-triazol-5-ylthiocyanate, (1.74) 5-(allylsulfanyl)-1-{[rel(2R,3S)-3-(2-chlorophenyl)-2-(2,4-difluorophenyl)oxiran-2-yl]methyl}-1H-1,2,4-triazole, (1.75) 5-(allylsulfanyl)-1-{[rel(2R,3R)-3-(2-chlorophenyl)-2-(2,4-difluorophenyl)oxiran-2-yl]methyl}-1H-1,2,4-triazole, (1.76) 2-[(2S,4S,5S)-1-(2,4-dichlorophenyl)-5-hydroxy-2,6,6-trimethylheptan-4-yl]-2,4-dihydro-3H-1,2,4-triazole-3-thione, (1.77) 2-[(2R,4S,5S)-1-(2,4-dichlorophenyl)-5-hydroxy-2,6,6-trimethylheptan-4-yl]-2,4-dihydro-3H-1,2,4-triazole-3-thione, (1.78) 2-[(2R,4R,5R)-1-(2,4-dichlorophenyl)-5-hydroxy-2,6,6-trimethylheptan-4-yl]-2,4-dihydro-3H-1,2,4-triazole-3-thione, (1.79) 2-[(2S,4R,5R)-1-(2,4-dichlorophenyl)-5-hydroxy-2,6,6-trimethylheptan-4-yl]-2,4-dihydro-3H-1,2,4-triazole-3-thione, (1.80) 2-[(2S,4S,5R)-1-(2,4-dichlorophenyl)-5-hydroxy-2,6,6-trimethylheptan-4-yl]-2,4-dihydro-3H-1,2,4-triazole-3-thione, (1.81) 2-[(2R,4S,5R)-1-(2,4-dichlorophenyl)-5-hydroxy-2,6,6-trimethylheptan-4-yl]-2,4-dihydro-3H-1,2,4-triazole-3-thione, (1.82) 2-[(2R,4R,5S)-1-(2,4-dichlorophenyl)-5-hydroxy-2,6,6-trimethylheptan-4-yl]-2,4-dihydro-3H-1,2,4-triazole-3-thione, (1.83) 2-[(2S,4R,5S)-1-(2,4-dichlorophenyl)-5-hydroxy-2,6,6-trimethylheptan-4-yl]-2,4-dihydro-3H-1,2,4-triazole-3-thione, (1.84) 2-[4-(4-chlorophenoxy)-2-(trifluoromethyl)phenyl]-1-(1H-1,2,4-triazol-1-yl)propan-2-ol, (1.85) 2-[4-(4-chlorophenoxy)-2-(trifluoromethyl)phenyl]-1-(1H-1,2,4-triazol-1-yl)butan-2-ol, (1.86) 2-[4-(4-chlorophenoxy)-2-(trifluoromethyl)phenyl]-1-(1H-1,2,4-triazol-1-yl)pentan-2-ol, (1.87) 2-[2-chloro-4-(4-chlorophenoxy)phenyl]-1-(1H-1,2,4-triazol-1-yl)butan-2-ol, (1.88) 2-[2-chloro-4-(2,4-dichlorophenoxy)phenyl]-1-(1H-1,2,4-triazol-1-yl)propan-2-ol, (1.89) (2R)-2-(1-chlorocyclopropyl)-4-[(1R)-2,2-dichlorocyclopropyl]-1-(1H-1,2,4-triazol-1-yl)butan-2-ol, (1.90) (2R)-2-(1-chlorocyclopropyl)-4-[(1S)-2,2-dichlorocyclopropyl]-1-(1H-1,2,4-triazol-1-yl)butan-2-ol, (1.91) (2S)-2-(1-chlorocyclopropyl)-4-[(1S)-2,2-dichlorocyclopropyl]-1-(1H-1,2,4-triazol-1-yl)butan-2-ol, (1.92) (2S)-2-(1-chlorocyclopropyl)-4-[(1R)-2,2-dichlorocyclopropyl]-1-(1H-1,2,4-triazol-1-yl)butan-2-ol, (1.93) (1S,2R,5R)-5-(4-chlorobenzyl)-2-(chloromethyl)-2-methyl-1-(1H-1,2,4-triazol-1-ylmethyl)cyclopentanol, (1.94) (1R,2S,5S)-5-(4-chlorobenzyl)-2-(chloromethyl)-2-methyl-1-(1H-1,2,4-triazol-1-ylmethyl)cyclopentanol, (1.95) 5-(4-chlorobenzyl)-2-(chloromethyl)-2-methyl-1-(1H-1,2,4-triazol-1-ylmethyl)cyclopentanol.

2) Inhibitors of complex I or II of the respiratory chain, for example (2.01) bixafen, (2.02) boscalid, (2.03) carboxin, (2.04) diflumetorim, (2.05) fenfuram, (2.06) fluopyram, (2.07) flutolanil, (2.08) fluxapyroxad, (2.09) furametpyr, (2.10) furmecyclox, (2.11) isopyrazam (mixture of syn-epimeric racemate 1RS,4SR,9RS and anti-epimeric racemate 1RS,4SR,9SR), (2.12) isopyrazam (anti-epimeric racemate 1RS,4SR,9SR), (2.13) isopyrazam (anti-epimeric enantiomer 1R,4S,9S), (2.14) isopyrazam (anti-epimeric enantiomer 1S,4R, 9R), (2.15) isopyrazam (syn-epimeric racemate 1RS,4SR,9RS), (2.16) isopyrazam (syn-epimeric enantiomer 1R,4S,9R), (2.17) isopyrazam (syn-epimeric enantiomer 1S,4R,9S), (2.18) mepronil, (2.19) oxycarboxin, (2.20) penflufen, (2.21) penthiopyrad, (2.22) sedaxane, (2.23) thifluzamide, (2.24) 1-methyl-N-[2-(1,1,2,2-tetrafluoroethoxy)phenyl]-3-(trifluoromethyl)-1H-pyrazole-4-carboxamide, (2.25) 3-(difluoromethyl)-1-methyl-N-[2-(1,1,2,2-tetrafluoroethoxy)phenyl]-1H-pyrazole-4-carboxamide, (2.26) 3-(difluoromethyl)-N-[4-fluoro-2-(1,1,2,3,3,3-hexafluoropropoxy)phenyl]-1-methyl-1H-pyrazole-4-carboxamide, (2.27) N-[1-(2,4-dichlorophenyl)-1-methoxypropan-2-yl]-3-(difluoromethyl)-1-methyl-1H-pyrazole-4-carboxamide, (2.28) 5,8-difluoro-N-[2-(2-fluoro-4-{[4-(trifluoromethyl)pyridin-2-yl]oxy}phenyl)ethyl]quinazolin-4-amine, (2.29) benzovindiflupyr, (2.30) N-[(1 S,4R)-9-(dichloromethylene)-1,2,3,4-tetrahydro-1,4-methanonaphthalen-5-yl]-3-(difluoromethyl)-1-methyl-1H-pyrazole-4-carboxamide, (2.31) N-[(1R,4S)-9-(dichloromethylene)-1,2,3,4-tetrahydro-1,4-methanonaphthalen-5-yl]-3-(difluoromethyl)-1-methyl-1H-pyrazole-4-carboxamide, (2.32) 3-(difluoromethyl)-1-methyl-N-(1,1,3-trimethyl-2,3-dihydro-1H-inden-4-yl)-1H-pyrazole-4-carboxamide, (2.33) 1,3,5-trimethyl-N-(1,1,3-trimethyl-2,3-dihydro-1H-inden-4-yl)-1H-pyrazole-4-carboxamide, (2.34) 1-methyl-3-(trifluoromethyl)-N-(1,1,3-trimethyl-2,3-dihydro-1H-inden-4-yl)-1H-pyrazole-4-carboxamide, (2.35) 1-methyl-3-(trifluoromethyl)-N-[(3R)-1,1,3-trimethyl-2,3-dihydro-1H-inden-4-yl]-1H-pyrazole-4-carboxamide, (2.36) 1-methyl-3-(trifluoromethyl)-N-[(3S)-1,1,3-trimethyl-2,3-dihydro-1H-inden-4-yl]-1H-pyrazole-4-carboxamide, (2.37) 3-(difluoromethyl)-1-methyl-N-[(3S)-1,1,3-trimethyl-2,3-dihydro-1H-inden-4-yl]-1H-pyrazole-4-carboxamide, (2.38) 3-(difluoromethyl)-1-methyl-N-[(3R)-1,1,3-trimethyl-2,3-dihydro-1H-inden-4-yl]-1H-pyrazole-4-carboxamide, (2.39) 1,3,5-trimethyl-N-[(3R)-1,1,3-trimethyl-2,3-dihydro-1H-inden-4-yl]-1H-pyrazole-4-carboxamide, (2.40) 1,3,5-trimethyl-N-[(3S)-1,1,3-trimethyl-2,3-dihydro-1H-inden-4-yl]-1H-pyrazole-4-carboxamide, (2.41) benodanil, (2.42) 2-chloro-N-(1,1,3-trimethyl-2,3-dihydro-1H-inden-4-yl)pyridine-3-carboxamide, (2.43) isofetamide, (2.44) 1-methyl-3-(trifluoromethyl)-N-[2'-(trifluoromethyl)biphenyl-2-yl]-1H-pyrazole-4-carboxamide, (2.45) N-(4'-chlorobiphenyl-2-yl)-3-(difluoromethyl)-1-methyl-1H-pyrazole-4-carboxamide, (2.46) N-(2',4'-dichlorobiphenyl-2-yl)-3-(difluoromethyl)-1-methyl-1H-pyrazole-4-carboxamide, (2.47) 3-(difluoromethyl)-1-methyl-N-[4'-(trifluoromethyl)biphenyl-2-yl]–1H-pyrazole-4-carboxamide, (2.48) N-(2',5'-difluorobiphenyl-2-yl)-1-methyl-3–(trifluoromethyl)–1H-pyrazole-4-carboxamide, (2.49) 3-(difluoromethyl)-1-methyl-N-[4'-(prop-1-yn-1-yl)biphenyl-2-yl]–1H-pyrazole-4-carboxamide, (2.50) 5-fluoro-1,3-dimethyl-N-[4'-(prop-1-yn-1-yl)biphenyl-2-yl]–1H-pyrazole-4-carboxamide, (2.51) 2-chloro-N-[4'-(prop-1-yn-1-yl)biphenyl-2-yl]nicotinamide, (2.52) 3-(difluoromethyl)-N-[4'-(3,3-dimethylbut-1-yn-1-yl)biphenyl-2-yl]-1-methyl-1H-pyrazole-4-carboxamide, (2.53) N-[4'-(3,3-dimethylbut-1-yn-1-yl)biphenyl-2-yl]-5-fluoro-1,3-dimethyl-1H-pyrazole-4-carboxamide, (2.54) 3-(difluoromethyl)-N-(4'-ethynylbiphenyl-2-yl)-1-methyl-1H-pyrazole-4-carboxamide, (2.55) N-(4'-ethynylbiphenyl-2-yl)-5-fluoro-1,3-dimethyl-1H-pyrazole-4-carboxamide, (2.56) 2-chloro-N-(4'-ethynylbiphenyl-2-yl)nicotinamide, (2.57) 2-chloro-N-[4'-(3,3-dimethylbut-1-yn-1-yl)biphenyl-2-yl]nicotinamide, (2.58) 4-(difluoromethyl)-2-methyl-N-[4'-(trifluoromethyl)biphenyl-2-yl]-1,3-thiazole-5-carboxamide, (2.59) 5-fluoro-N-[4'-(3-hydroxy-3-methylbut-1-yn-1-yl)biphenyl-2-yl]-1,3-dimethyl-1H-pyrazole-4-carboxamide, (2.60) 2-chloro-N-[4'-(3-hydroxy-3-methylbut-1-yn-1-yl)biphenyl-2-yl]nicotinamide, (2.61) 3-(difluoromethyl)-N-[4'-(3-methoxy-3-methylbut-1-yn-1-yl)biphenyl-2-yl]-1-methyl-1H-pyrazole-4-carboxamide, (2.62) 5-fluoro-N-[4'-(3-methoxy-3-methylbut-1-yn-1-yl)biphenyl-2-yl]-1,3-dimethyl-1H-pyrazole-4-carboxamide, (2.63) 2-chloro-N-[4'-(3-methoxy-3-methylbut-1-yn-1-yl)biphenyl-2-yl]nicotinamide, (2.64) 1,3-dimethyl-N-(1,1,3-trimethyl-2,3-dihydro-1H-inden-4-yl)-1H-pyrazole-4-carboxamide, (2.65) 1,3-dimethyl-N-[(3R)-1,1,3-trimethyl-2,3-dihydro-1H-inden-4-yl]-1H-pyrazole-4-carboxamide, (2.66) 1,3-dimethyl-N-[(3S)-1,1,3-trimethyl-2,3-dihydro-1H-inden-4-yl]-1H-pyrazole-4-carboxamide, (2.67) 3-(difluoromethyl)-N-methoxy-1-methyl-N-[1-(2,4,6-trichlorophenyl)propan-2-yl]-1H-pyrazole-4-carboxamide, (2.68) 3-(difluoromethyl)-N-(7-fluoro-1,1,3-trimethyl-2,3-dihydro-1H-inden-4-yl)-1-methyl-1H-pyrazole-4-carboxamide, (2.69) 3-(difluoromethyl)-N-[(3R)-7-fluoro-1,1,3-trimethyl-2,3-dihydro-1H-inden-4-yl]-1-methyl-1H-pyrazole-4-carboxamide, (2.70) 3-(difluoromethyl)-N-[(3S)-7-fluoro-1,1,3-trimethyl-2,3-dihydro-1H-inden-4-yl]-1-methyl-1H-pyrazole-4-carboxamide.

3) Inhibitors of the respiratory chain on complex III, for example (3.01) ametoctradin, (3.02) amisulbrom, (3.03) azoxystrobin, (3.04) cyazofamid, (3.05) coumethoxystrobin, (3.06) coumoxystrobin, (3.07) dimoxystrobin, (3.08) enoxastrobin, (3.09) famoxadon, (3.10) fenamidon, (3.11) flufenoxystrobin, (3.12) fluoxastrobin, (3.13) kresoxim-methyl, (3.14) metominostrobin, (3.15) orysastrobin, (3.16) picoxystrobin, (3.17) pyraclostrobin, (3.18) pyrametostrobin, (3.19) pyraoxystrobin, (3.20) pyribencarb, (3.21) triclopyricarb, (3.22) trifloxystrobin, (3.23) (2E)-2-(2-{[6-(3-chloro-2-methylphenoxy)-5-fluoropyrimidin-4-yl]oxy}phenyl)-2-(methoxyimino)-N-methylacetamide, (3.24) (2E)-2-(methoxyimino)-N-methyl-2-(2-{[({(1E)-1-[3-(trifluoromethyl)phenyl]ethyliden}amino)oxy]methyl}phenyl)acetamide, (3.25) (2E)-2-(methoxyimino)-N-methyl-2-{2-[(E)-({1-[3-(trifluoromethyl)phenyl]ethoxy}imino)methyl]phenyl}acetamide, (3.26) (2E)-2-{2-[({[(1E)-1-(3-{[(E)-1-fluoro-2-phenylvinyl]oxy}phenyl)ethyliden]amino}oxy)methyl]phenyl}-2-(methoxyimino)-N-methylacetamide, (3.27) fenaminostrobin, (3.28) 5-methoxy-2-methyl-4-(2-{[({(1E)-1-[3-(trifluoromethyl)phenyl]ethyliden}amino)oxy]methyl}phenyl)-2,4-dihydro-3H-1,2,4-triazol-3-one, (3.29) (2E)-2-{2-[({cyclopropyl[(4-methoxy- phenyl)imino]methyl}sulfanyl)methyl]phenyl}-3-methoxyacrylic acid methyl ester, (3.30) N-(3-ethyl-3,5,5-trimethylcyclohexyl)-3-formamido-2-hydroxybenzamide, (3.31) 2-{2-[(2,5-dimethylphe noxy)methyl]phenyl}-2-methoxy-N-methylacetamide, (3.32) 2-{2-[(2,5-dimethylphenoxy)methyl]phenyl}-2-methoxy-N-methylacetamide, (3.33) (2E,3Z)-5-{[1-(4-chlorophenyl)-1H-pyrazol-3-yl]oxy}-2–(methoxyimino)-N,3-dimethylpent-3-enamide.

4) Mitosis and cell division inhibitors, for example (4.01) benomyl, (4.02) carbendazim, (4.03) chlorfenazole, (4.04) diethofencarb, (4.05) ethaboxam, (4.06) fluopicolide, (4.07) fuberidazole, (4.08) pencycuron, (4.09)

thiabendazole, (4.10) thiophanate-methyl, (4.11) thiophanate, (4.12) zoxamide, (4.13) 5-chloro-7-(4-methylpiperidin-1-yl)-6-(2,4,6-trifluorophenyl)[1,2,4]triazolo[1,5-a]pyrimidine, (4.14) 3-chloro-5-(6-chloropyridin-3-yl)-6-methyl-4-(2,4,6-trifluorophenyl)pyridazine.

5) Compounds capable of having multisite action, for example (5.01) Bordeaux mixture, (5.02) captafol, (5.03) captan, (5.04) chlorothalonil, (5.05) copper hydroxide, (5.06) copper naphthenate, (5.07) copper oxide, (5.08) copper oxychloride, (5.09) copper (2+) sulfate, (5.10) dichlofluanid, (5.11) dithianon, (5.12) dodine, (5.13) dodine free base, (5.14) ferbam, (5.15) fluorofolpet, (5.16) folpet, (5.17) guazatine, (5.18) guazatine acetate, (5.19) iminoctadine, (5.20) iminoctadine albesilate, (5.21) iminoctadine triacetate, (5.22) mancopper, (5.23) mancozeb, (5.24) maneb, (5.25) metiram, (5.26) metiram zinc, (5.27) oxine-copper, (5.28) propamidine, (5.29) propineb, (5.30) sulfur and sulfur preparations including calcium polysulfide, (5.31) thiram, (5.32) tolylfluanid, (5.33) zineb, (5.34) ziram, (5.35) anilazine.

6) Compounds capable of inducing host defence, for example (6.01) acibenzolar-S-methyl, (6.02) isotianil, (6.03) probenazole, (6.04) tiadinil, (6.05) laminarin.

7) Amino acid and/or protein biosynthesis inhibitors, for example (7.01) andoprim, (7.02) blasticidin-S, (7.03) cyprodinil, (7.04) kasugamycin, (7.05) kasugamycin hydrochloride hydrate, (7.06) mepanipyrim, (7.07) pyrimethanil, (7.08) 3-(5-fluoro-3,3,4,4-tetramethyl-3,4-dihydroisoquinolin-1-yl)quinoline, (7.09) oxytetracycline, (7.10) streptomycin.

8) ATP production inhibitors, for example (8.01) fentin acetate, (8.02) fentin chloride, (8.03) fentin hydroxide, (8.04) silthiofam.

9) Cell wall synthesis inhibitors, for example (9.01) benthiavalicarb, (9.02) dimethomorph, (9.03) flumorph, (9.04) iprovalicarb, (9.05) mandipropamide, (9.06) polyoxins, (9.07) polyoxorim, (9.08) validamycin A, (9.09) valifenalate, (9.10) polyoxin B, (9.11) (2E)-3-(4-tert-butylphenyl)-3-(2-chloropyridin-4-yl)-1-(morpholin-4-yl)prop-2-en-1-one, (9.12) (2Z)-3-(4-tert-butylphenyl)-3-(2-chloropyridin-4-yl)-1-(morpholin-4-yl)prop-2-en-1-one.

10) Lipid and membrane synthesis inhibitors, for example (10.01) biphenyl, (10.02) chloroneb, (10.03) dicloran, (10.04) edifenphos, (10.05) etridiazole, (10.06) iodocarb, (10.07) iprobenfos, (10.08) isoprothiolane, (10.09) propamocarb, (10.10) propamocarb hydrochloride, (10.11) prothiocarb, (10.12) pyrazophos, (10.13) quintozene, (10.14) tecnazene, (10.15) tolclofos-methyl.

11) Melanin biosynthesis inhibitors, for example (11.01) carpropamide, (11.02) diclocymet, (11.03) fenoxanil, (11.04) phthalide, (11.05) pyroquilon, (11.06) tricyclazole, (11.07) 2,2,2-trifluoroethyl {3-methyl-1-[(4-methylbenzoyl)amino]butan-2-yl}carbamate.

12) Nucleic acid synthesis inhibitors, for example (12.01) benalaxyl, (12.02) benalaxyl-M (kiralaxyl), (12.03) bupirimate, (12.04) clozylacon, (12.05) dimethirimol, (12.06) ethirimol, (12.07) furalaxyl, (12.08) hymexazole, (12.09) metalaxyl, (12.10) metalaxyl-M (mefenoxam), (12.11) ofurace, (12.12) oxadixyl, (12.13) oxolinic acid, (12.14) octhilinone.

13) Signal transduction inhibitors, for example (13.01) chlozolinate, (13.02) fenpiclonil, (13.03) fludioxonil, (13.04) iprodione, (13.05) procymidone, (13.06) quinoxyfen, (13.07) vinclozolin, (13.08) proquinazid.

14) Compounds capable of acting as uncouplers, for example (14.01) binapacryl, (14.02) dinocap, (14.03) ferimzone, (14.04) fluazinam, (14.05) meptyldinocap.

15) Further compounds, for example (15.001) benthiazole, (15.002) bethoxazin, (15.003) capsimycin, (15.004) carvone, (15.005) quinomethionate, (15.006) pyriofenone (chlazafenone), (15.007) cufraneb, (15.008) cyflufenamid, (15.009) cymoxanil, (15.010) cyprosulfamide, (15.011) dazomet, (15.012) debacarb, (15.013) dichlorophen, (15.014) diclomezin, (15.015) difenzoquat, (15.016) difenzoquat metilsulfate, (15.017) diphenylamine, (15.018) ecomate, (15.019) fenpyrazamine, (15.020) flumetover, (15.021) fluoroimide, (15.022) flusulfamide, (15.023) flutianil, (15.024) fosetyl-aluminium, (15.025) fosetyl-calcium, (15.026) fosetyl-sodium, (15.027) hexachlorobenzene, (15.028) irumamycin, (15.029) methasulfocarb, (15.030) methyl isothiocyanate, (15.031) metrafenone, (15.032) mildiomycin, (15.033) natamycin, (15.034) nickel dimethyldithiocarbamate, (15.035) nitrothal-isopropyl, (15.036) oxamocarb, (15.037) oxyfenthiin, (15.038) pentachlorophenol and salts, (15.039) phenothrin, (15.040) phosphorous acid and salts thereof, (15.041) propamocarb-fosetylate, (15.042) propanosin-sodium, (15.043) pyrimorph, (15.044) pyrrolnitrin, (15.045) tebufloquin, (15.046) tecloftalam, (15.047) tolnifanid, (15.048) triazoxide, (15.049) trichlamid, (15.050) zarilamid, (15.051) 2-methylpropanoic acid (3S,6S,7R,8R)-8-benzyl-3-[({3-[(isobutyryloxy)methoxy]-4-methoxypyridin-2-yl}carbonyl)amino]-6-methyl-4,9-dioxo-1,5-dioxonan-7-yl ester, (15.052) 1-(4-{4-[(5R)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, (15.053) 1-(4-{4-[(5S)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl] ethanone, (15.054) oxathiapiproline, (15.055) 1H-imidazole-1-carboxylic acid 1-(4-methoxyphenoxy)-3,3-dimethylbutan-2-yl ester, (15.056) 2,3,5,6-tetrachloro-4-(methylsulfonyl)pyridine, (15.057) 2,3-dibutyl-6-chlorothieno[2,3-d]pyrimidin-4(3H)-one, (15.058) 2,6-dimethyl-1H,5H-[1,4]dithiino[2,3-c:5,6-c']dipyrrole-1,3,5,7(2H,6H)-tetrone, (15.059) 2-[5-methyl-3-(trifluoromethyl)-1H-pyrazol-1-yl]-1-(4-{4-[(5R)-5-phenyl-4,5-dihydro-1,2-oxazol-3-yl]-1,3-thiazol-2-yl}piperidin-1-yl)ethanone, (15.060) 2-[5-methyl-3-(trifluoromethyl)-1H-pyrazol-1-yl]-1-(4-{4-[(5S)-5-phenyl-4,5-dihydro-1,2-oxazol-3-yl]-1,3-thiazol-2-yl}piperidin-1-yl)ethanone, (15.061) 2-[5-methyl-3-(trifluoromethyl)-1H-pyrazol-1-yl]-1-{4-[4-(5-phenyl-4,5-dihydro-1,2-oxazol-3-yl)-1,3-thiazol-2-yl]piperidin-1-yl}ethanone, (15.062) 2-butoxy-6-iodo-3-propyl-4H-chromen-4-one, (15.063) 2-chloro-5-[2-chloro-1-(2,6-difluoro-4-methoxyphenyl)-4-methyl-1H-imidazol-5-yl]pyridine, (15.064) 2-phenylphenol and salts, (15.065) 3-(4,4,5-trifluoro-3,3-dimethyl-3,4-dihydroisoquinolin-1-yl)quinoline, (15.066) 3,4,5-trichloropyridine-2,6-dicarboxylic acid nitrile, (15.067) 3-chloro-5-(4-chlorophenyl)-4-(2,6-difluorophenyl)-6-methylpyridazine, (15.068) 4-(4-chlorophenyl)-5-(2,6-difluorophenyl)-3,6-dimethylpyridazine, (15.069) 5-amino-1,3,4-thiadiazole-2-thiol, (15.070) 5-chloro-N'-phenyl-N'-(prop-2-in-1-yl)thiophene-2-sulfonohydrazide, (15.071) 5-fluoro-2-[(4-fluorobenzyl)oxy]pyrimidin-4-amine, (15.072) 5-fluoro-2-[(4-methylbenzyl)oxy]pyrimidin-4-amin, (15.073) 5-methyl-6-octyl[1,2,4]triazolo[1,5-a]pyrimidin-7-amin, (15.074) (2Z)-3-amino-2-cyano-3-phenylacrylic acid ethyl ester, (15.075) N'-(4-{[3-(4-chlorobenzyl)-1,2,4-thiadiazol-5–yl]oxy}-2,5-dimethylphenyl)-N-ethyl-N-methylimidoformamide, (15.076) N-(4-chlorobenzyl)-3-[3-methoxy-4-(prop-2-in-1-yloxy)phenyl]propanamide, (15.077) N-[(4-chlorophenyl)(cyano)methyl]-3–[3-methoxy-4-(prop-2-in-1-yloxy)phenyl]propanamide, (15.078) N-[(5-bromo-3-chloropyridin-2-yl)methyl]-2,4-dichloronicotinamide, (15.079) N-[1-(5-bromo-3-chloropyridin-2-yl)ethyl]-2,4-dichloronicotinamide, (15.080) N-[1-(5-bromo-3-chloropyridin-2-yl)ethyl]-2-fluoro-4-iodonicotinamide, (15.081) N-{(E)-[(cyclopropylmethoxy)imino][6-(difluoromethoxy)-2,3-difluorophenyl]methyl}-2-phenylacetamide, (15.082) N—{(Z)-[(cyclopropylmethoxy)imino][6-(difluoromethoxy)-2,3-difluorophenyl]methyl}-2-phenylacetamide, (15.083) N'-{4-[(3-tert-butyl-4-cyano-1,2-thiazol-5-yl)oxy]-2-chloro-5-methylphenyl}-N-ethyl-N-methylimidoformamide, (15.084) N-methyl-2-(1-{[5-methyl-3-(trifluoromethyl)-1H-pyrazol-1-yl]acetyl}piperidin-4-yl)-N-(1,2,3,4-tetrahydronaphthalin-1-yl)-1,3-thiazole-4-carboxamide, (15.085) N-methyl-2-(1-{[5-methyl-3-(trifluoromethyl)–1H-pyrazol-1-yl]acetyl}piperidin-4-yl)-N-[(1R)-1,2,3,4-tetrahydronaphthalin-1-yl]-1,3-thiazole-4-carboxamide, (15.086) N-methyl-2-(1-{[5-methyl-3-(trifluoromethyl)-1H-pyrazol-1-yl]acetyl}piperidin-4-yl)-N-[(1S)-1,2,3,4-tetrahydronaphthalin-1-yl]-1,3-thiazole-4-carboxamide, (15.087) {6-[({[(1-methyl-1H-tetrazol-5-yl)(phenyl)methylen]amino}oxy)methyl]pyridin-2-yl}carbamic acid pentyl ester, (15.088) phenazine-1-carboxylic acid, (15.089) quinolin-8-ol, (15.090) quinolin-8-ol sulfate (2:1), (15.091) {6-[({[(1-methyl-1H-tetrazol-5-yl)(phenyl)methylen]amino}oxy)methyl]pyridin-2-yl}carbamic acid tert-butyl ester, (15.092) (5-bromo-2-methoxy-4-methylpyridin-3-yl)(2,3,4-trimethoxy-6-methylphenyl)methanone, (15.093) N-[2-(4-{[3-(4-chlorophenyl)prop-2-yn-1-yl]oxy}-3-methoxyphenyl)ethyl]-N2-(methylsulfonyl)valinamide, (15.094) 4-oxo-4-[(2-phenylethyl)amino]butanoic acid, (15.095) {6-[({[(Z)-(1-methyl-1H-tetrazol-5-yl)(phenyl)methylen]amino}oxy)methyl]pyridin-2-yl}carbamic acid but-3-yn-1-yl ester, (15.096) 4-amino-5-fluoropyrimidin-2-ol (tautomeric form: 4-amino-5-fluoropyrimidin–2(1H)-one), (15.097) propyl 3,4,5-trihydroxybenzoate, (15.098) [3-(4-chloro-2-fluorophenyl)-5-(2,4-difluorophenyl)-1,2-oxazol-4-yl](pyridin-3-yl)methanol, (15.099) (S)-[3-(4-chloro-2-fluorophenyl)-5-(2,4-difluorophenyl)-1,2-oxazol-4-yl](pyridin-3-yl)methanol, (15.100) (R)-[3-(4-chloro-2-fluorophenyl)-5-(2,4-difluorophenyl)-1,2-oxazol-4-yl](pyridin-3-yl)methanol, (15.101) 2-fluoro-6-(trifluoromethyl)-N-(1,1,3-trimethyl-2,3-dihydro-1H-inden-4-yl)benzamide, (15.102) 2-(6-benzylpyridin-2-yl)quinazoline, (15.103) 2-[6-(3-fluoro-4-methoxyphenyl)-5-methylpyridin-2-yl]quinazoline, (15.104) 3-(4,4-difluoro-3,3-dimethyl-3,4-dihydroisoquinolin-1-yl)quinoline, (15.105) abscisic acid, (15.106) N'-[5-bromo-6-(2,3-dihydro-1H-inden-2-yloxy)-2-methylpyridin-3-yl]-N-ethyl-N-methylimidoformamide, (15.107) N'-{5-bromo-6-[1-(3,5-difluorophenyl)ethoxy]-2-methylpyridin-3-yl}-N-ethyl-N-methylimidoformamide, (15.108) N'-{5-bromo-6-[(1R)-1-(3,5-difluorophenyl)ethoxy]-2-methylpyridin-3-yl}-N-ethyl-N-methylimidoformamide, (15.109) N'-{5-bromo-6-[(1S)-1-(3,5-difluorophenyl)ethoxy]-2-methylpyridin-3-yl}-N-ethyl-N-methylimidoformamide, (15.110) N'-{5-bromo-6-[(cis-4-isopropylcyclohexyl)oxy]-2-methylpyridin-3-yl}-N-ethyl-N-methylimidoformamide, (15.111) N'-{5-bromo-6-[(trans-4-isopropylcyclohexyl)oxy]-2-methylpyridin-3-yl}-N-ethyl-N-methylimidoformamide, (15.112) N-cyclopropyl-3-(difluoromethyl)-5-fluoro-N-(2-isopropylbenzyl)-1-methyl-1H-pyrazole-4-carboxamide, (15.113) N-cyclopropyl-N-(2-cyclopropylbenzyl)-3-(difluoromethyl)-5-fluoro-1-methyl-1H-pyrazole-4-carboxamide, (15.114) N-(2-tert-butylbenzyl)-N-cyclopropyl-3–(difluoromethyl)-5-fluoro-1-methyl-1H-pyrazole-4-carboxamide, (15.115) N-(5-chloro-2-ethylbenzyl)-N-cyclopropyl-3-(difluoromethyl)-5-fluoro-1-methyl-1H-pyrazole-4-carboxamide, (15.116) N-(5-chloro-2-isopropylbenzyl)-N-cyclopropyl-3-(difluoromethyl)-5-fluoro-1-methyl-1H-pyrazole-4-carboxamide, (15.117) N-cyclopropyl-3-(difluoromethyl)-N-(2-ethyl-5-fluorobenzyl)-5-fluoro-1-methyl-1H-pyrazole-4-carboxamide, (15.118) N-cyclopropyl-3-(difluoromethyl)-5-fluoro-N-(5-fluoro-2-isopropylbenzyl)-1-methyl-1H-pyrazole-4-carboxamide, (15.119) N-cyclopropyl-N-(2-cyclopropyl-5-fluorobenzyl)-3-(difluoromethyl)-5-fluoro-1-methyl-1H-pyrazole-4-carboxamide, (15.120) N-(2-cyclopentyl-5-fluorobenzyl)-N-cyclopropyl-3-(difluoromethyl)-5-fluoro-1-methyl-1H-pyrazole-4-carboxamide, (15.121) N-cyclopropyl-3-(difluoromethyl)-5-fluoro-N-(2-fluoro-6-isopropylbenzyl)-1-methyl-1H-pyrazole-4-carboxamide, (15.122) N-cyclopropyl-3-(difluoromethyl)-N-(2-ethyl-5-methylbenzyl)-5-fluoro-1-methyl-1H-pyrazole-4-carboxamide, (15.123) N-cyclopropyl-3-(difluoromethyl)-5-fluoro-N-(2-isopropyl-5-methylbenzyl)-1-methyl-1H-pyrazole-4-carboxamide, (15.124) N-cyclopropyl-N-(2-cyclopropyl-5-methylbenzyl)-3-(difluoromethyl)-5-fluoro-1-methyl-1H-pyrazole-4-carboxamide, (15.125) N-(2-tert-butyl-5-methylbenzyl)-N-cyclopropyl-3-(difluoromethyl)-5-fluoro-1-methyl-1H-pyrazole-4-carboxamide, (15.126) N-[5-chloro-2-(trifluoromethyl)benzyl]-N-cyclopropyl-3-(difluoromethyl)-5-fluoro-1-methyl-1H-pyrazole-4-carboxamide, (15.127) N-cyclopropyl-3-(difluoromethyl)-5-fluoro-1-methyl-N-[5-methyl-2-(trifluoromethyl)benzyl]-1H-pyrazole-4-carboxamide, (15.128) N-[2-chloro-6-(trifluoromethyl)benzyl]-N-cyclopropyl-3-(difluoromethyl)-5-fluoro-1-methyl-1H-pyrazole-4-carboxamide, (15.129) N-[3-chloro-2-fluoro-6-(trifluoromethyl)benzyl]-N-cyclopropyl-3-(difluoromethyl)-5-fluoro-1-methyl-1H-pyrazole-4-carboxamide, (15.130) N-cyclopropyl-3-(difluoromethyl)-N-(2-ethyl-4,5-dimethylbenzyl)-5-fluoro-1-methyl-1H-pyrazole-4-carboxamide, (15.131) N-cyclopropyl-3-(difluoromethyl)-5-fluoro-N-(2-isopropylbenzyl)-1-methyl–1H-pyrazole-4-carbothioamide, (15.132) N'-(2,5-dimethyl-4-phenoxyphenyl)-N-ethyl-N-methylimidoformamide, (15.133) N'-{4-[(4,5-dichloro-1,3-thiazol-2-yl)oxy]-2,5-dimethylphenyl}-N-ethyl-N-methylimidoformamide, (15.134) N-(4-chloro-2,6-difluorophenyl)-4-(2-chloro-4-fluorophenyl)-1,3-dimethyl-1H-pyrazol-5-amine, (15.135) 9-fluoro-2,2-dimethyl-5-(quinolin-3-yl)–2,3-dihydro-1,4-benzoxazepine, (15.136) 2-{2-fluoro-6-[(8-fluoro-2-methylquinolin-3-yl)oxy]phenyl}propan-2-ol, (15.137) 2-{2-[(7,8-difluoro-2-methylquinolin-3-yl)oxy]-6-fluorophenyl}propan-2-ol, (15.138) 4-(2-chloro-4-fluorophenyl)-N-(2-fluorophenyl)-1,3-dimethyl-1H-pyrazol-5-amine, (15.139) 4-(2-chloro-4-fluorophenyl)-N-(2,6- difluorophenyl)-1,3-dimethyl-1H-pyrazol-5-amine, (15.140) 4-(2-chloro-4-fluorophenyl)-N-(2-chloro-6-fluorophenyl)-1,3-dimethyl-1H-pyrazol-5-amine, (15.141) 4-(2-bromo-4-fluorophenyl)-N-(2-chloro-6-fluorophenyl)-1,3-dimethyl-1H-pyrazol-5-amine, (15.142) N-(2-bromo-6-fluorophenyl)-4-(2-chloro-4-fluorophenyl)-1,3-dimethyl-1H-pyrazol-5-amine, (15.143) 4-(2-bromo-4-fluorophenyl)-N-(2-bromophenyl)-1,3-dimethyl-1H-pyrazol-5-amine, (15.144) 4-(2-bromo-4-fluorophenyl)-N-(2-bromo-6-fluorophenyl)-1,3-dimethyl-1H-pyrazol-5-amine, (15.145) 4-(2-bromo-4-fluorophenyl)-N-(2-chlorophenyl)-1,3-dimethyl-1H-pyrazol-5-amine, (15.146) N-(2-bromophenyl)-4-(2-chloro-4-fluorophenyl)-1,3-dimethyl-1H-pyrazol-5-amine, (15.147) 4-(2-chloro-4-fluorophenyl)-N-(2-chlorophenyl)-1,3-dimethyl-1H-pyrazol-5-amine, (15.148) 4-(2-bromo-4-fluorophenyl)-N-(2,6-difluorophenyl)-1,3-dimethyl-1H-pyrazol-5-amine, (15.149) 4-(2-bromo-4-fluorophenyl)-N-(2-fluorophenyl)-1,3-dimethyl-1H-pyrazol-5-amine, (15.150) N'-(4-{3-[(difluoromethyl)sulfanyl]phenoxy}-2,5-dimethylphenyl)-N-ethyl-N-methylimidoformamide, (15.151) N'-(2,5-dimethyl-4-{3-[(1,1,2,2-tetrafluoroethyl)sulfanyl]phenoxy}phenyl)-N-ethyl-N-methylimidoformamide, (15.152) N'-(2,5-dimethyl-4-{3-[(2,2,2-trifluoroethyl)sulfanyl]phenoxy}phenyl)-N-ethyl-N-methylimidoformamide, (15.153) N'-(2,5-dimethyl-4-{3-[(2,2,3,3-tetrafluoropropyl)sulfanyl]phenoxy}phenyl)-N-ethyl-N-methylimidoformamide, (15.154) N'-(2,5-dimethyl-4-{3-[(pentafluoroethyl)sulfanyl]pheno xy} phen yl)-N-ethyl-N-methylimidoformamide, (15.155) N'-(4-{[3-(difluoromethoxy)phenyl]sulfanyl}-2,5-dimethylphenyl)-N-ethyl-N-methylimidoformamide, (15.156) N'-(2,5-dimethyl-4-{[3-(1,1,2,2-tetrafluoroethoxy)phenyl]sulfanyl}phenyl)-N-ethyl-N-methylimidoformamide, (15.157) N'-(2,5-dimethyl-4-{[3-(2,2,2-trifluoroethoxy)phenyl]sulfanyl}phenyl)-N-ethyl-N-methylimidoformamide, (15.158) N'-(2,5-dimethyl-4-{[3-(2,2,3,3-tetrafluoropropoxy)phenyl]sulfanyl}phenyl)-N-ethyl-N-methylimidoformamide, (15.159) N'-(2,5-dimethyl-4-{[3-(pentafluoroethoxy)phenyl]sulfanyl}phenyl)-N-ethyl-N-methylimidoformamide, (15.160) 2-[3,5-bis(difluoromethyl)-1H-pyrazol-1-yl]-1-[4-(4-{5-[2-(prop-2-yn-1-yloxy)phenyl]-4,5-dihydro-1,2-oxazol-3-yl}-1,3-thiazol-2-yl)piperidin-1-yl]ethanone, (15.161) 2-[3,5-bis(difluoromethyl)-1H-pyrazol-1-yl]-1-[4-(4-{5-[2-fluoro-6-(prop-2-yn-1-yloxy)phenyl]-4,5-dihydro-1,2-oxazol-3-yl}-1,3-thiazol-2-yl)piperidin-1-yl]ethanone, (15.162) 2-[3,5-bis(difluoromethyl)-1H-pyrazol-1-yl]-1-[4-(4-{5-[2-chloro-6-(prop-2-yn-1-yloxy)phenyl]-4,5-dihydro-1,2-oxazol-3-yl}-1,3-thiazol-2-yl)piperidin-1-yl]ethanone, (15.163) 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}phenyl methansulfonate, (15.164) 2-{3-[2-(1-{[3,5-bis(difluoromethyl)–1H-pyrazol-1-yl]acetyl}piperidin-4-yl)-1,3-thiazol-4-yl]-4,5-dihydro-1,2-oxazol-5-yl}-3-chlorophenyl methansulfonate, (15.165) 2-[3,5-bis(difluoromethyl)-1H-pyrazol-1-yl]-1-[4-(4-{(5S)-5-[2-(prop-2-yn-1-yloxy)phenyl]-4,5-dihydro-1,2-oxazol-3-yl}-1,3-thiazol-2-yl)piperidin-1-yl]ethanone, (15.166) 2-[3,5-bis(difluoromethyl)-1H-pyrazol-1-yl]-1-[4-(4-{(5R)-5-[2-(prop-2-yn-1-yloxy)phenyl]-4,5-dihydro-1,2-oxazol-3-yl}-1,3-thiazol-2-yl)piperidin-1-yl]ethanone, (15.167) 2-[3,5-bis(difluoromethyl)-1H-pyrazol-1-yl]-1-[4-(4-{(5 S)-5-[2-fluoro-6-(prop-2-yn-1-yloxy)phenyl]-4,5-dihydro-1,2-oxazol-3-yl}-1,3-thiazol-2-yl)piperidin-1-yl]ethanone, (15.168) 2-[3,5-bis(difluoromethyl)-1H-pyrazol-1-yl]-1-[4-(4-{(5R)-5-[2-fluoro-6-(prop-2-yn-1-yloxy)phenyl]-4,5-dihydro-1,2-oxazol-3-yl}-1,3-thiazol-2-yl)piperidin-1-yl]etha none, (15.169) 2-[3,5-bis(difluoromethyl)-1H-pyrazol-1-yl]-114-(4-{(5S)-5-[2-chloro-6-(prop-2-yn-1-yloxy)phenyl]-4,5-dihydro-1,2-oxazol-3-yl}-1,3-thiazol-2-yl)piperidin-1-yl]ethanone, (15.170) 2-[3,5-bis(difluoromethyl)-1H-pyrazol-1-yl]-1-[4-(4-{(5R)-5-[2-chloro-6-(prop-2-yn-1-yloxy)phenyl]-4,5-dihydro-1,2-oxazol-3-yl}-1,3-thiazol-2-yl)piperidin-1-yl]ethanone, (15. 171) 2-{(5S)-3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}phenyl methanesulfonate, (15.172) 2-{(5R)-3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}phenyl methanesulfonate, (15.173) 2-{(5S)-3-[2-(1-{[3,5-bis(difluo romethyl)-1H-pyrazol-1-yl]acetyl}piperidin-4-yl)-1,3-thiazol-4-yl]-4,5-dihydro-1,2-oxazol-5-yl}-3-chlorophenyl methanesulfonate, (15.174) 2-{(5R)-3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl methanesulfonate.

Biological Pesticides as Mixing Components

The compounds of the formula (I) can be combined with biological pesticides.

Biological pesticides include especially bacteria, fungi, yeasts, plant extracts and products formed by microorganisms, including proteins and secondary metabolites.

Biological pesticides include bacteria such as spore-forming bacteria, root-colonizing bacteria and bacteria which act as biological insecticides, fungicides or nematicides.

Examples of such bacteria which are used or can be used as biological pesticides are:

*Bacillus amyloliquefaciens*, strain FZB42 (DSM 231179), or *Bacillus cereus*, especially *B. cereus* strain CNCM I-1562 or *Bacillus firmus*, strain 1-1582 (Accession number CNCM I-1582) or *Bacillus pumilus*, especially strain GB34 (Accession No. ATCC 700814) and strain QST2808 (Accession No. NRRL B-30087), or *Bacillus subtilis*, especially strain GB03 (Accession No. ATCC SD-1397), or *Bacillus subtilis* strain QST713 (Accession No. NRRL B-21661) or *Bacillus subtilis* strain OST 30002 (Accession No. NRRL B-50421) *Bacillus thuringiensis*, especially *B. thuringiensis* subspecies *israelensis* (serotype H-14), strain AM65-52 (Accession No. ATCC 1276), or *B. thuringiensis* subsp. *aizawai*, especially strain ABTS-1857 (SD-1372), or *B. thuringiensis* subsp. *kurstaki* strain HD-1, or *B. thuringiensis* subsp. *tenebrionis* strain NB 176 (SD-5428), Pasteuria *penetrans*, Pasteuria spp. (Rotylenchulus *reniformis* nematode)-PR3 (Accession Number ATCC SD-5834), *Streptomyces microflavus* strain AQ6121 (=QRD 31.013, NRRL B-50550), *Streptomyces galbus* strain AQ 6047 (Accession Number NRRL 30232).

Examples of fungi and yeasts which are used or can be used as biological pesticides are:

*Beauveria bassiana*, in particular strain ATCC 74040, *Coniothyrium minitans*, in particular strain CON/M/91-8 (Accession No. DSM-9660), Lecanicillium spp., in particular strain HRO LEC 12, Lecanicillium lecanii (formerly known as *Verticillium* lecanii), in particular strain KV01, Metarhizium anisopliae, in particular strain F52 (DSM3884/ATCC 90448), Metschnikowia fructicola, in particular strain NRRL Y-30752, *Paecilomyces* fumosoroseus (new: Isaria fumosorosea), in particular strain IFPC 200613, or strain Apopka 97 (Accession No. ATCC 20874), *Paecilomyces lilacinus*, in particular *P. lilacinus* strain 251 (AGAL 89/030550), *Talaromyces flavus*, in particular strainV117b, *Trichoderma atroviride*, in particular strain SC1 (Accession Number CBS 122089), *Trichoderma harzianum*, in particular *T. harzianum* rifai T39 (Accession Number CNCM I-952).

Examples of viruses which are used or can be used as biological pesticides are:

*Adoxophyes orana* (summer fruit *tortrix*) granulosis virus (GV), *Cydia pomonella* (codling moth) granulosis virus (GV), *Helicoverpa armigera* (cotton bollworm) nuclear polyhedrosis virus (NPV), *Spodoptera exigua* (beet armyworm) mNPV, *Spodoptera frugiperda* (fall armyworm) mNPV, *Spodoptera littoralis* (African cotton leafworm) NPV.

Also included are bacteria and fungi which are added as 'inoculant' to plants or plant parts or plant organs and which, by virtue of their particular properties, promote plant growth and plant health. Examples include:

*Agrobacterium* spp., *Azorhizobium caulinodans*, Azospirillum spp., *Azotobacter* spp., *Bradyrhizobium* spp., *Burkholderia* spp., especially *Burkholderia cepacia* (formerly known as *Pseudomonas cepacia*), *Gigaspora* spp., or *Gigaspora monosporum*, *Glomus* spp., *Laccaria* spp., *Lactobacillus buchneri*, *Paraglomus* spp., *Pisolithus* tinctorus, *Pseudomonas* spp., *Rhizobium* spp., especially *Rhizobium trifolii*, *Rhizopogon* spp., *Scleroderma* spp., *Suillus* spp., *Streptomyces* spp.

Examples of plant extracts and products formed by microorganisms, including proteins and secondary metabolites, which are used or can be used as biological pesticides are:

*Allium sativum, Artemisia absinthium*, azadirachtin, Biokeeper WP, *Cassia nigricans, Celastrus angulatus, Chenopodium anthelminticum*, chitin, Armour-Zen, *Dryopteris filix-mas, Equisetum arvense*, Fortune *Aza*, Fungastop, Heads Up (*Chenopodium quinoa* saponin extract), pyrethrum/pyrethrins, *Quassia amara, Quercus, Quillaja, Regalia*, "Requiem™ Insecticide", rotenone, ryania/ryanodine, *Symphytum officinale, Tanacetum vulgare*, thymol, Triact 70, TriCon, *Tropaeulum majus, Urtica dioica*, Veratrin, *Viscum album*, Brassicaceae extract, especially oilseed rape powder or mustard powder.

Safeners as Mixing Components

The compounds of the formula (I) can be combined with safeners, for example benoxacor, cloquintocet (-mexyl), cyometrinil, cyprosulfamide, dichlormid, fenchlorazole (-ethyl), fenclorim, flurazole, fluxofenim, furilazole, isoxadifen (-ethyl), mefenpyr (-diethyl), naphthalic anhydride, oxabetrinil, 2-methoxy-N-({4-[(methylcarbamoyl) amino]phenyl}sulfonyl)benzamide (CAS 129531-12-0), 4-(dichloroacetyl)-1-oxa-4-azaspiro[4.5]decane (CAS 715-26-07-3), 2,2,5-trimethyl-3-(dichloroacetyl)-1,3-oxazolidine (CAS 52836-31-4).

Plants and Plant Parts

All plants and plant parts can be treated in accordance with the invention. Plants are understood here to mean all plants and populations of plants, such as desirable and undesirable wild plants or crop plants (including naturally occurring crop plants), for example cereals (wheat, rice, triticale, barley, rye, oats), maize, soya bean, potato, sugar beet, sugar cane, tomatoes, bell peppers and chilli peppers, cucumbers, melons, carrots, water melons, onions, lettuce, spinach, leeks, beans, *Brassica oleracea* (e.g. cabbage) and other vegetable species, cotton, tobacco, oilseed rape, and also fruit plants (with the fruits apples, pears, citrus fruits and grapes). Crop plants may be plants which can be obtained by conventional breeding and optimization methods or by biotechnological and genetic engineering methods or combinations of these methods, including the transgenic plants and including the plant cultivars which are protectable or non-protectable by plant breeders' rights. Plants shall be understood to mean all developmental stages of the plants, for example seeds, cuttings and young (immature) plants up to mature plants. Plant parts shall be understood to mean all parts and organs of the plants above and below ground, such as shoot, leaf, flower and root, examples given being leaves, needles, stalks, stems, flowers, fruit bodies, fruits and seeds, and also roots, tubers and rhizomes. Plant parts also include harvested material (harvested plants or plant parts) and vegetative and generative propagation material, for example cuttings, tubers, rhizomes, slips and seeds.

Treatment according to the invention of the plants and plant parts with the compounds of the formula (I) is carried out directly or by allowing the compounds to act on their surroundings, habitat or storage space by the customary treatment methods, for example by immersion, spraying, evaporation, fogging, scattering, painting on, injection and, in the case of propagation material, in particular in the case of seeds, also by applying one or more coats.

As already mentioned above, it is possible to treat all plants and parts thereof in accordance with the invention. In a preferred embodiment, wild plant species and plant cultivars, or those obtained by conventional biological breeding methods, such as crossing or protoplast fusion, and parts thereof, are treated. In a further preferred embodiment, transgenic plants and plant cultivars obtained by genetic engineering methods, if appropriate in combination with conventional methods (genetically modified organisms), and parts thereof are treated. The term "parts" or "parts of plants" or "plant parts" has been explained above. Particular preference is given in accordance with the invention to treating plants of the respective commercially customary plant cultivars or those that are in use. Plant cultivars are understood to mean plants having new properties ("traits") which have been grown by conventional breeding, by mutagenesis or by recombinant DNA techniques. They may be cultivars, varieties, biotypes or genotypes.

Transgenic Plants, Seed Treatment and Integration Events

The preferred transgenic plants or plant cultivars (those obtained by genetic engineering) which are to be treated in accordance with the invention include all plants which, through the genetic modification, received genetic material which imparts particular advantageous useful properties ("traits") to these plants. Examples of such properties are better plant growth, increased tolerance to high or low temperatures, increased tolerance to drought or to levels of water or soil salinity, enhanced flowering performance, easier harvesting, accelerated ripening, higher harvest yields, higher quality and/or higher nutritional value of the harvested products, better capability for storage and/or processability of the harvested products. Further and particularly emphasized examples of such properties are increased resistance of the plants against animal and microbial pests, such as insects, arachnids, nematodes, mites, slugs and snails owing, for example, to toxins formed in the plants, in particular those produced in the plants by the genetic material from *Bacillus thuringiensis* (for example by the genes CryIA(a), CryIA(b), CryIA(c), CryIIIA, CryIIIA, CryIIIB2, Cry9c, Cry2Ab, Cry3Bb and CryIF and also combinations thereof), and also increased resistance of the plants against phytopathogenic fungi, bacteria and/or viruses caused, for example, by systemic acquired resistance (SAR), systemin, phytoalexins, elicitors and resistance genes and correspondingly expressed proteins and toxins, and also increased tolerance of the plants to certain herbicidally active compounds, for example imidazolinones, sulfonylureas, glyphosates or phosphinothricin (for example the "PAT" gene). The genes which impart the desired properties ("traits") in question may also be present in combinations with one another in the transgenic plants. Examples of transgenic plants mentioned include the important crop plants, such as cereals (wheat, rice, triticale, barley, rye, oats), maize, soybeans, potatoes, sugar beet, sugar cane, tomatoes, peas and other types of vegetable, cotton, tobacco, oilseed rape and also fruit plants (with the fruits apples, pears, citrus fruits and grapevines), particular emphasis being given to maize, soybeans, wheat, rice, potatoes, cotton, sugar cane, tobacco and oilseed rape. Properties ("traits") which are particularly emphasized are the increased resistance of the plants to insects, arachnids, nematodes and slugs and snails.

Crop Protection—Types of Treatment

The plants and plant parts are treated with the compounds of the formula (I) directly or by action on their surroundings, habitat or storage space using customary treatment methods, for example by dipping, spraying, atomizing, irrigating, evaporating, dusting, fogging, broadcasting, foaming, painting, spreading-on, injecting, watering (drenching), drip irrigating and, in the case of propagation material, in particular in the case of seed, additionally by dry seed treatment, liquid seed treatment, slurry treatment, by incrusting, by coating with one or more coats, etc. It is furthermore possible to apply the compounds of the formula (I) by the ultra-low volume method or to inject the application form or the compound of the formula (I) itself into the soil.

A preferred direct treatment of the plants is foliar application, i.e. compounds of the formula (I) are applied to the foliage, where treatment frequency and the application rate should be adjusted according to the level of infestation with the pest in question.

In the case of systemically active compounds, the compounds of the formula (I) also access the plants via the root system. The plants are then treated by the action of the compounds of the formula (I) on the habitat of the plant. This can be accomplished, for example, by drenching, or by mixing into the soil or the nutrient solution, meaning that the locus of the plant (e.g. soil or hydroponic systems) is impregnated with a liquid form of the compounds of the formula (I), or by soil application, meaning that the compounds of the formula (I) are introduced in solid form (e.g. in the form of granules) into the locus of the plants. In the case of paddy rice crops, this can also be accomplished by metering the compound of the formula (I) in a solid application form (for example as granules) into a flooded paddy field.

Seed Treatment

The control of animal pests by the treatment of the seed of plants has long been known and is the subject of constant improvements. Nevertheless, the treatment of seed entails a series of problems which cannot always be solved in a satisfactory manner. Thus, it is desirable to develop methods for protecting the seed and the germinating plant which dispense with, or at least reduce considerably, the additional application of pesticides during storage, after sowing or after emergence of the plants. It is additionally desirable to optimize the amount of active ingredient used so as to provide optimum protection for the seed and the germinating plant from attack by animal pests, but without damage to the plant itself by the active ingredient used. In particular, methods for the treatment of seed should also take account of the intrinsic insecticidal or nematicidal properties of pest-resistant or -tolerant transgenic plants in order to achieve optimal protection of the seed and the germinating plant with a minimum expenditure on pesticides.

The present invention therefore in particular also relates to a method for the protection of seed and germinating plants from attack by pests, by treating the seed with one of the compounds of the formula (I). The method according to the invention for protecting seed and germinating plants against attack by pests further comprises a method in which the seed is treated simultaneously in one operation or sequentially with a compound of the formula (I) and a mixing component. It further also comprises a method where the seed is treated at different times with a compound of the formula (I) and a mixing component.

The invention likewise relates to the use of the compounds of the formula (I) for the treatment of seed for protecting the seed and the resulting plant from animal pests.

The invention further relates to seed which has been treated with a compound of the formula (I) for protection from animal pests. The invention also relates to seed which has been treated simultaneously with a compound of the formula (I) and a mixing component. The invention further relates to seed which has been treated at different times with a compound of the formula (I) and a mixing component. In the case of seed which has been treated at different times with a compound of the formula (I) and a mixing component, the individual substances may be present on the seed in different layers. In this case, the layers comprising a compound of the formula (I) and a mixing component may optionally be separated by an intermediate layer. The invention also relates to seed in which a compound of the formula (I) and a mixing component have been applied as part of a coating or as a further layer or further layers in addition to a coating.

The invention further relates to seed which, after the treatment with a compound of the formula (I), is subjected to a film-coating process to prevent dust abrasion on the seed.

One of the advantages encountered with a systemically acting compound of the formula (I) is the fact that, by treating the seed, not only the seed itself but also the plants resulting therefrom are, after emergence, protected against animal pests. In this way, the immediate treatment of the crop at the time of sowing or shortly thereafter can be dispensed with.

A further advantage is that the treatment of the seed with a compound of the formula (I) can enhance germination and emergence of the treated seed.

It is likewise considered to be advantageous that compounds of the formula (I) can especially also be used for transgenic seed.

Furthermore, compounds of the formula (I) can be employed in combination with compositions of signalling technology, leading to better colonization by symbionts such as, for example, *rhizobia*, mycorrhizae and/or endophytic bacteria or fungi, and/or to optimized nitrogen fixation.

The compounds of the formula (I) are suitable for the protection of seed of any plant variety which is used in agriculture, in greenhouses, in forests or in horticulture. More particularly, this includes seed of cereals (for example wheat, barley, rye, millet and oats), maize, cotton, soya beans, rice, potatoes, sunflowers, coffee, tobacco, canola, oilseed rape, beet (for example sugar beet and fodder beet), peanuts, vegetables (for example tomatoes, cucumbers, beans, cruciferous vegetables, onions and lettuce), fruit plants, lawns and ornamental plants. Of particular significance is the treatment of the seed of cereals (such as wheat, barley, rye and oats), maize, soya beans, cotton, canola, oilseed rape, vegetables and rice.

As already mentioned above, the treatment of transgenic seed with a compound of the formula (I) is also of particular importance. This involves the seed of plants which generally contain at least one heterologous gene which controls the expression of a polypeptide having insecticidal and/or nematicidal properties in particular. The heterologous genes in transgenic seed may originate in this case from microorganisms such as *Bacillus, Rhizobium, Pseudomonas, Serratia, Trichoderma, Clavibacter, Glomus* or *Gliocladium*. The present invention is particularly suitable for the treatment of transgenic seed containing at least one heterologous gene originating from *Bacillus* sp. The heterologous gene is more preferably derived from *Bacillus thuringiensis*.

In the context of the present invention, the compound of the formula (I) is applied to the seed. The seed is preferably treated in a state in which it is sufficiently stable for no damage to occur in the course of treatment. In general, the seed can be treated at any time between harvest and sowing. It is customary to use seed which has been separated from the plant and freed from cobs, shells, stalks, coats, hairs or the flesh of the fruits. Thus, for example, it is possible to use seed which has been harvested, cleaned and dried down to a moisture content which allows storage. Alternatively, it is also possible to use seed which, after drying, has been treated with, for example, water and then dried again, for example priming. In the case of rice seed, it is also possible to use seed which has been imbibed in water up to a certain stage (pigeon breast stage) for example, which leads to improved germination and more uniform emergence.

When treating the seed, care must generally be taken that the amount of the compound of the formula (I) applied to the seed and/or the amount of further additives is chosen in such a way that the germination of the seed is not adversely affected, or that the resulting plant is not damaged. This has to be ensured particularly in the case of active ingredients which can exhibit phytotoxic effects at certain application rates.

In general, the compounds of the formula (I) are applied to the seed in the form of a suitable formulation. Suitable formulations and processes for seed treatment are known to the person skilled in the art.

The compounds of the formula (I) can be converted to the customary seed-dressing formulations, such as solutions, emulsions, suspensions, powders, foams, slurries or other coating compositions for seed, and also ULV formulations.

These formulations are produced in a known manner, by mixing compounds of the formula (I) with customary additives, for example customary extenders and solvents or diluents, dyes, wetters, dispersants, emulsifiers, antifoams, preservatives, secondary thickeners, stickers, gibberellins and also water.

Dyes which may be present in the seed-dressing formulations usable in accordance with the invention are all dyes which are customary for such purposes. It is possible to use either pigments, which are sparingly soluble in water, or dyes, which are soluble in water. Examples include the dyes known by the names Rhodamine B, C.I. Pigment Red 112 and C.I. Solvent Red 1.

Useful wetting agents which may be present in the seed-dressing formulations usable in accordance with the invention are all substances which promote wetting and which are customary for the formulation of agrochemically active ingredients. Alkyl naphthalenesulfonates, such as diisopropyl or diisobutyl naphthalenesulfonates, can be used with preference.

Suitable dispersants and/or emulsifiers which may be present in the seed-dressing formulations usable in accordance with the invention are all nonionic, anionic and cationic dispersants customary for the formulation of agrochemically active ingredients. Nonionic or anionic dispersants or mixtures of nonionic or anionic dispersants can be used with preference. Suitable nonionic dispersants especially include ethylene oxide/propylene oxide block polymers, alkylphenol polyglycol ethers and tristyrylphenol polyglycol ethers, and the phosphated or sulfated derivatives thereof. Suitable anionic dispersants are especially lignosulfonates, polyacrylic acid salts and arylsulfonate-formaldehyde condensates.

Antifoams which may be present in the seed-dressing formulations usable in accordance with the invention are all foam-inhibiting substances customary for the formulation of agrochemically active ingredients. Silicone antifoams and magnesium stearate can be used with preference.

Preservatives which may be present in the seed-dressing formulations usable in accordance with the invention are all substances usable for such purposes in agrochemical compositions. Examples include dichlorophene and benzyl alcohol hemiformal.

Secondary thickeners which may be present in the seed-dressing formulations usable in accordance with the invention are all substances which can be used for such purposes in agrochemical compositions. Preferred examples include cellulose derivatives, acrylic acid derivatives, xanthan, modified clays and finely divided silica.

Useful stickers which may be present in the seed-dressing formulations usable in accordance with the invention are all customary binders usable in seed-dressing products. Preferred examples include polyvinylpyrrolidone, polyvinyl acetate, polyvinyl alcohol and tylose.

Gibberellins which may be present in the seed-dressing formulations usable in accordance with the invention are preferably the gibberellins A1, A3 (=gibberellic acid), A4 and A7; particular preference is given to using gibberellic acid. The gibberellins are known (cf. R. Wegler "Chemie der Pflanzenschutz-und Schädlingsbekämpfungsmittel", vol. 2, Springer Verlag, 1970, pp. 401-412).

The seed-dressing formulations usable in accordance with the invention can be used to treat a wide variety of different kinds of seed, either directly or after prior dilution with water. For instance, the concentrates or the preparations obtainable therefrom by dilution with water can be used to dress the seed of cereals, such as wheat, barley, rye, oats and triticale, and also the seed of maize, rice, oilseed rape, peas, beans, cotton, sunflowers, soya beans and beets, or else a wide variety of different vegetable seed. The seed-dressing formulations usable in accordance with the invention, or the dilute use forms thereof, can also be used to dress seed of transgenic plants.

For the treatment of seed with the seed-dressing formulations usable in accordance with the invention, or use forms prepared therefrom, all mixing units usable customarily for the seed dressing are useful. Specifically, the procedure in seed dressing is to place the seed into a mixer in batchwise or continuous operation, to add the particular desired amount of seed-dressing formulations, either as such or after prior dilution with water, and to mix until the formulation is distributed homogeneously on the seed. If appropriate, this is followed by a drying operation.

The application rate of the seed dressing formulations usable in accordance with the invention can be varied within a relatively wide range. It is guided by the particular content of the compounds of the formula (I) in the formulations and by the seed. The application rates of the compound of the formula (I) are generally between 0.001 and 50 g per kilogram of seed, preferably between 0.01 and 15 g per kilogram of seed.

Animal Health

In the animal health field, i.e. the field of veterinary medicine, the compounds of the formula (I) are active against animal parasites, in particular ectoparasites or endoparasites. The term "endoparasites" includes especially helminths and protozoa, such as coccidia. Ectoparasites are typically and preferably arthropods, especially insects and acarids.

In the field of veterinary medicine, the compounds of the formula (I) having favourable endotherm toxicity are suitable for controlling parasites which occur in animal breeding and animal husbandry in livestock, breeding animals, zoo animals, laboratory animals, experimental animals and domestic animals. They are active against all or specific stages of development of the parasites.

Agricultural livestock include, for example, mammals such as sheep, goats, horses, donkeys, camels, buffalo, rabbits, reindeer, fallow deer, and particularly cattle and pigs; poultry such as turkeys, ducks, geese, and particularly chickens; fish and crustaceans, for example in aquaculture, and also insects such as bees.

Domestic animals include, for example, mammals, such as hamsters, guinea pigs, rats, mice, chinchillas, ferrets, and particularly dogs, cats, caged birds, reptiles, amphibians and aquarium fish.

In a preferred embodiment, the compounds of the formula (I) are administered to mammals.

In another preferred embodiment, the compounds of the formula (I) are administered to birds, namely caged birds and particularly poultry.

Use of the compounds of the formula (I) for the control of animal parasites is intended to reduce or prevent illness, cases of death and reductions in performance (in the case of meat, milk, wool, hides, eggs, honey and the like), such that more economical and simpler animal husbandry is enabled and better animal well-being is achievable.

In relation to the field of animal health, the term "control" or "controlling" means that the compounds of the formula (I) are effective in reducing the incidence of the particular parasite in an animal infected with such parasites to an innocuous degree. More specifically, "controlling" in the present context means that the compound of the formula (I) can kill the respective parasite, inhibit its growth, or inhibit its proliferation.

Arthropods include:

from the order Anoplurida, for example *Haematopinus* spp., *Linognathus* spp., *Pediculus* spp., Phtirus spp., *Solenopotes* spp.; from the order Mallophagida and the suborders Amblycerina and Ischnocerina, for example *Trimenopon* spp., *Menopon* spp., *Trinoton* spp., *Bovicola* spp., *Werneckiella* spp., *Lepikentron* spp., *Damalina* spp., *Trichodectes* spp., *Felicola* spp.; from the order Diptera and the suborders Nematocerina and Brachycerina, for example *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Odagmia* spp., *Wilhelmia* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp., *Melophagus* spp., *Rhinoestrus* spp., *Tipula* spp.; from the order Siphonapterida, for example *Pulex* spp., *Ctenocephalides* spp., *Tunga* spp., *Xenopsylla* spp., *Ceratophyllus* spp.;

from the order Heteropterida, for example *Cimex* spp., *Triatoma* spp., *Rhodnius* spp., Panstrongylus spp.; and also nuisance and hygiene pests from the order Blattarida.

Arthropods further include:

from the subclass Acari (Acarina) and the order Metastigmata, for example from the family Argasidae like *Argas* spp., *Ornithodorus* spp., *Otobius* spp., from the family Ixodidae like *Ixodes* spp., *Amblyomma* spp., *Rhipicephalus* (*Boophilus*) spp., *Dermacentor* spp., Haemophysalis spp., *Hyalomma* spp., *Rhipicephalus* spp. (the original genus of multi-host ticks); from the order Mesostigmata like *Dermanyssus* spp., *Ornithonyssus* spp., Pneumonyssus spp., Raillietia spp., Pneumonyssus spp., Sternostoma spp., *Varroa* spp., Acarapis spp.; from the order Actinedida (Prostigmata), for example Acarapis spp., *Cheyletiella* spp., Ornithocheyletia spp., *Myobia* spp., Psorergates spp., *Demodex* spp., Trombicula spp., Neotrombicula spp., Listrophorus spp.; and from the order Acaridida (Astigmata), for example *Acarus* spp., Tyrophagus spp., Caloglyphus spp., Hypodectes spp., Pterolichus spp., *Psoroptes* spp., Chorioptes spp., Otodectes spp., *Sarcoptes* spp., Notoedres spp., Knemidocoptes spp., Cytodites spp., Laminosioptes spp.

Parasitic protozoa include:

Mastigophora (*Flagellata*), for example Trypanosomatidae, for example *Trypanosoma b. brucei*, *T. b. gambiense*, *T. b. rhodesiense*, *T. congolense*, *T. cruzi*, *T. evansi*, *T. equinum*, *T. lewisi*, *T. percae*, *T. simiae*, *T. vivax*, *Leishmania brasiliensis*, *L. donovani*, *L. tropica*, for example Trichomonadidae, for example *Giardia lamblia*, *G. canis;*

Sarcomastigophora (Rhizopoda) such as Entamoebidae, for example *Entamoeba histolytica*, Hartmanellidae, for example *Acanthamoeba* sp., Harmanella sp.;

Apicomplexa (Sporozoa) such as Eimeridae, for example Eimeria *acervulina*, *E. adenoides*, *E. alabamensis*, *E. anatis*, *E. anserina*, *E. arloingi*, *E. ashata*, *E. auburnensis*, *E. bovis*, *E. brunetti*, *E. canis*, *E. chinchillae*, *E. clupearum*, *E. columbae*, *E. contorta*, *E. crandalis*, *E. debliecki*, *E. dispersa*, *E. ellipsoidales*, *E. falciformis*, *E. faurei*, *E. flavescens*, *E. gallopavonis*, *E. hagani*, *E. intestinalis*, *E. iroquoina*, *E. irresidua*, *E. labbeana*, *E. leucarti*, *E. magna*, *E. maxima*, *E. media*, *E. meleagridis*, *E. meleagrimitis*, *E. mitis*, *E. necatrix*, *E. ninakohlyakimovae*, *E. ovis*, *E. parva*, *E. pavonis*, *E. perforans*, *E. phasani*, *E. piriformis*, *E. praecox*, *E. residua*, *E. scabra*, E. spec., *E. stiedai*, *E. suis*, *E. tenella*, *E. truncata*, *E. truttae*, *E. zuernii*, Globidium spec., *Isospora belli*, *I. canis*, *I. felis*, *I. ohioensis*, *I. rivolta*, *I. spec.*, *I. suis*, Cystisospora spec., *Cryptosporidium* spec., in particular *C. parvum*; such as Toxoplasmadidae, for example *Toxoplasma gondii*, *Hammondia heydornii*, *Neospora caninum*, *Besnoitia* besnoitii; such as Sarcocystidae, for example *Sarcocystis bovicanis*, *S. bovihominis*, S. ovicanis, S. ovifelis, *S. neurona*, S. spec., *S. suihominis*, such as Leucozoidae, for example *Leucozytozoon simondi*, such as Plasmodiidae, for example *Plasmodium berghei, P. falciparum, P. malariae, P. ovale, P. vivax,* P. spec., such as Piroplasmea, for example *Babesia argentina, B. bovis, B. canis,* B. spec., *Theileria parva, Theileria* spec., such as Adeleina, for example *Hepatozoon canis,* H. spec.

Pathogenic endoparasites which are helminths include Platyhelmintha (e.g. Monogenea, cestodes and trematodes), nematodes, Acanthocephala, and Pentastoma. These include:

Monogenea: for example: *Gyrodactylus* spp., *Dactylogyrus* spp., Polystoma spp.;

Cestodes: from the order of Pseudophyllidea, for example: *Diphyllobothrium* spp., *Spirometra* spp., *Schistocephalus* spp., *Ligula* spp., *Bothridium* spp., Diphlogonoporus spp.;

from the order Cyclophyllida, for example: *Mesocestoides* spp., Anoplocephala spp., Paranoplocephala spp., *Moniezia* spp., Thysanosoma spp., Thysaniezia spp., Avitellina spp., *Stilesia* spp., Cittotaenia spp., Andyra spp., *Bertiella* spp., *Taenia* spp., *Echinococcus* spp., Hydatigera spp., Davainea spp., *Raillietina* spp., *Hymenolepis* spp., *Echinolepis* spp., *Echinocotyle* spp., *Diorchis* spp., *Dipylidium* spp., Joyeuxiella spp., Diplopylidium spp.

Trematodes: from the class of Digenea, for example: *Diplostomum* spp., *Posthodiplostomum* spp., *Schistosoma* spp., *Trichobilharzia* spp., *Ornithobilharzia* spp., *Austrobilharzia* spp., *Gigantobilharzia* spp., *Leucochloridium* spp., *Brachylaima* spp., *Echinostoma* spp., *Echinoparyphium* spp., *Echinochasmus* spp., *Hypoderaeum* spp., *Fasciola* spp., *Fascioloides* spp., *Fasciolopsis* spp., *Cyclocoelum* spp., Typhlocoelum spp., *Paramphistomum* spp., Calicophoron spp., Cotylophoron spp., Gigantocotyle spp., Fischoederius spp., Gastrothylacus spp., *Notocotylus* spp., *Catatropis* spp., *Plagiorchis* spp., *Prosthogonimus* spp., Dicrocoelium spp., Eurytrema spp., Troglotrema spp., Paragonimus spp., Collyriclum spp., Nanophyetus spp., *Opisthorchis* spp., Clonorchis spp., *Metorchis* spp., *Heterophyes* spp., *Metagonimus* spp.;

Nematodes: Trichinellida, for example: Trichuris spp., *Capillaria* spp., Paracapillaria spp., Eucoleus spp., Trichomosoides spp., Trichinella spp.;

from the order Tylenchida, for example: *Micronema* spp., *Strongyloides* spp.;

from the order Rhabditida, for example: *Strongylus* spp., Triodontophorus spp., Oesophagodontus spp., *Trichonema* spp., Gyalocephalus spp., Cylindropharynx spp., Poteriostomum spp., Cyclococercus spp., Cylicostephanus spp., *Oesophagostomum* spp., *Chabertia* spp., *Stephanurus* spp., Ancylostoma spp., *Uncinaria* spp., *Necator* spp., Bunostomum spp., *Globocephalus* spp., Syngamus spp., Cyathostoma spp., Metastrongylus spp., Dictyocaulus spp., Muellerius spp., Protostrongylus spp., Neostrongylus spp., Cystocaulus spp., Pneumostrongylus spp., Spicocaulus spp., Elaphostrongylus spp., Parelaphostrongylus spp., Crenosoma spp., Paracrenosoma spp., Oslerus spp., Angiostrongylus spp., Aelurostrongylus spp., Filaroides spp., Parafilaroides spp., Trichostrongylus spp., Haemonchus spp., Ostertagia spp., Teladorsagia spp., Marshallagia spp., *Cooperia* spp., Nippostrongylus spp., Heligmosomoides spp., Nematodirus spp., Hyostrongylus spp., *Obeliscoides* spp., Amidostomum spp., Ollulanus spp.;

from the order Spirurida, for example: *Oxyuris* spp., Enterobius spp., Passalurus spp., Syphacia spp., Aspiculuris spp., Heterakis spp.; *Ascaris* spp., Toxascaris spp., Toxocara spp., Baylisascaris spp., Parascaris spp., Anisakis spp., Ascaridia spp.; Gnathostoma spp., Physaloptera spp., Thelazia spp., Gongylonema spp., Habronema spp., Parabronema spp., Draschia spp., *Dracunculus* spp.; Stephanofilaria spp., Parafilaria spp., *Setaria* spp., *Loa* spp., *Dirofilaria* spp., Litomosoides spp., Brugia spp., Wuchereria spp., Onchocerca spp., Spirocerca spp.;

Acanthocephala: from the order of Oligacanthorhynchida, for example: *Macracanthorhynchus* spp., *Prosthenorchis* spp.; from the order Polymorphida for example: *Filicollis* spp.; from the order Moniliformida for example: *Moniliformis* spp.;

from the order Echinorhynchida, for example *Acanthocephalus* spp., *Echinorhynchus* spp., *Leptorhynchoides* spp.;

Pentastoma: from the order Porocephalida, for example *Linguatula* spp.

In the veterinary field and in animal husbandry, the compounds of the formula (I) are administered by methods generally known in the art, such as via the enteral, parenteral, dermal or nasal route in the form of suitable preparations. Administration may be prophylactic or therapeutic.

Thus, one embodiment of the present invention refers to the use of a compound of the formula (I) as a medicament.

A further aspect refers to the use of a compound of the formula (I) as an antiendoparasitic agent, in particular a helminthicidal agent or antiprotozoic agent. Compounds of the formula (I) are suitable for use as an antiendoparasitic agent, especially as a helminthicidal agent or antiprotozoic agent, for example in animal breeding, in animal husbandry, in animal houses and in the hygiene sector.

A further aspect in turn relates to the use of a compound of the formula (I) as an antiectoparasitic agent, in particular an arthropodicide such as an insecticide or an acaricide. A further aspect relates to the use of a compound of the formula (I) as an antiectoparasitic agent, in particular an arthropodicide such as an insecticide or an acaricide, for example in animal husbandry, in animal breeding, in animal houses or in the hygiene sector.

Anthelmintic Mixing Components

The following anthelmintic mixing components may be mentioned by way of example:

anthelmintically active compounds including trematicidally and cestocidally active compounds:

from the class of the macrocyclic lactones, for example: abamectin, doramectin, emamectin, eprinomectin, ivermectin, milbemycin, moxidectin, nemadectin, selamectin;

from the class of the benzimidazoles and probenzimidazoles, for example: albendazole, albendazole-sulfoxide, cambendazole, cyclobendazole, febantel, fenbendazole, flubendazole, mebendazole, netobimin, oxfendazole, oxibendazole, parbendazole, thiabendazole, thiophanate, triclabendazole;

from the class of the cyclooctadepsipeptides, for example: emodepside, PF1022;

from the class of the aminoacetonitrile derivatives, for example: monepantel;

from the class of the tetrahydropyrimidines, for example: morantel, pyrantel, oxantel;

from the class of the imidazothiazoles, for example: butamisole, levamisole, tetramisole;

from the class of the salicylanilides, for example: bromoxanide, brotianide, clioxanide, closantel, niclosamide, oxyclozanide, rafoxanide, tribromsalan;

from the class of the paraherquamides, for example: derquantel, paraherquamide;

from the class of the aminophenylamidines, for example: amidantel, deacylated amidantel (dAMD), tribendimidine;

from the class of the organophosphates, for example: coumaphos, crufomate, dichlorvos, haloxone, naphthalofos, trichlorfon;

from the class of the substituted phenols, for example: bithionol, disophenol, hexachlorophene, niclofolan, meniclopholan, nitroxynil;

from the class of the piperazinones, for example: praziquantel, epsiprantel;

from various other classes, for example: amoscanate, bephenium, bunamidine, clonazepam, clorsulon, diamfenetid, dichlorophen, diethylcarbamazine, emetine, hetolin, hycanthone, lucanthone, Miracil, mirasan, niclosamide, niridazole, nitroxynil, nitroscanate, oltipraz, omphalotin, oxamniquin, paromomycin, piperazine, resorantel.

Vector Control

The compounds of the formula (I) can also be used in vector control. In the context of the present invention, a vector is an arthropod, especially an insect or arachnid, capable of transmitting pathogens, for example viruses, worms, single-cell organisms and bacteria, from a reservoir (plant, animal, human, etc.) to a host. The pathogens can be transmitted either mechanically (for example trachoma by non-stinging flies) to a host or after injection (for example malaria parasites by mosquitoes) into a host.

Examples of vectors and the diseases or pathogens they transmit are:

1) Mosquitoes
   *Anopheles*: malaria, filariasis;
   *Culex*: Japanese encephalitis, filariasis, other viral diseases, transmission of worms;
   *Aedes*: yellow fever, dengue fever, filariasis, other viral diseases;
   Simuliidae: transmission of worms, in particular Onchocerca *volvulus;*
2) Lice: skin infections, epidemic typhus;
3) Fleas: plague, endemic typhus;
4) Flies: sleeping sickness (trypanosomiasis); cholera, other bacterial diseases;
5) Mites: acariosis, epidemic typhus, rickettsialpox, tularaemia, Saint Louis encephalitis, tick-borne encephalitis (TBE), Crimean-Congo haemorrhagic fever, borreliosis;
6) Ticks: borellioses such as *Borrelia* duttoni, tick-borne encephalitis, Q fever (*Coxiella burnetii*), babesioses (*Babesia canis canis*).

Examples of vectors in the context of the present invention are insects, such as aphids, flies, leafhoppers or *thrips*, which can transmit plant viruses to plants. Other vectors capable of transmitting plant viruses are spider mites, lice, beetles and nematodes.

Further examples of vectors in the context of the present invention are insects and arachnids such as mosquitoes, especially of the genera *Aedes, Anopheles*, for example *A. gambiae, A. arabiensis, A. funestus, A. dirus* (malaria) and *Culex*, lice, fleas, flies, mites and ticks, which can transmit pathogens to animals and/or humans.

Vector control is also possible if the compounds of the formula (I) are resistance-breaking.

Compounds of the formula (I) are suitable for use in the prevention of diseases and/or pathogens transmitted by vectors. Thus, a further aspect of the present invention is the use of compounds of the formula (I) for vector control, for example in agriculture, in horticulture, in forests, in gardens and in leisure facilities, and also in the protection of materials and stored products.

Protection of Industrial Materials

The compounds of the formula (I) are suitable for protecting industrial materials against attack or destruction by insects, for example from the orders Coleoptera, Hymenoptera, Isoptera, Lepidoptera, Psocoptera and Zygentoma.

Industrial materials in the present context are understood to mean inanimate materials, such as preferably plastics, adhesives, sizes, papers and cards, leather, wood, processed wood products and coating compositions. The use of the invention for protection of wood is particularly preferred.

In a further embodiment, the compounds of the formula (I) are used together with at least one further insecticide and/or at least one fungicide.

In a further embodiment, the compounds of the formula (I) are present as a ready-to-use pesticide, i.e. it can be applied to the material in question without further modifications. Suitable further insecticides or fungicides are in particular those mentioned above.

Surprisingly, it has also been found that the compounds of the formula (I) can be employed for protecting objects which come into contact with saltwater or brackish water, in particular hulls, screens, nets, buildings, moorings and signalling systems, against fouling. It is equally possible to use the compounds of the formula (I), alone or in combinations with other active ingredients, as antifouling agents.

Control of Animal Pests in the Hygiene Sector

The compounds of the formula (I) are suitable for controlling animal pests in the hygiene sector. More particularly, the invention can be used in the domestic protection sector, in the hygiene protection sector and in the protection of stored products, particularly for control of insects, arachnids and mites encountered in enclosed spaces, for example dwellings, factory halls, offices, vehicle cabins. For controlling animal pests, the compounds of the formula (I) are used alone or in combination with other active ingredients and/or auxiliaries. They are preferably used in domestic insecticide products. The compounds of the formula (I) are effective against sensitive and resistant species, and against all developmental stages.

These pests include, for example, pests from the class Arachnida, from the orders Scorpiones, Araneae and Opiliones, from the classes Chilopoda and Diplopoda, from the class Insecta the order Blattodea, from the orders Coleoptera, Dermaptera, Diptera, Heteroptera, Hymenoptera, Isoptera, Lepidoptera, Phthiraptera, Psocoptera, Saltatoria or Orthoptera, Siphonaptera and Zygentoma and from the class Malacostraca the order Isopoda.

Application is carried out, for example, in aerosols, unpressurized spray products, for example pump and atomizer sprays, automatic fogging systems, foggers, foams, gels, evaporator products with evaporator tablets made of cellulose or plastic, liquid evaporators, gel and membrane evaporators, propeller-driven evaporators, energy-free, or passive, evaporation systems, moth papers, moth bags and moth gels, as granules or dusts, in baits for spreading or bait stations.

A further aspect of the invention is the use of a compound of the formula (I) as a herbicide.

Preparation Methods

The compounds according to the invention can be prepared by customary methods known to those skilled in the art.

Reaction scheme 1 shows a general preparation method for the compounds (Ia) and (Ib) according to the invention.

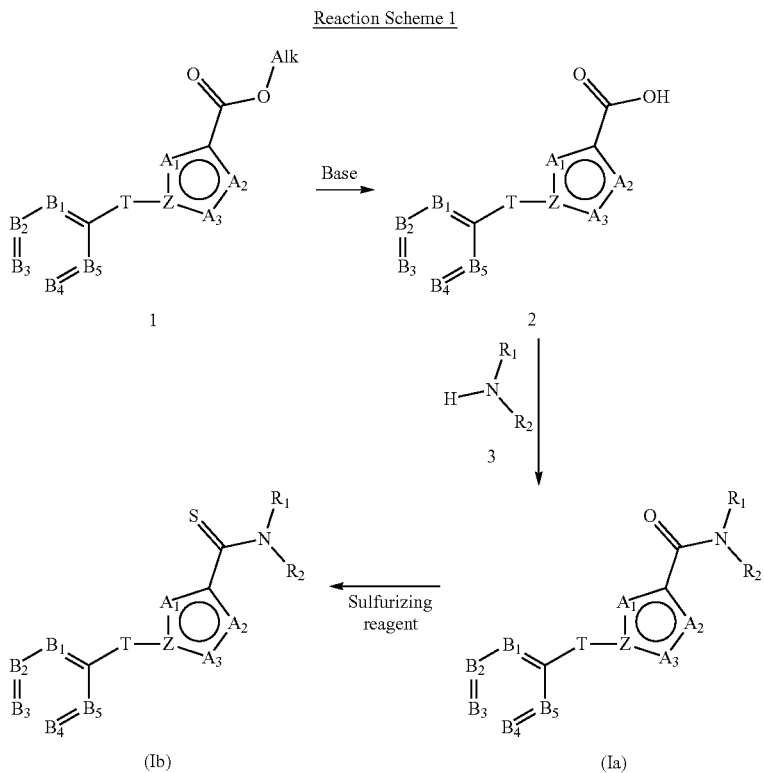

The radicals $A_1$, $A_2$, $A_3$, Z, T, $B_1$, $B_2$, $B_3$, $B_4$, $B_5$, $R_1$, and $R_2$ are defined as described above. Alk is a $C_1$-$C_4$-alkyl.

By activating intermediate 2 and subsequent reaction of the activated intermediate with amines of the general structure 3, compounds according to the invention of the general structure (Ia) can be obtained. For this amidation step, numerous reaction conditions have been described. A summary can be found in Houben-Weyl, Methoden der Organischen Chemie, Volume E5 (Georg Thieme Verlag Stuttgart), p. 934. Some of these reactions proceed via intermediary carbonyl chlorides, which may be used isolated or generated in-situ. The amines of the general structure 3 or salts thereof are commerically available or can be prepared by methods known to those skilled in the art.

The amide function of the compounds according to the invention of the general structure (Ia) can be converted by suitable sulfurization reagents, e.g. Lawesson's reagent or phosphorus (V) sulfide, to a thioamide function, whereby compounds according to the invention of the general structure (Ib) are formed (see e.g. WO 2004/018439).

Carboxylic acids of the general structure 2 can be obtained from carboxylic esters of the general structure 1 according to known literature methods, by means of hydrolysis by suitable bases, such as e.g. aqueous lithium hydroxide or sodium hydroxide solution, in suitable solvents or diluents such as e.g. dioxane or THF.

In reaction scheme 1a, a general preparation method for intermediates of the general structure 1c is shown.

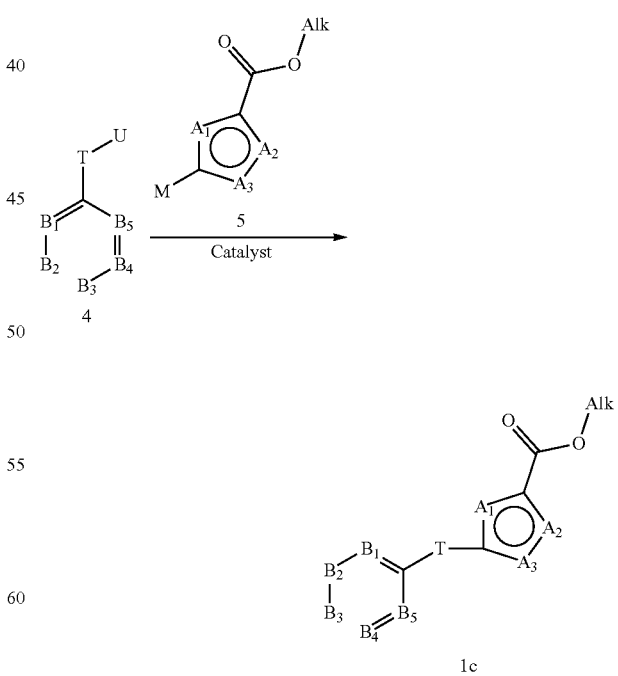

The radicals $A_1$, $A_2$, $A_3$, $B_1$, $B_2$, $B_3$, $B_4$, $B_5$, $R_1$, and $R_2$ have the definitions described above. T is $T_1$, $T_2$ or $T_3$. Alk is a $C_1$-$C_4$-alkyl. U is bromine or iodine, if M is a boronic acid, a boronic ester or a zinc halide. U is a boronic acid, a boronic ester or a zinc halide if M is bromine, iodine or triflate.

The compounds of the general structure 1c can be prepared by palladium catalyzed reactions from the reaction partners 4 and 5 (see e.g. WO 2011/149874; WO 2014/152115; WO 2010/093885; Organic & biomolecular chemistry (2016), 14, p. 2352). The compounds of the general structure 5 are either commercially available or can be prepared by methods known to those skilled in the art (see e.g. WO 2009/106441; WO 2012/038743; Angewandte Chemie, International Edition (2013), 52, p. 7818). The compounds of the general structure 4 can be prepared by known literature methods (see e.g. WO 2016/174052; Organic & biomolecular chemistry (2016), 14, p. 2352).

In reaction scheme 1b, a general preparation method for intermediates of the general structure 1d is shown.

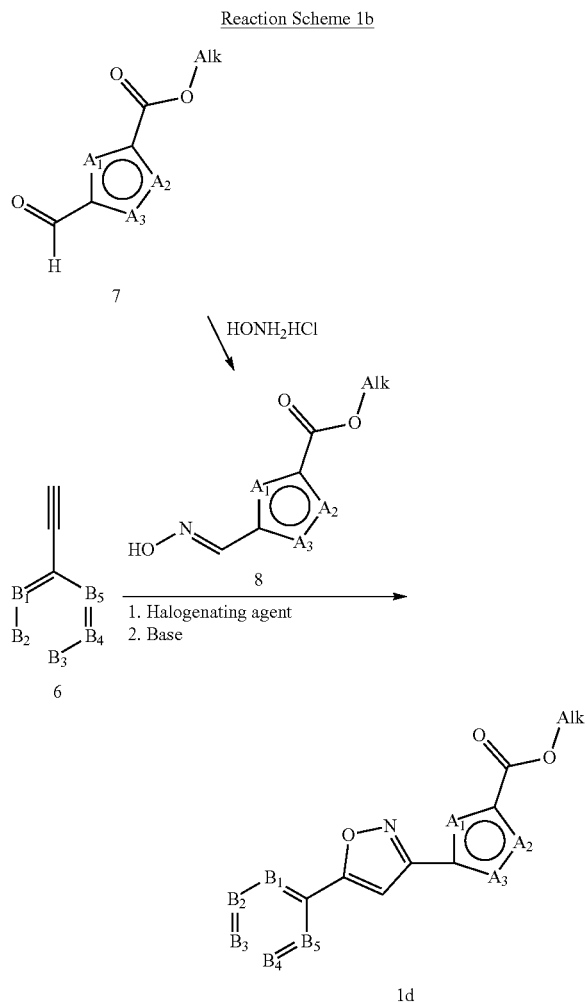

Reaction Scheme 1b

The radicals $A_1$, $A_2$, $A_3$, $B_1$, $B_2$, $B_3$, $B_4$ and $B_5$ have the definitions described above. Alk is a $C_1$-$C_4$-alkyl.

Intermediates of the general structure 1d can be obtained by analogy to known literature methods from intermediates of the general structure 8 and 6. Here, the oximes 8 are firstly reacted with suitable halogenating agents, e.g. N-halosuccinimides and then reacted with acetylenes of the general structure 6 in the presence of a suitable base, e.g. triethyl-amine (see e.g. European Journal of Medicinal Chemistry 2014, 82, 214-224; WO 2016/174052).

Oximes of the general structure 8 are known or can be prepared by analogy to known literature methods from aldehydes of the general structure 7 (e.g. Bioorganic & Medicinal Chemistry 2012, 20, 5763-5773; J. Chem. Soc. Perk. Trans. 1 1980, 4, 1029-1037). Aldehydes of the general structure 7 are commercially available or can be prepared by methods known to those skilled in the art. Alkynes of the general structure 6 are known or can be prepared by analogy to known literature methods (see e.g. WO 2016/174052).

In reaction scheme 1c, a general preparation method for intermediates of the general structure 1e is shown.

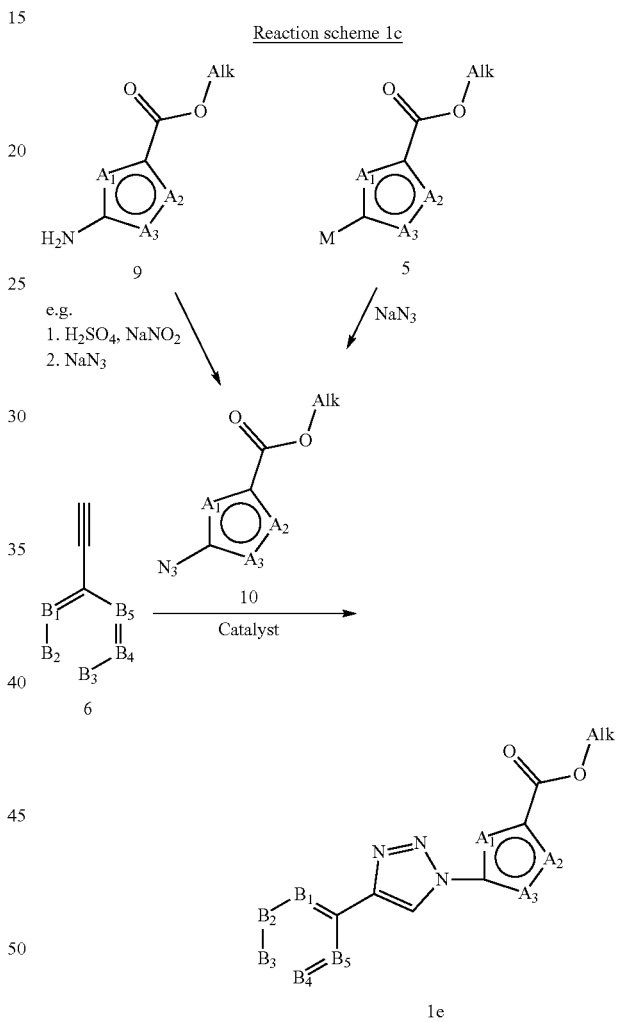

Reaction scheme 1c

The radicals $A_1$, $A_2$, $A_3$, $B_1$, $B_2$, $B_3$, $B_4$ and $B_5$ have the definitions described above. Alk is a $C_1$-$C_4$-alkyl. M is fluorine, chlorine, bromine or iodine.

Intermediates of the general structure 1e can be obtained by Cu-catalyzed (see e.g. WO 2008/074835) reaction of azides of the general structure 10 and acetylenes of the general structure 6.

Azides of the general structure 10 can be obtained by analogy to known literature methods starting from amines of the general structure 9 (e.g. Tetrahedron Lett. 2013, 54, 1294-1297; Tetrahedron 2009, 65, 2678-2683). Amines of the general structure 9 are commercially available or can be prepared by methods known to those skilled in the art.

Alternatively, azides of the general structure 10 can be obtained starting from halides of the general structure 5 (in which M is fluorine, chlorine, bromine or iodine) by nucleophilic substitution. The reaction with sodium azide proceeds either by thermal activation (see e.g. WO 2010/121675 or WO 2012/107434) or under Cu catalysis (see e.g. WO 2014/114532). The reactions under Cu catalysis can take place in the presence of alkynes of the general structure 6, such that the reaction to give the intermediates of the general structure 1c is carried out in a one-pot process (see e.g. Beilstein *J. Org. Chem.* 2012, 8, 683-692).

In reaction scheme 1d, a general preparation method for intermediates of the general structure 1f is shown.

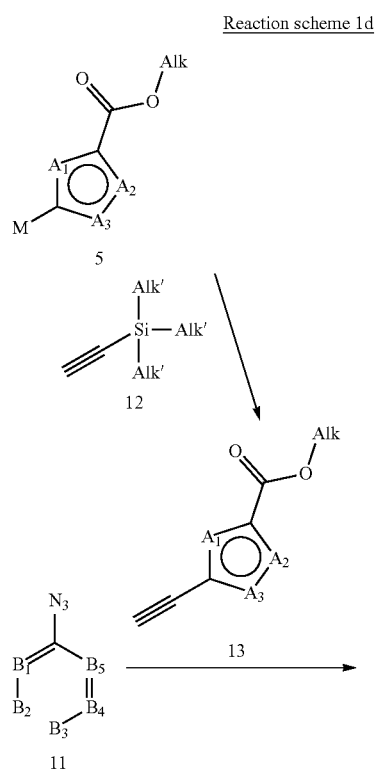

The radicals $A_1$, $A_2$, $A_3$, $B_1$, $B_2$, $B_3$, $B_4$ and $B_5$ have the definitions described above. Alk is a $C_1$-$C_4$-alkyl. Alk is an optionally substituted $C_1$-$C_6$-alkyl. M is bromine or iodine.

Intermediates of the general structure 1f can be obtained by Cu-catalyzed reaction of azides of the general structure 11 and acetylenes of the general structure 13 (see e.g. Journal of Combinatorial Chemistry 2009, 11, 947; Journal of Medicinal Chemistry 2012, 55, 5642).

Azides of the general structure 11 are known or can be prepared by analogy to known literature methods (see e.g. WO2016/008830). Alkynes of the general structure 13 are known or can be obtained in a two-stage sequence by transition metal-catalyzed reaction of halides of the general structure 5 with trialkylsilylacetylenes of the general structure 12 followed by cleavage of the silyl group (see e.g. WO 2016/055947).

In reaction scheme 1e, a preparation method for intermediates of the general structure 1g-1i is shown.

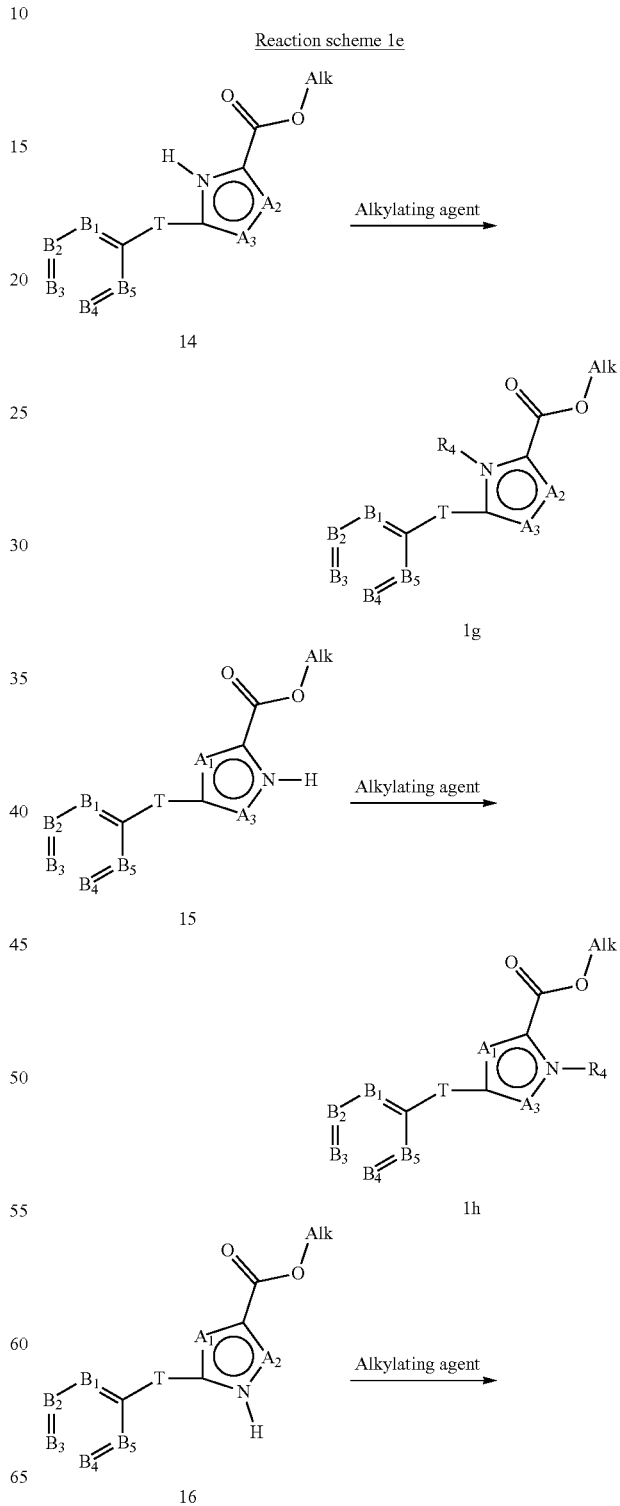

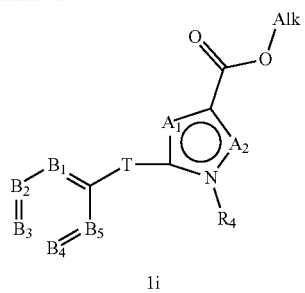

1i

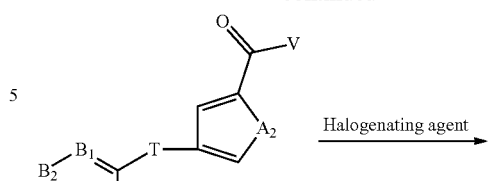

18

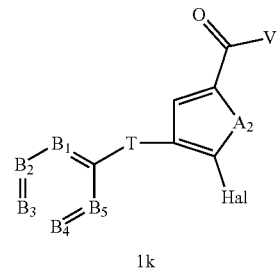

1k

The radicals $B_1$, $B_2$, $B_3$, $B_a$, $B_5$, $R_a$ and T have the definitions described above. Alk is a $C_1$-$C_4$-alkyl. The radicals $A_1$, $A_2$ and $A_3$ are N or $CR_3$.

Intermediates of the general structure 1g-1i can be obtained by deprotonation of intermediates of the general structure 14-16 by a suitable base and subsequent reaction with alkylating agents. The alkylating agents used are, for example, alkyl halides in combination with alkali metal hydrides or alkali metal carbonates as base (see e.g. WO 2015/011281 for the combination of methyl iodide and sodium hydride, WO 2012/038904 for the combination of potassium carbonate and ethyl bromide). The intermediates of the general structure 14-16 can be obtained by the preparation method shown in reaction schemes 1a-d. For this purpose, compounds of the general structure, inter alia, 5, 8 10 or 13 can be used, in which one of the substituents $A_1$, $A_2$ or $A_3$ is N-(tert-butoxycarbonyl), [see e.g. EP 2594555]. In order to obtain the compounds of the general structure 14-16, the (tert-butoxycarbonyl) group must be cleaved, optionally still under acidic conditions (siehe z.B. WO 2013/092512).

In reaction scheme 2, a preparation method for intermediates of the general structure 1j, 1k and compounds according to the invention which come under the general structure (Ia), is shown.

The radicals $B_1$, $B_2$, $B_3$, $B_4$, $B_5$ and T have the definitions described above. $A_3$ and $A_2$ are S, O or N—$R^4$. Hal is chlorine or bromine. V is $C_1$-$C_4$-alkoxy or $NR_1R_2$.

Compounds of the general structure 1j and 1k can be obtained by reacting intermediates of the general structure 17 or 18 respectively with halogenating agents. The halogenating agents used are, e.g. N-halosuccinimides (see e.g. WO 2009/112845, WO 2008/098105 for Hal=chlorine, WO 2012/137181, WO 2013/079223 for Hal=bromine). Compounds of the general structure 1j and 1k in which V is $C_1$-$C_4$-alkoxy can be converted according to reaction scheme 1 to compounds according to the invention which come under the general structure (I'a). If V is $NR_1R_2$, the compounds of the general structure 1j to 1k are compounds according to the invention of the structure (Ia).

Reaction scheme 2

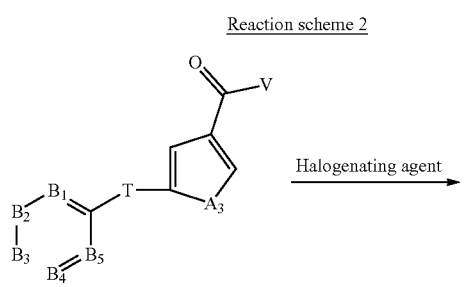

17

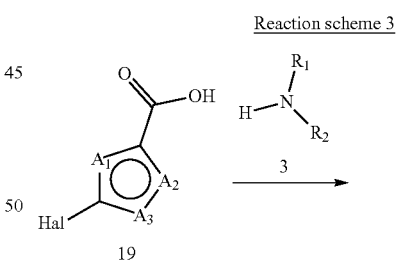

1j

Reaction scheme 3

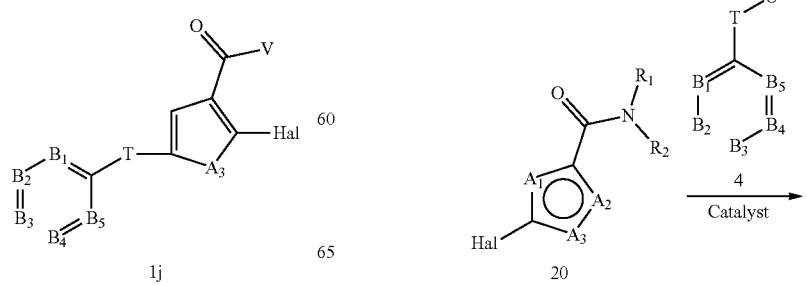

-continued

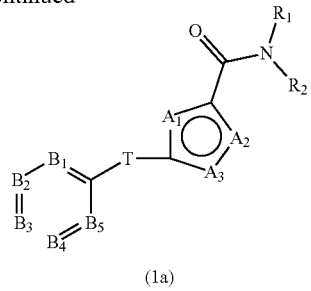

(Ia)

The radicals $A_1$, $A_2$, $A_3$, $B_1$, $B_2$, $B_3$, $B_4$, $B_5$, $R_1$, and $R_2$ have the definitions described above. T is $T_1$, $T_2$ or $T_3$. Hal is bromine or iodine. U is a boronic acid, a boronic ester or a zinc halide.

By activating carboxylic acids of the general structure 19 and subsequent reaction of the activated intermediate with amines of the general structure 3, amides of the general structure 20 can be obtained. For this amidation step, numerous reaction conditions have been described. A summary can be found in Houben-Weyl, Methoden der Organischen Chemie, Volume ES (Georg Thieme Verlag Stuttgart), p. 934. Some of these reactions proceed via intermediary carbonyl chlorides which can be isolated or generated in-situ. The amines of the general structure 3 or salts thereof are commercially available or can be prepared by methods known to those skilled in the art. The carboxylic acids of the general structure 19 are commercially available or can be prepared by methods known to those skilled in the art (see e.g. WO2012/033390 for the synthesis of 5-bromo-2-methylthiophene-3-carboxylic acid).

The compounds of the general structure (Ia) can be prepared by palladium-catalyzed reactions of the reaction partners 4 and 20 (see e.g. WO2009/112845 for U=boronic ester or boronic acid; Angewandte Chemie International Edition, 2013, 52, 615 for U=zinc halide).

Reaction scheme 4

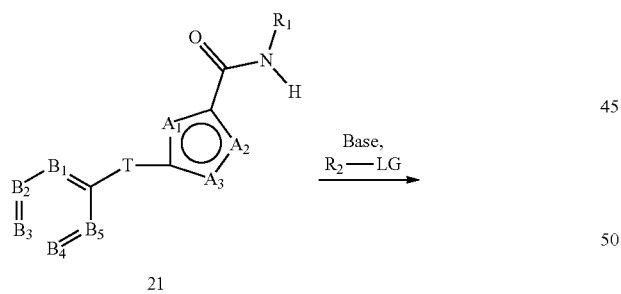

The radicals $A_1$, $A_2$, $A_3$, $B_1$, $B_2$, $B_3$, $B_4$, $B_5$, T and $R_1$ have the definitions described above. $R_2$ is $C_1$-$C_6$-alkyl. LG is a leaving group, e.g. iodine or bromine.

Compounds according to the invention of the general structure 21 can be converted, according to reaction scheme 4 by deprotonation with a suitable base such as e.g. sodium hydride, and reaction with a suitable electrophile such as e.g. methyl iodide, to compounds according to the invention of the general structure (Ia), in which $R_2$ is $C_1$-$C_6$-alkyl.

The following intermediate (A) for preparing compounds of the formula (I), in which $B_2$ and $B_4$ are in each case C—H, $B_1$ and $B_5$ are C—$C_1$ and $B_3$ is perfluorinated propyl, is already known from WO2017/025590:

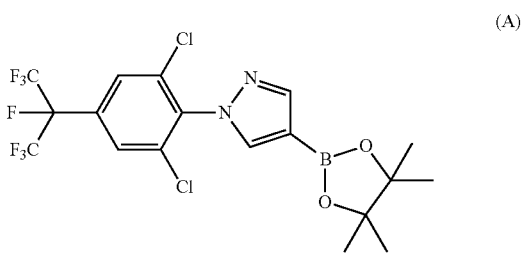 [SMILES: CC1(C)OB(c2cnn(-c3c(Cl)cc(C(F)(C(F)(F)F)C(F)(F)F)cc3Cl)c2)OC1(C)C]

Furthermore, the invention relates to the following intermediates of the formulae (B) and (C) which can be used to prepare compounds of the formula (I), in which Z is C, $A_1$ is CH, $A_2$ is C—$CH_3$, $A_3$ is S, Q is O, $R_2$ is H and $R_1$ is cycloalkyl or 1-cyanocyclopropyl.

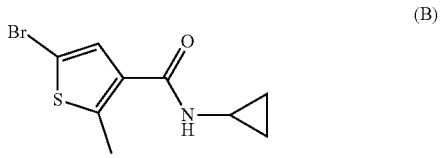

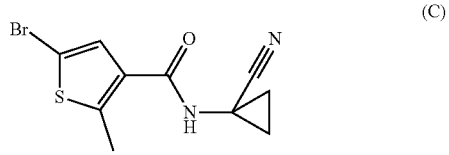

EXPERIMENTAL SECTION

Preparation of 1-[2,6-dichloro-4-(1,1,1,2,3,3,3-heptafluoropropan-2-yl)phenyl]-4-(4,4,5,5-tetramethyl-1,3,2-dioxaborolan-2-yl)-1H-pyrazole

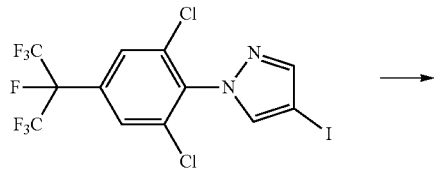

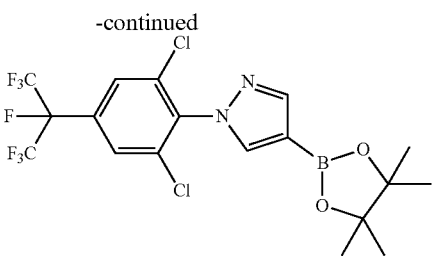

To a solution of 1.27 g (2.50 mmol) of 1-[2,6-dichloro-4-(1,1,1,2,3,3,3-heptafluoropropan-2-yl)phenyl]-4-iodo-1H-pyrazole in THF were added dropwise at −39° C. 2.12 mL of a 1.3 wt solution of isopropylmagnesium chloride lithium chloride complex and the reaction solution was then stirred at −38° C. for 30 minutes. 0.59 mL (2.9 mmol) of 2-isopropoxy-4,4,5,5-tetramethyl-1,3,2-dioxaborolane were then added dropwise, the cooling bath removed and the reaction solution was stirred at room temperature for 1 h. Saturated ammonium chloride solution was added and the mixture extracted repeatedly with cyclohexane. The combined organic phases were washed with saturated sodium hydrogencarbonate solution and saturated sodium chloride solution, dried with sodium sulfate, filtered and the solvent removed under reduced pressure. The residue was purified chromatographically by MPLC on silica gel (gradient: ethyl acetate/cyclohexane 0:100→30:70). This gave 270 mg of 1-[2,6-dichloro-4-(1,1,1,2,3,3,3-heptafluoropropan-2-yl)phenyl]-4-(4,4,5,5-tetramethyl-1,3,2-dioxaborolan-2-yl)-1H-pyrazole.

$^1$H-NMR (400.0 MHz, $d_6$-DMSO):
δ=8.3610 (1.8); 8.0447 (2.5); 7.9563 (1.8); 3.3155 (30.9); 2.5234 (1.0); 2.5099 (19.5); 2.5057 (38.9); 2.5012 (51.1); 2.4967 (37.6); 2.4925 (18.8); 1.3981 (3.0); 1.2932 (16.0); −0.0002 (1.8)

Preparation of N-(1-cyanocyclopropyl)-2-{1-[2,6-dichloro-4-(1,1,1,2,3,3,3-heptafluoropropan-2-yl)phenyl]-1H-pyrazol-4-yl}-1,3-thiazole-4-carboxamide

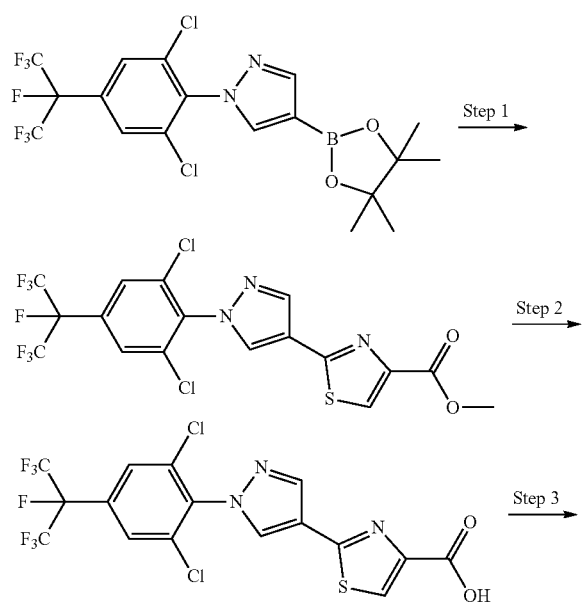

Stage 1: Methyl 2-{1-[2,6-dichloro-4-(1,1,1,2,3,3,3-heptafluoropropan-2-yl)phenyl]-1H-pyrazol-4-yl}-1,3-thiazole-4-carboxylate

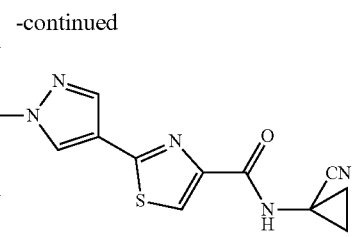

A mixture of 1.0 g (1.8 mmol) of 1-[2,6-dichloro-4-(1,1,1,2,3,3,3-heptafluoropropan-2-yl)phenyl]-4-(4,4,5,5-tetramethyl-1,3,2-dioxaborolan-2-yl)-1H-pyrazole, 400 mg (1.8 mmol) of methyl 2-bromo-1,3-thiazole-4-carboxylate, 416 mg (360 μmol) of tetrakis(triphenylphosphine)palladium, 1.7 g (5.2 mmol) of cesium carbonate, 8 mL of 1,4-dioxane and 0.8 mL of water was heated at 100° C. in a microwave reactor for 2 h. 100 mL of ethyl acetate were added to the reaction mixture, which was washed with a saturated aqueous sodium chloride solution and the organic phase was then dried with sodium sulfate. The drying agent was filtered off and the solvent was removed under reduced pressure. The residue was separated chromatographically by preparative thin-layer chromatography (gradient: ethyl acetate/petroleum ether). This gave 400 mg of methyl 2-{1-[2,6-dichloro-4-(1,1,1,2,3,3,3-heptafluoropropan-2-yl)phenyl]-1H-pyrazol-4-yl}-1,3-thiazole-4-carboxylate.

$^1$H-NMR (300.1 MHz, $d_6$-DMSO):
δ=8.9335 (5.3); 8.5257 (7.3); 8.4429 (5.3); 8.1134 (8.1); 6.5446 (0.3); 3.8618 (16.0); 3.3211 (54.8); 2.7275 (0.4); 2.5074 (54.8); 2.5017 (71.9); 2.4960 (51.6); 2.2712 (0.5); 0.0109 (0.4); −0.0001 (10.4); −0.0111 (0.4)

Stage 2: 2-{1-[2,6-dichloro-4-(1,1,1,2,3,3,3-heptafluoropropan-2-yl)phenyl]-1H-pyrazol-4-yl}-1,3-thiazole-4-carboxylic acid A mixture of 420 mg (804 μmol) of methyl 2-{1-[2,6-dichloro-4-(1,1,1,2,3,3,3-heptafluoropropan-2-yl)phenyl]-1H-pyrazol-4-yl}-1,3-thiazole-4-carboxylate and 336 mg (800 μmol) of lithium hydroxide monohydrate, 2 mL of water and 5 mL of methanol was stirred at room temperature for 4 h. The solution was then adjusted to a pH of 5-6 by adding concentrated hydrochloric acid and the mixture was extracted with dichloromethane. The combined organic phases were washed with saturated aqueous sodium chloride solution, dried with sodium sulfate and filtered. The solvent was removed under reduced pressure. This gave 510 mg of a mixture of 2-{1-[2,6-dichloro-4-(1,1,1,2,3,3,3-heptafluoropropan-2-yl)phenyl]-1H pyrazol-4-yl}-1,3-thiazole-4-carboxylic acid with unknown impurities.

$^1$H-NMR (400.2 MHz, $d_6$-DMSO):
δ=8.7673 (5.0); 8.3477 (4.3); 8.1073 (16.0); 7.6718 (3.4); 4.0228 (0.6); 4.0064 (0.5); 3.8629 (0.5); 3.3328 (173.3); 3.3101 (5.0); 2.8922 (0.4); 2.7327 (0.3); 2.6725 (1.3); 2.5036 (214.5); 2.3304 (1.3); 2.0878 (0.3); 1.2356 (2.2); 1.1482 (1.3); 0.9410 (1.4); 0.9241 (1.4); 0.8548 (0.4); 0.0016 (71.0); −0.1479 (0.4)

Stage 3: N-(1-cyanocyclopropyl)-2-{1-[2,6-dichloro-4-(1,1,1,2,3,3,3-heptafluoropropan-2-yl)phenyl]-1H-pyrazol-4-yl}-1,3-thiazole-4-carboxamide To a solution of 100 mg of the residue from stage 2 in 4 mL N,N-dimethylformamide were added 35 mg (0.30 mmol) of 1-aminocyclopropanecarbonitrile hydrochloride, 114 mg (300 µmol) of N,N,N,N-tetramethyl-O-(7-azabenzotriazol-1-yl)uronium hexafluorophosphate (HATU) and 52 mg (0.40 mmol) of diisopropylethylamine. The reaction mixture was stirred at room temperature for 6 h. A saturated aqueous sodium chloride solution was then added and the mixture extracted with ethyl acetate. The combined organic phases were washed with saturated aqueous sodium chloride solution, dried with sodium sulfate and filtered. The solvent was removed under reduced pressure. The residue was separated chromatographically by HPLC. This gave 19 mg of N-(1-cyanocyclopropyl)-2-{1-[2,6-dichloro-4-(1,1,1,2,3,3,3-heptafluoropropan-2-yl)phenyl]-1H-pyrazol-4-yl}-1,3-thiazole-4-carboxamide.

$^1$H-NMR (300.1 MHz, $d_6$-DMSO):

δ=9.3332 (5.8); 8.9075 (0.7); 8.8701 (10.7); 8.4267 (10.4); 8.3503 (14.4); 8.1109 (16.0); 6.5159 (3.8); 5.7424 (1.3); 3.6057 (0.6); 3.3890 (0.8); 3.3134 (232.3); 3.2896 (8.2); 2.7270 (5.2); 2.7211 (3.8); 2.6517 (0.7); 2.5849 (1.2); 2.5065 (611.3); 2.5007 (800.6); 2.4951 (565.5); 2.2766 (3.7); 2.2704 (4.6); 2.1633 (1.0); 2.0899 (1.2); 2.0495 (0.7); 1.5985 (2.2); 1.5789 (5.3); 1.5703 (5.8); 1.5529 (2.6); 1.3563 (3.0); 1.3396 (5.6); 1.3301 (5.4); 1.3117 (2.0); 1.2342 (0.9); 0.8563 (0.6); 0.1949 (2.2); 0.0108 (22.0); −0.0001 (542.6); −0.0111 (19.3); −0.1987 (2.2); −2.2299 (0.6); 3.3736 (0.6); −3.5153 (0.7)

Preparation of methyl 4-{1-[2,6-dichloro-4-(1,1,1,2,3,3,3-heptafluoropropan-2-yl)phenyl]-1H-pyrazol-4-yl}-1-methyl-1H-pyrrole-2-carboxylate

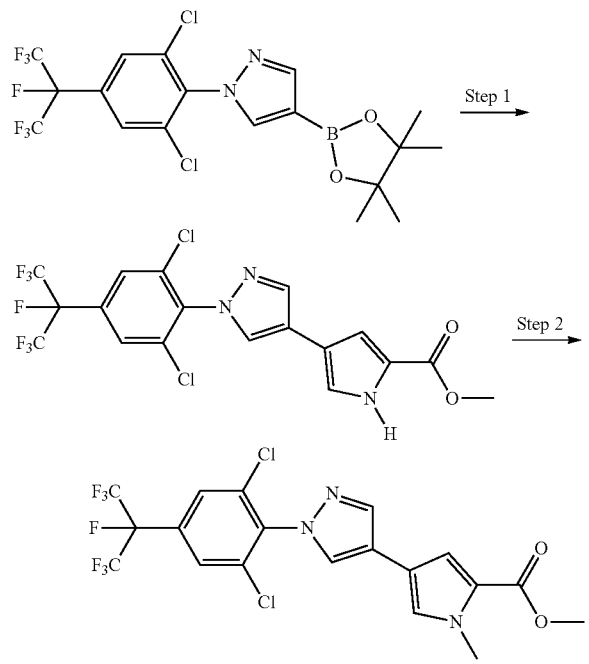

Stage 1: Methyl 4-{1-[2,6-dichloro-4-(1,1,1,2,3,3,3-heptafluoropropan-2-yl)phenyl]-1H-pyrazol-4-yl}-1H-pyrrole-2-carboxylate A mixture of 1.7 g (3.4 mmol) of 1-[2,6-dichloro-4-(1,1,1,2,3,3,3-heptafluoropropan-2-yl)phenyl]-4-(4,4,5,5-tetramethyl-1,3,2-dioxaborolan-2-yl)-1H-pyrazole, 3.0 g (9.9 mmol) of 1-tert-butyl 2-methyl 4-bromo-1H-pyrrole-1,2-dicarboxylate, 763 mg (660 µmol) of tetrakis(triphenylphosphine)palladium, 3.2 g (9.8 mmol) of cesium carbonate, 20 mL of 1,4-dioxane and 2 mL of water was heated at 100° C. in a microwave reactor for 2 h. 100 mL of ethyl acetate were added to the reaction mixture which was washed with a saturated aqueous sodium chloride solution and the organic phase was then dried with sodium sulfate. The drying agent was filtered off and the solvent was removed under reduced pressure. The residue was separated chromatographically by preparative thin-layer chromatography (gradient: ethyl acetate/petroleum ether). This gave 600 mg of methyl 4-{1-[2,6-dichloro-4-(1,1,1,2,3,3,3-heptafluoropropan-2-yl)phenyl]-1H-pyrazol-4-yl}-1H-pyrrole-2-carboxylate.

$^1$H-NMR (300.1 MHz, $d_6$-DMSO):

δ=11.9847 (1.1); 8.3084 (5.9); 8.1316 (5.9); 8.0531 (8.7); 7.3581 (1.8); 7.3527 (2.2); 7.3489 (2.2); 7.3435 (1.8); 7 0.0571 (2.0); 7.0512 (2.8); 7.0442 (1.8); 6.5190 (0.4); 3.7806 (16.0); 3.3136 (68.4); 2.7268 (0.5); 2.5066 (60.6); 2.5 010 (77.6); 2.4954 (55.0); 2.2764 (0.4); 2.2711 (0.5); 1.2355 (1.5); 1.0688 (0.8); 0.0105 (0.5); −0.0001 (10.3)

Stage 2: Methyl 4-{1-[2,6-dichloro-4-(1,1,1,2,3,3,3-heptafluoropropan-2-yl)phenyl]-1H-pyrazol-4-yl}-1-methyl-1H-pyrrole-2-carboxylate To a solution of 600 mg (1.19 mmol) of methyl 4-{1-[2,6-dichloro-4-(1,1,1,2,3,3,3-heptafluoropropan-2-yl)phenyl]-1H-pyrazol-4-yl}-1H-pyrrole-2-carboxylate in 5 mL of N,N-dimethylformamide at 0° C. were added 58 mg (2.4 mmol) of sodium hydride and the mixture was stirred at this temperature for 15 minutes. 255 mg (1.80 mmol) of methyl iodide were then added. The reaction mixture was stirred at room temperature for 6 h, ice-water was added and the mixture was extracted repeatedly with ethyl acetate. The combined organic phases were washed with a saturated aqueous sodium chloride solution, dried with sodium sulfate, filtered and the solvent was removed under reduced pressure. The residue was separated chromatographically by preparative thin-layer chromatography (gradient: ethyl acetate/petroleum ether). This gave 400 mg of methyl 4-{1-[2,6-dichloro-4-(1,1,1,2,3,3,3-heptafluoropropan-2-yl)phenyl]-1H-pyrazol-4-yl}-1-methyl-1H-pyrrole-2-carboxylate.

$^1$H-NMR (300.1 MHz, $d_6$-DMSO):

δ=8.2975 (5.4); 8.0894 (5.4); 8.0585 (8.0); 7.4203 (2.8); 7.4140 (2.9); 7.1076 (3.6); 7.1010 (3.5); 4.1281 (0.4); 4.1107 (1.1); 4.0932 (1.1); 4.0759 (0.4); 3.8832 (14.4); 3.7625 (16.0); 3.7393 (0.4); 3.3300 (7.6); 3.1773 (4.9); 3.1599 (5.3); 2.5143 (7.4); 2.5086 (14.6); 2.5028 (19.3); 2.4970 (13.6); −0.0001 (4.1)

Preparation of ethyl 2-bromo-5-{1-[2,6-dichloro-4-(1,1,1,2,3,3,3-heptafluoropropan-2-yl)phenyl]-1H-pyrazol-4-yl)thiophene-3-carboxylate

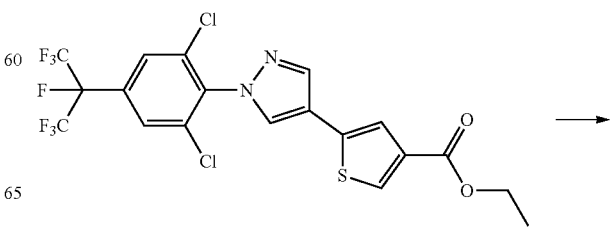

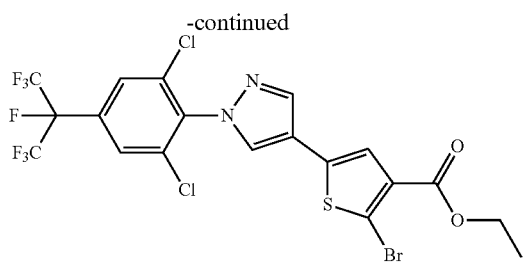

To a solution of 500 mg (959 μmol) of ethyl 5-{1-[2,6-dichloro-4-(1,1,1,2,3,3,3-heptafluoropropan-2-yl)phenyl]-1H-pyrazol-4-yl}thiophene-3-carboxylate in 3 mL of acetic acid were added 130 mg (730 μmol) of N-bromosuccinimide. The reaction mixture was stirred at room temperature for 30 min, a saturated aqueous saline solution was added and the mixture extracted repeatedly with ethyl acetate. The combined organic phases were washed with a saturated aqueous sodium chloride solution, dried with sodium sulfate, filtered and the solvent removed under reduced pressure. The residue was separated chromatographically by column chromatography on silica gel (gradient: ethyl acetate/petroleum ether). This gave 390 mg of ethyl 2-bromo-5-{1-[2,6-dichloro-4-(1,1,1,2,3,3,3-heptafluoropropan-2-yl)phenyl]-1H-pyrazol-4-yl}thiophene-3-carboxylate.

$^1$H-NMR (300.1 MHz, $d_6$-DMSO):
δ=8.6631 (8.8); 8.6452 (0.5); 8.3343 (8.9); 8.0962 (13.3); 7.5786 (11.6); 6.5358 (1.0); 4.3404 (2.1); 4.3168 (6.8); 4.2932 (7.0); 4.2696 (2.2); 3.3266 (121.6); 2.7345 (0.6); 2.7279 (0.7); 2.5079 (93.7); 2.5021 (122.5); 2.4964 (85.7); 2.2708 (0.7); 1.3710 (0.4); 1.3510 (7.6); 1.3274 (16.0); 1.3037 (7.2); 1.2356 (0.6); 0.0109 (0.8); −0.0001 (20.1)

Preparation of 5-chloro-N-cyclopropyl-4-{1-[2,6-dichloro-4-(1,1,1,2,3,3,3-heptafluoropropan-2-yl)phenyl]-1H-pyrazol-4-yl}-1-methyl-1H-pyrrole-2-carboxamide

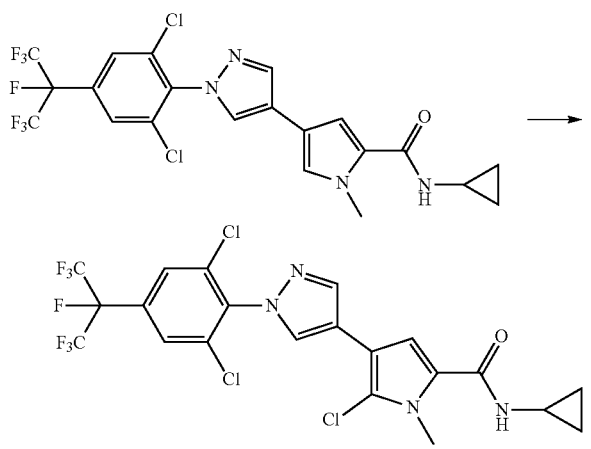

To a solution of 45 mg (83 μmol) of N-cyclopropyl-4-{1-[2,6-dichloro-4-(1,1,1,2,3,3,3-heptafluoropropan-2-yl)phenyl]-1H-pyrazol-4-yl}-1-methyl-1H-pyrrole-2-carboxamide in 0.3 mL of acetic acid at 0° C. were added 10 mg (75 μmol) of N-chlorosuccinimide. The reaction mixture was stirred at room temperature for 30 minutes, a saturated aqueous sodium thiosulfate solution was added and the mixture stirred again at room temperature for 30 minutes. Saturated aqueous saline solution was then added and the mixture extracted repeatedly with ethyl acetate. The combined organic phases were washed with a saturated aqueous sodium chloride solution, dried with sodium sulfate, filtered and the solvent removed under reduced pressure. The residue was separated chromatographically by HPLC. This gave 13 mg of 5-chloro-N-cyclopropyl-4-{1-[2,6-dichloro-4-(1,1,1,2,3,3,3-heptafluoropropan-2-yl)phenyl]-1H-pyrazol-4-yl}-1-methyl-1H-pyrrole-2-carboxamide.

$^1$H-NMR (400.0 MHz, $d_6$-DMSO):
δ=8.3976 (5.6); 8.1968 (1.5); 8.1869 (1.5); 8.0746 (5.5); 8.0489 (8.4); 7.0532 (5.8); 3.8637 (16.0); 3.3216 (75.3); 2.9610 (0.3); 2.7964 (0.5); 2.7869 (0.8); 2.7783 (1.1); 2.7685 (1.2); 2.7600 (0.8); 2.7505 (0.5); 2.6749 (0.5); 2.6706 (0.7); 2.6663 (0.5); 2.5061 (88.6); 2.5017 (116.5); 2.4973 (85.5); 2.3284 (0.7); 2.3237 (0.5); 2.0742 (6.1); 0.700 6 (0.7); 0.6877 (1.9); 0.6826 (2.7); 0.6706 (2.5); 0.6645 (2.2); 0.6534 (0.9); 0.5535 (0.9); 0.5430 (2.8); 0.5369 (2.5); 0.5275 (2.2); 0.5152 (0.7); 0.0079 (0.7); −0.0002 (18.7)

Preparation of 2-chloro-N-cyclopropyl-5-{1-[2,6-dichloro-4-(1,1,1,2,3,3,3-heptafluoropropan-2-yl)phenyl]-1H-pyrazol-4-yl}thiophene-3-carboxamide

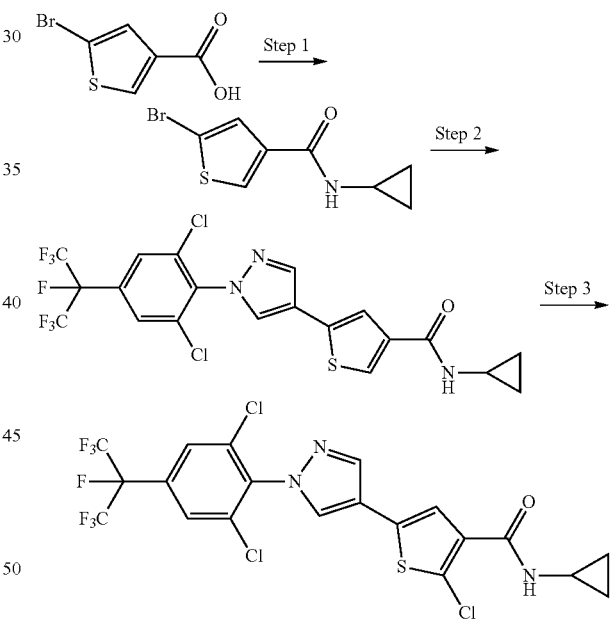

Stage 1:
5-Bromo-N-cyclopropylthiophene-3-carboxamide

To a solution of 1.00 g (4.83 mmol) of 5-bromothiophene-3-carboxylic acid in 20 mL of $CH_2Cl_2$ were added one drop of N,N-dimethylformamide and 1.0 mL (11 mmol) of oxalyl dichloride. The solution was heated under reflux for 3 h and 1.0 mL (11 mmol) of oxalyl dichloride was again added thereto and the mixture heated under reflux for a further 1.5 h. The solvent was then removed under reduced pressure.

The residue was dissolved in 20 mL of $CH_2Cl_2$ at 0° C., 0.75 mL (5.4 mmol) of triethylamine and 0.37 mL (5.3 mmol) of cyclopropylamine were added and the mixture then stirred overnight at room temperature. The reaction solution was diluted with $CH_2Cl_2$ and washed repeatedly with water. The organic phase was dried with sodium sulfate, filtered and the solvent removed under reduced pressure. The residue was separated chromatographically by MPLC on RP silica gel (gradient: $H_2O$/acetonitrile). This gave 1.06 g of 5-bromo-N-cyclopropylthiophene-3-carboxamide.

$^1$H-NMR (400.0 MHz, $d_6$-DMSO):

δ=8.2864 (4.0); 8.2781 (4.0); 8.0736 (15.3); 8.0696 (15.5); 7.5558 (16.0); 7.5517 (15.8); 3.3238 (22.1); 2.8055 (0.8); 2.7956 (2.4); 2.7861 (3.3); 2.7774 (5.4); 2.7676 (5.4); 2.7590 (3.4); 2.7495 (2.5); 2.7395 (0.9); 2.6718 (0.4); 2.5250 (1.0); 2.5116 (27.4); 2.5072 (55.9); 2.5028 (73.5); 2.4983 (52.4); 2.4940 (25.1); 2.3339 (0.3); 2.3294 (0.4); 2.0756 (0.7); 0.7038 (3.0); 0.6915 (8.8); 0.6859 (11.8); 0.6739 (11.6); 0.6679 (8.9); 0.6566 (4.3); 0.6354 (0.6); 0.6174 (0.6); 0.5848 (0.6); 0.5747 (0.6); 0.5452 (4.2); 0.5347 (11.7); 0.5280 (10.3); 0.5245 (9.5); 0.5185 (9.2); 0.5065 (2.9); −0.0002 (3.2)

Stage 2: N-Cyclopropyl-5-{1-[2,6-dichloro-4-(1,1,1,2,3,3,3-heptafluoropropan-2-yl)phenyl]-1H-pyrazol-4-yl}thiophene-3-carboxamide A mixture of 380 mg (749 μmol) of 1-[2,6-dichloro-4-(1,1,1,2,3,3,3-heptafluoropropan-2-yl)phenyl]-4-(4,4,5,5-tetramethyl-1,3,2-dioxaborolan-2-yl)-1H-pyrazole, 185 mg (752 μmol) of 5-bromo-N-cyclopropylthiophene-3-carboxamide, 173 mg (150 μmol) of tetrakis(triphenylphosphine)palladium, 735 mg (2.25 mmol) of cesium carbonate, 4 mL of 1,4-dioxane and 0.4 mL of water was heated at 100° C. in a microwave reactor for 2 h. The solvent was then removed under vacuum. Water was added to the residue and the mixture extracted with ethyl acetate. The combined organic phases were dried with sodium sulfate, filtered and the solvent removed under reduced pressure. The residue was separated chromatographically by MPLC on silica gel (gradient: ethyl acetate/cyclohexane). This gave 262 mg of N-cyclopropyl-5-{1-[2,6-dichloro-4-(1,1,1,2,3,3,3-heptafluoropropan-2-yl)phenyl]-1H-pyrazol-4-yl}thiophene-3-carboxamide.

$^1$H-NMR (400.0 MHz, $d_6$-DMSO):

δ=8.5643 (10.2); 8.3084 (3.2); 8.2986 (3.3); 8.2151 (10.4); 8.0821 (16.0); 7.9803 (7.3); 7.6416 (7.2); 3.9294 (0.8); 3.3239 (34.4); 2.8354 (0.3); 2.8251 (1.0); 2.8159 (1.5); 2.8070 (2.2); 2.7975 (2.2); 2.7888 (1.5); 2.7794 (1.0); 2.7690 (0.4); 2.6719 (0.5); 2.5066 (70.2); 2.5027 (90.6); 2.4990 (68.6); 2.3299 (0.5); 1.0695 (4.9); 0.7210 (1.2); 0.7080 (3.8); 0.7032 (5.2); 0.6910 (4.8); 0.6853 (4.2); 0.6742 (1.7); 0.5698 (1.7); 0.5593 (5.3); 0.5528 (5.1); 0.5438 (4.4); 0.5313 (1.2); 0.0000 (9.6)

Stage 3: 2-Chloro-N-cyclopropyl-5-{1-[2,6-dichloro-4-(1,1,1,2,3,3,3-heptafluoropropan-2-yl)phenyl]-1H-pyrazol-4-yl}thiophene-3-carboxamide To a solution of 50 mg (86 μmol) of N-cyclopropyl-5-{1-[2,6-dichloro-4-(1,1,1,2,3,3,3-heptafluoropropan-2-yl)phenyl]-1H-pyrazol-4-yl}thiophene-3-carboxamide in 2 mL of acetic acid was added at 10° C. a solution of 13 mg (97 μmol) of N-chlorosuccinimide in 1 mL of acetic acid over 30 minutes. The reaction mixture was stirred at 60° C. for 18 h, a saturated aqueous sodium thiosulfate solution was added and the mixture stirred again at room temperature for 30 minutes. Saturated aqueous saline solution was then added and the mixture extracted repeatedly with ethyl acetate. The combined organic phases were dried with sodium sulfate, filtered and the solvent removed under reduced pressure. The residue was separated chromatographically by HPLC (gradient: $H_2O$/acetonitrile). This gave 31 mg of 2-chloro-N-cyclopropyl-5-{1-[2,6-dichloro-4-(1,1,1,2,3,3,3-heptafluoropropan-2-yl)phenyl]-1H-pyrazol-4-yl}thiophene-3-carboxamide.

$^1$H-NMR (400.0 MHz, $d_6$-DMSO):

δ=9.1968 (0.4); 8.7769 (1.0); 8.7466 (0.4); 8.5761 (9.3); 8.5621 (0.6); 8.3702 (2.5); 8.3595 (2.6); 8.2724 (1.1); 8.2292 (9.3); 8.2007 (0.6); 8.0858 (16.0); 7.8646 (0.6); 7.4156 (10.1); 7.3687 (0.6); 5.7567 (12.1); 3.3217 (86.6); 2.8437 (0.4); 2.8330 (1.0); 2.8241 (1.4); 2.8148 (2.0); 2.8052 (2.0); 2.7964 (1.3); 2.7863 (0.9); 2.7770 (0.4); 2.6712 (0.9); 2.5062 (129.2); 2.5020 (170.7); 2.4979 (125.2); 2.3284 (0.9); 2.0744 (2.6); 1.5860 (0.4); 1.5797 (0.4); 1.2624 (0.4); 1.2569 (0.4); 0.7379 (0.5); 0.7270 (1.4); 0.7146 (3.3); 0.7093 (4.5); 0.6971 (4.3); 0.6913 (3.6); 0.6802 (1.5); 0.5629 (1.5); 0.5522 (4.5); 0.5455 (4.3); 0.5363 (3.9); 0.5240 (1.4); 0.5069 (0.5); 0.1463 (0.3); 0.0077 (2.5); −0.0002 (68.7); −0.1495 (0.3)

Preparation of 2-chloro-N-(1-cyanocyclopropyl)-5-{1-[2,6-dichloro-4-(1,1,1,2,3,3,3-heptafluoropropan-2-yl)phenyl]-1H-pyrazol-4-yl}-N-methylthiophene-3-carboxamide

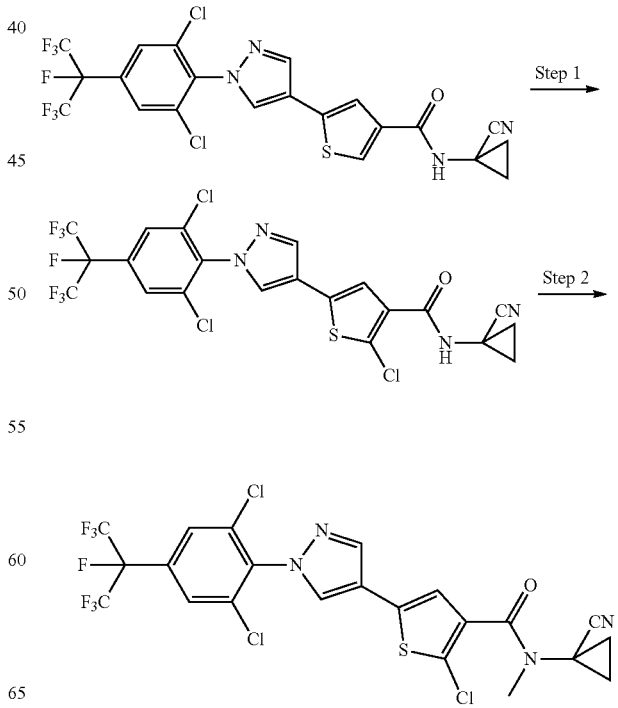

Stage 1: 2-Chloro-N-(1-cyanocyclopropyl)-5-{1-[2,6-dichloro-4-(1,1,1,2,3,3,3-heptafluoropropan-2-yl)phenyl]-1H-pyrazol-4-yl}thiophene-3-carboxamide To a solution of 70 mg (0.12 mmol) of N-(1-cyanocyclopropyl)-5-{1-[2,6-dichloro-4-(1,1,1,2,3,3,3-heptafluoropropan-2-yl)phenyl]-1H-pyrazol-4-yl}thiophene-3-carboxamide in 1 mL of chloroform were added 32 mg (0.14 mmol) of 2-chloro-1,3-bis(methoxycarbonyl)guanidine and the mixture was stirred overnight at room temperature. The solvent was then removed under reduced pressure and the residue separated chromatographically by HPLC (gradient: $H_2O$/acetonitrile). This gave 60 mg of 2-chloro-N-(1-cyanocyclopropyl)-5-{1-[2,6-dichloro-4-(1,1,1,2,3,3,3-heptafluoropropan-2-yl)phenyl]-1H-pyrazol-4-yl}thiophene-3-carboxamide. $^1$H-NMR (400.0 MHz, $d_6$-DMSO):

δ=9.6859 (1.5); 9.2607 (5.2); 8.8019 (2.3); 8.5964 (8.8); 8.2949 (2.4); 8.2366 (8.9); 8.0890 (16.0); 7.4870 (10.3); 3.3210 (33.2); 2.6752 (0.5); 2.6709 (0.7); 2.6665 (0.5); 2.5240 (1.7); 2.5104 (42.9); 2.5062 (89.1); 2.5018 (119.6); 2.4974 (86.3); 2.4932 (41.6); 2.3289 (0.6); 2.3237 (0.5); 1.6520 (0.5); 1.6379 (1.3); 1.6310 (1.3); 1.6175 (0.6); 1.5987 (1.9); 1.5843 (4.8); 1.5774 (5.1); 1.5644 (2.2); 1.2817 (2.2); 1.2682 (4.8); 1.2615 (5.2); 1.2469 (2.4); 1.2329 (1.4); 1.2262 (1.4); 1.2118 (0.5); 0.9264 (0.3); 0.9097 (0.3); 0.0077 (1.6); −0.0004 (42.8); −0.0086 (1.6)

Stage 2: 2-Chloro-N-(1-cyanocyclopropyl)-5-{1-[2,6-dichloro-4-(1,1,1,2,3,3,3-heptafluoropropan-2-yl)phenyl]-1H-pyrazol-4-yl}-N-methylthiophene-3-carboxamide To a solution of 50 mg (83 μmol) of 2-chloro-N-(1-cyanocyclopropyl)-5-{1-[2,6-dichloro-4-(1,1,1,2,3,3,3-heptafluoropropan-2-yl)phenyl]-1H-pyrazol-4-yl}thiophene-3-carboxamide in tetrahydrofuran was added at 0° C. 5 mg (0.1 mmol) of sodium hydride (55% dispersion in mineral oil). The suspension was stirred at 0° C. for 10 minutes, then 7 μL (0.1 mmol) of methyl iodide were added and the mixture was stirred overnight at room temperature. The reaction solution was diluted with $CH_2Cl_2$ and washed with water. The organic phase was dried with sodium sulfate, filtered and the solvent was removed under reduced pressure. The residue was separated chromatographically by HPLC (gradient: $H_2O$/acetonitrile). This gave 25 mg of 2-chloro-N-(1-cyanocyclopropyl)-5-{1-[2,6-dichloro-4-(1,1,1,2,3,3,3-heptafluoropropan-2-yl)phenyl]-1H-pyrazol-4-yl}-N-methylthiophene-3-carboxamide.

$^1$H-NMR (400.0 MHz, $d_6$-DMSO):

δ=8.8156 (1.0); 8.6100 (9.3); 8.3161 (1.2); 8.2652 (8.4); 8.0870 (16.0); 7.3933 (12.2); 5.7553 (1.7); 3.3194 (128.0); 3.0327 (13.4); 2.9944 (2.9); 2.6749 (1.2); 2.6706 (1.8); 2.6665 (1.3); 2.5240 (4.5); 2.5104 (109.0); 2.5061 (227.3); 2.5017 (304.5); 2.4973 (220.5); 2.4934 (108.7); 2.3327 (1.3); 2.3285 (1.7); 2.3244 (1.3); 2.0739 (0.4); 2.0084 (0.4); 1.9891 (0.4); 1.7318 (0.4); 1.7190 (0.5); 1.7076 (0.4); 1.6376 (2.3); 1.4846 (0.4); 1.4441 (2.3); 1.4305 (4.3); 1.4245 (4.4); 1.4085 (1.4); 1.2354 (3.1); 0.8542 (0.7); 0.1463 (0.8); 0.0079 (5.5); −0.0001 (165.6); −0.0084 (7.0); −0.1495 (0.8)

TABLE I-T1

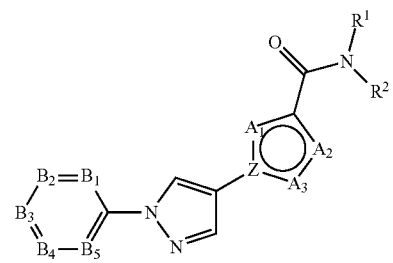

| Ex. No. | $B_1$ | $B_3$ | $B_5$ | $R_1$ | $R_2$ | Z | $A_1$ | $A_2$ | $A_3$ | Q |
|---|---|---|---|---|---|---|---|---|---|---|
| I-T1-1 | C—Cl | C-i-$C_3F_7$ | C—Cl | cyclopropyl | H | C | C—H | C—Br | S | O |
| I-T1-2 | C—Cl | C-i-$C_3F_7$ | C—Cl | 1-(cyano)cyclopropyl | H | C | C—H | C—Br | S | O |
| I-T1-3 | C—Cl | C-i-$C_3F_7$ | C—Cl | cyclopropyl | H | C | C—H | N—$CH_3$ | C—H | O |
| I-T1-4 | C—Cl | C-i-$C_3F_7$ | C—Cl | 1-(cyano)cyclopropyl | H | C | C—H | N—$CH_3$ | C—H | O |
| I-T1-5 | C—Cl | C-i-$C_3F_7$ | C—Cl | 1-(cyano)cyclopropyl | H | C | N | C—H | S | O |
| I-T1-6 | C—Cl | C-i-$C_3F_7$ | C—Cl | benzyl | H | C | C—H | C—Br | S | O |
| I-T1-7 | C—Cl | C-i-$C_3F_7$ | C—Cl | cyclopropyl | H | C | N | C—Cl | S | O |
| I-T1-8 | C—Cl | C-i-$C_3F_7$ | C—Cl | cyclopropyl | H | C | N | C—H | S | O |
| I-T1-9 | C—Cl | C-i-$C_3F_7$ | C—Cl | cyclopropyl | H | C | C—H | N—$CH_3$ | C—Cl | O |
| I-T1-10 | C—Cl | C-i-$C_3F_7$ | C—Cl | 1-(cyano)cyclopropyl | H | C | C—H | C—$CH_3$ | S | O |
| I-T1-11 | C—Cl | C-i-$C_3F_7$ | C—Cl | cyclopropyl | H | C | C—H | C—$CH_3$ | S | O |
| I-T1-12 | C—Cl | C-i-$C_3F_7$ | C—Cl | cyclopropyl | H | C | C—H | C—H | S | O |
| I-T1-13 | C—Cl | C-i-$C_3F_7$ | C—Cl | 1-(cyano)cyclopropyl | H | C | C—H | C—H | S | O |
| I-T1-14 | C—Cl | C-i-$C_3F_7$ | C—Cl | cyclopropyl | H | C | C—H | C—I | S | O |
| I-T1-15 | C—Cl | C-i-$C_3F_7$ | C—Cl | 1-(cyano)cyclopropyl | H | C | C—H | C—I | S | O |
| I-T1-16 | C—Cl | C-i-$C_3F_7$ | C—Cl | cyclopropyl | H | C | C—H | C—Cl | S | O |
| I-T1-17 | C—Cl | C-i-$C_3F_7$ | C—Cl | 1-(cyano)cyclopropyl | H | C | C—H | C—Cl | S | O |
| I-T1-18 | C—Cl | C-i-$C_3F_7$ | C—Cl | 1-(cyano)cyclopropyl | $CH_3$ | C | C—H | C—Cl | S | O |

$B_2$ and $B_4$ = CH

NMR Data of Selected Examples

NMR Peak List Method

The $^1$H NMR data of selected examples are stated in the form of $^1$H NMR peak lists. For each signal peak, first the δ value in ppm and then the signal intensity in round brackets are listed. The pairs of δ value-signal intensity numbers for different signal peaks are listed with separation from one another by semicolons.

The peak list for one example therefore takes the form of:
δ$_1$ (intensity$_1$); δ$_2$ (intensity$_2$); . . . ; δ$_i$ (intensity$_i$); . . . ; δ$_n$ (intensity$_n$)

The intensity of sharp signals correlates with the height of the signals in a printed example of an NMR spectrum in cm and shows the true ratios of the signal intensities. In the case of broad signals, several peaks or the middle of the signal and the relative intensity thereof may be shown in comparison to the most intense signal in the spectrum.

For calibration of the chemical shift of $^1$H NMR spectra, we use tetramethylsilane and/or the chemical shift of the solvent, particularly in the case of spectra which are measured in DMSO. Therefore, the tetramethylsilane peak may but need not occur in NMR peak lists.

The lists of the $^1$H NMR peaks are similar to the conventional $^1$H NMR printouts and thus usually contain all peaks listed in a conventional NMR interpretation.

In addition, like conventional $^1$H NMR printouts, they may show solvent signals, signals of stereoisomers of the target compounds which are likewise provided by the invention, and/or peaks of impurities.

In the reporting of compound signals within the delta range of solvents and/or water, our lists of $^1$H NMR peaks show the standard solvent peaks, for example peaks of DMSO in DMSO-D$_6$ and the peak of water, which usually have a high intensity on average.

The peaks of stereoisomers of the target compounds and/or peaks of impurities usually have a lower intensity on average than the peaks of the target compounds (for example with a purity of >90%).

Such stereoisomers and/or impurities may be typical of the particular preparation process. Their peaks can thus help in identifying reproduction of our preparation process with reference to "by-product fingerprints".

An expert calculating the peaks of the target compounds by known methods (MestreC, ACD simulation, but also with empirically evaluated expected values) can, if required, isolate the peaks of the target compounds, optionally using additional intensity filters. This isolation would be similar to the relevant peak picking in conventional 1H NMR interpretation.

Further details of 1H NMR peak lists can be found in the Research Disclosure Database Number 564025.

Example I-T1-1: $^1$H-NMR (400 MHz, d$_6$-DMSO):
δ = 8.5815(8.5); 8.4144(0.5); 8.3785(4.3); 8.3694(4.1); 8.2844(0.5); 8.2324(8.6); 8.0957(16.0); 7.3923(9.1); 3.4571(0.3); 3.3327(46.0); 2.9359(0.3); 2.8979(0.4); 2.8146(3.1); 2.8051(3.1); 2.6762(2.7); 2.5053(283.4); 2.3309(2.4); 1.9794(0.5); 1.9616(0.4); 1.4446 (0.4); 1.2380(5.2); 1.1519(0.4); 0.8558(0.9); 0.8393(0.5); 0.8108(0.4); 0.7124(6.7); 0.6989(6.6); 0.6431(0.6); 0.5478(7.8); 0.3374(0.3); 0.1485(0.7); 0.0030(75.4); −0.1475(0.6)

Example I-T1-2: $^1$H-NMR (300.1 MHz, d$_6$-DMSO):
δ = 9.2672(6.6); 8.5953(10.3); 8.2352(10.3); 8.0937(16.0); 7.7245(0.4); 7.6933(0.4); 7.4616(12.2); 4.0248(0.9); 4.0027(0.9); 3.3259(50.1); 2.7279(0.5); 2.5076(67.5); 2.5019(87.0); 2.4962(61.3); 2.2713(0.6); 2.0757(7.8); 1.6085(2.3); 1.5894(5.7); 1.5801(5.9); 1.5629(2.6); 1.3333(0.4); 1.2820(2.9); 1.2642(5.9); 1.2551(6.0); 1.2357(3.1); 1.1385(0.4); 1.1153(0.5); 0.9425(2.6); 0.9200(2.6); 0.0107(2.6); −0.0001(58.8); −0.0111(2.2)

Example I-T1-3: $^1$H-NMR (400.2 MHz, d$_6$-DMSO):
δ = 8.1742(5.8); 8.0629(1.9); 8.0467(9.7); 7.9512(5.8); 7.1863(3.3); 7.1821(3.4); 6.9048(3.4); 6.9003(3.4); 6.5313(0.7); 3.8492(16.0); 3.3241(43.4); 3.3005(1.9); 2.7787(0.6); 2.7689(0.8); 2.7606(1.3); 2.7509(1.2); 2.7425(0.8); 2.7329(0.6); 2.6711(0.5); 2.5066(60.9); 2.5023(80.1); 2.4980(59.3); 2.3291(0.6); 2.0759(0.9); 1.1475(0.5); 0.6780(0.9); 0.6647(2.2); 0.6599(3.0); 0.6481(2.7); 0.6421(2.3); 0.6312(1.0); 0.5388(1.1); 0.5283(3.2); 0.5218(2.9); 0.5130(2.4); 0.5007(0.7); 0.0007(30.5)

Example I-T1-4: $^1$H-NMR (300.1 MHz, d$_6$-DMSO):
δ = 8.9155(3.6); 8.3831(0.4); 8.2068(6.3); 8.0499(9.4); 7.9672(6.4); 7.2960(3.3); 7.2906(3.4); 6.9945(3.4); 6.9884(3.4); 6.5453(1.4); 3.8791(16.0); 3.3211(95.6); 3.2977(0.8); 2.7273(1.2); 2.7210(0.9); 2.5128(77.7); 2.5071(151.3); 2.5013(199.3); 2.4955(139.3); 2.2772(0.9); 2.2715(1.2); 2.2653(0.9); 1.5457(1.2); 1.5267(3.2); 1.5175(3.4); 1.5007(1.6); 1.2927(1.4); 1.2515(1.6); 1.2343(3.6); 1.2251(3.4); 1.2061(1.2); 1.0679(0.7); 0.0108(1.1); −0.0001(32.6); −0.0112(1.1)

Example I-T1-5: $^1$H-NMR (300.1 MHz, d$_6$-DMSO):
δ = 9.3332(5.8); 8.9075(0.7); 8.8701(10.7); 8.4267(10.4); 8.3503(14.4); 8.1109(16.0); 6.5159(3.8); 5.7424(1.3); 3.6057(0.6); 3.3890(0.8); 3.3134(232.3); 3.2896(8.2); 2.7270(5.2); 2.7211(3.8); 2.6517(0.7); 2.5849(1.2); 2.5065(611.3); 2.5007(800.6); 2.4951(565.5); 2.2766(3.7); 2.2704(4.6); 2.1633(1.0); 2.0899(1.2); 2.0495(0.7); 1.5985(2.2); 1.5789(5.3); 1.5703(5.8); 1.5529(2.6); 1.3563(3.0); 1.3396(5.6); 1.3301(5.4); 1.3117(2.0); 1.2342(0.9); 0.8563(0.6); 0.1949(2.2); 0.0108(22.0); −0.0001(542.6); −0.0111(19.3); −0.1987(2.2); −2.2299(0.6); −3.3736(0.6); −3.5153(0.7)

Example I-T1-6: $^1$H-NMR (300.1 MHz, d$_6$-DMSO):
δ = 8.9117(1.5); 8.8923(2.8); 8.8726(1.4); 8.5969(9.0); 8.2411(9.0); 8.0908(14.1); 7.4878(9.8); 7.3604(16.0); 7.3486(11.2); 7.3447(11.5); 7.3243(1.0); 7.3159(1.2); 7.3003(0.5); 7.2852(1.5); 7.2743(1.8); 7.2644(1.7); 7.2565(2.0); 7.2479(1.2); 4.4546(6.5); 4.4348(6.3); 3.3321(56.3); 2.5076(33.8); 2.5020(42.7); 2.4965(30.7); 2.0754(0.5); 1.2332(0.5); −0.0002(25.8)

Example I-T1-7: $^1$H-NMR (300.1 MHz, d$_6$-DMSO):
δ = 12.6233(0.5); 8.8976(11.3); 8.8958(11.3); 8.4627(11.3); 8.4609(11.2); 8.4192(2.9); 8.4055(3.2); 8.1165(16.0); 6.5302(5.0); 3.4187(1.6); 3.3239(762.4); 3.3007(7.4); 3.2233(0.8); 2.8662(1.2); 2.8516(1.3); 2.8426(2.2); 2.8285(1.9); 2.8047(1.2); 2.7272(2.3); 2.7213(1.8); 2.5900(1.1); 2.5133(143.4); 2.5074(283.9); 2.5014(375.6); 2.4955(256.2); 2.4897(115.9); 2.3865(0.6); 2.2774(1.8); 2.2712(2.3); 2.0859(1.0); 1.2400(0.9); 1.1464(2.2); 0.7543(1.3); 0.7300(4.7); 0.7041(3.7); 0.6911(2.5); 0.6661(0.8); 0.6414(2.4); 0.6268(5.5); 0.6140(4.6); 0.5894(1.1); 0.1952(0.7); 0.0108(7.5); −0.0001(193.4); −0.0111(5.8); −0.1980(0.9)

Example I-T1-8: $^1$H-NMR (300.1 MHz, d$_6$-DMSO):
δ = 8.8655(10.9); 8.4340(10.8); 8.2977(2.9); 8.2832(2.9); 8.1991(14.8); 8.1077(16.0); 6.5160(0.5); 3.3135(35.2); 3.2897(1.2); 2.9081(0.4); 2.8950(0.9); 2.8824(1.3); 2.8703(1.9); 2.8573(1.8); 2.8331(0.9); 2.8188(0.3); 2.7270(0.7); 2.5123(49.1); 2.5068(95.0); 2.5010(125.0); 2.4952(87.5); 2.2706(0.8); 2.0737(0.6); 1.2348(0.4); 0.7523(1.0); 0.7273(4.2); 0.7080(3.8); 0.7017(3.6); 0.6896(3.0); 0.6644(2.4); 0.6510(6.5); 0.6410(3.8); 0.6126(1.1); 0.1952(0.4); 0.0108(4.0); 0.0000(99.0); −0.0111(3.5); −0.1990(0.4)

Example I-T1-9: $^1$H-NMR (400.0 MHz, d$_6$-DMSO):
δ = 8.3976(5.6); 8.1968(1.5); 8.1869(1.5); 8.0746(5.5); 8.0489(8.4); 7.0532(5.8); 3.8637(16.0); 3.3216(75.3); 2.9610(0.3); 2.7964(0.5); 2.7869(0.8); 2.7783(1.1); 2.7685(1.2); 2.7600(0.8); 2.7505(0.5); 2.6749(0.5); 2.6706(0.7); 2.6663(0.5); 2.5061(88.6); 2.5017(116.5); 2.4973(85.5); 2.3284(0.7); 2.3237(0.5); 2.0742(6.1); 0.7006(0.7); 0.6877(1.9); 0.6826(2.7); 0.6706(2.5); 0.6645(2.2); 0.6534(0.9); 0.5535(0.9); 0.5430(2.8); 0.5369(2.5); 0.5275(2.2); 0.5152(0.7); 0.0079(0.7); −0.0002(18.7)

Example I-T1-10: $^1$H-NMR (400.0 MHz, d$_6$-DMSO):
δ = 9.0102 (3.5); 8.4825 (5.9); 8.1252 (5.9); 8.0772 (8.9); 7.4589 (5.9); 3.3226 (23.0); 2.6712 (0.4); 2.6668 (0.3); 2.6337 (16.0); 2.5242 (0.9); 2.5065 (42.6); 2.5021 (56.7); 2.4977 (41.8); 2.0862 (0.9); 2.0749 (4.8); 1.5678 (1.3); 1.5536 (3.3); 1.5466 (3.6); 1.5338 (1.5); 1.2738 (1.5); 1.2603 (3.4); 1.2536 (3.6); 1.2391 (1.3); 0.0077 (2.3); −0.0002 (62.2); −0.0083 (2.6)

Example I-T1-11: $^1$H-NMR (400.0 MHz, d$_6$-DMSO):
δ = 8.4543 (5.8); 8.1228 (1.8); 8.1142 (7.3); 8.0723 (8.9); 7.4114 (6.0); 3.3220 (28.2); 2.8194 (0.6); 2.8100 (0.8); 2.8012 (1.2); 2.7914 (1.2); 2.7827 (0.8); 2.7732 (0.6); 2.6708 (0.4); 2.5961 (16.0); 2.5235 (0.8); 2.5101 (20.8); 2.5061 (42.5); 2.5017 (56.7); 2.4973 (41.2); 2.0747 (0.7); 0.7041 (0.7); 0.6913 (2.0); 0.6861 (2.9); 0.6741 (2.6); 0.6682 (2.3); 0.6571 (0.9); 0.5542 (1.0); 0.5438 (3.0); 0.5375 (2.6); 0.5279 (2.4); 0.5158 (0.7); 0.0076 (2.3); −0.0002 (63.7); −0.0084 (2.6)

-continued

Example I-T1-12: ¹H-NMR (400.0 MHz, d₆-DMSO):
δ = 8.5643 (10.2); 8.3084 (3.2); 8.2986 (3.3); 8.2151 (10.4);
8.0821 (16.0); 7.9803 (7.3); 7.6416 (7.2); 3.9294 (0.8); 3.3239 (34.4);
2.8354 (0.3); 2.8251 (1.0); 2.8159 (1.5); 2.8070 (2.2); 2.7975 (2.2);
2.7888 (1.5); 2.7794 (1.0); 2.7690 (0.4); 2.6719 (0.5); 2.5066 (70.2);
2.5027 (90.6); 2.4990 (68.6); 2.3299 (0.5); 1.0695 (4.9); 0.7210 (1.2);
0.7080 (3.8); 0.7032 (5.2); 0.6910 (4.8); 0.6853 (4.2); 0.6742 (1.7);
0.5698 (1.7); 0.5593 (5.3); 0.5528 (5.1); 0.5438 (4.4); 0.5313 (1.2);
0.0000 (9.6)
Example I-T1-13: ¹H-NMR (400.0 MHz, d₆-DMSO):
δ = 9.2167 (6.6); 8.5961 (10.8); 8.2406 (10.8); 8.0864 (16.0);
8.0779 (8.4); 8.0746 (8.1); 7.6590 (7.6) 7.6557 (7.5); 4.0560 (0.8);
4.0382 (2.4); 4.0204 (2.5); 4.0027 (0.8); 3.9282 (0.4); 3.3221 (44.3);
2.6756 (0.6); 2.6712 (0.8); 2.6666 (0.6); 2.5245 (1.9); 2.5110 (48.0);
2.5066 (99.8); 2.5021 (132.6); 2.4976 (94.4); 2.4933 (44.7);
2.3332 (0.5); 2.3288 (0.8); 2.3242 (0.5); 1.9891 (10.7); 1.5862 (2.4);
1.5720 (5.9); 1.5650 (6.3); 1.5521 (2.7); 1.3975 (1.5); 1.2853 (2.9);
1.2719 (5.9); 1.2651 (6.4); 1.2507 (2.4); 1.2353 (0.6); 1.1927 (2.8);
1.1749 (5.7); 1.1571 (2.8); 1.0690 (2.7); 0.0080 (0.6); −0.0001 (18.2);
−0.0083 (0.6)
Example I-T1-14: ¹H-NMR (400.0 MHz, d₆-DMSO):
δ = 8.6192 (0.6); 8.5622 (0.5); 8.5430 (10.1); 8.2947 (3.2);
8.2839 (3.1); 8.2419 (0.8); 8.1934 (10.2); 8.0812 (16.0); 7.3909 (0.4);
7.3014 (10.6); 5.7567 (1.3); 3.4248 (2.4); 2.8374 (0.3); 2.8272 (0.9);
2.8179 (1.4); 2.8091 (2.0); 2.7996 (2.0); 2.7903 (1.4); 2.7812 (1.0);
2.7709 (0.4); 2.6699 (0.8); 2.5012 (151.5); 2.3281 (0.9); 0.7256 (1.1);
0.7122 (3.7); 0.7077 (4.9); 0.6952 (4.6); 0.6897 (4.0); 0.6786 (1.6);
0.5697 (1.6); 0.5591 (5.1); 0.5521 (4.9); 0.5435 (4.3); 0.5315 (1.2);
0.1455 (0.6); 0.0058 (5.7); −0.0004 (125.5); −0.0019 (107.6);
−0.1505 (0.6)
Example I-T1-15: ¹H-NMR (400.0 MHz, d₆-DMSO):
δ = 9.1972 (6.6); 8.5625 (10.4); 8.2010 (10.6); 8.0850 (16.0);
7.3696 (11.4) 6.9083 (0.7) 5.7566 (4.4) 3.3216 (25.6); 2.6712 (0.6);
2.5065 (76.8); 2.5023 (100.2); 2.4982 (74.5); 2.3292 (0.7); 2.0749 (2.1);
1.6008 (2.3); 1.5866 (6.0); 1.5798 (6.5); 1.5668 (2.7); 1.2777 (2.8);
1.2643 (6.2); 1.2576 (6.5); 1.2425 (2.9); 1.2233 (1.3); 1.1916 (0.8);
1.1752 (0.8); 0.8810 (0.8); 0.8641 (0.8); 0.0075 (2.4); −0.0001 (56.4)
Example I-T1-16: ¹H-NMR (400.0 MHz, d₆-DMSO):
δ = 9.1968 (0.4); 8.7769 (1.0); 8.7466 (0.4); 8.5761 (9.3);
8.5621 (0.6) 8.3702 (2.5); 8.3595 (2.6); 8.2724 (1.1); 8.2292 (9.3);
8.2007 (0.6); 8.0858 (16.0); 7.8646 (0.6); 7.4156 (10.1); 7.3687 (0.6);
5.7567 (12.1); 3.3217 (86.6); 2.8437 (0.4); 2.8330 (1.0); 2.8241 (1.4);
2.8148 (2.0); 2.8052 (2.0); 2.7964 (1.3); 2.7863 (0.9); 2.7770 (0.4);
2.6712 (0.9); 2.5062 (129.2); 2.5020 (170.7); 2.4979 (125.2);
2.3284 (0.9); 2.0744 (2.6); 1.5860 (0.4); 1.5797 (0.4); 1.2624 (0.4);
1.2569 (0.4); 0.7379 (0.5); 0.7270 (1.4); 0.7146 (3.3); 0.7093 (4.5);
0.6971 (4.3); 0.6913 (3.6); 0.6802 (1.5); 0.5629 (1.5); 0.5522 (4.5);
0.5455 (4.3); 0.5363 (3.9); 0.5240 (1.4); 0.5069 (0.5); 0.1463 (0.3);
0.0077 (2.5); −0.0002 (68.7); −0.1495 (0.3)
Example I-T1-17: ¹H-NMR (400.0 MHz, d₆-DMSO):
δ = 9.6859 (1.5); 9.2607 (5.2); 8.8019 (2.3); 8.5964 (8.8);
8.2949 (2.4); 8.2366 (8.9); 8.0890 (16.0); 7.4870 (10.3); 3.3210 (33.2);
2.6752 (0.5); 2.6709 (0.7); 2.6665 (0.5); 2.5240 (1.7); 2.5104 (42.9);
2.5062 (89.1); 2.5018 (119.6); 2.4974 (86.3); 2.4932 (41.6);
2.3289 (0.6); 2.3237 (0.5); 1.6520 (0.5); 1.6379 (1.3); 1.6310 (1.3);
1.6175 (0.6); 1.5987 (1.9); 1.5843 (4.8); 1.5774 (5.1); 1.5644 (2.2);
1.2817 (2.2); 1.2682 (4.8); 1.2615 (5.2); 1.2469 (2.4); 1.2329 (1.4);
1.2262 (1.4); 1.2118 (0.5); 0.9264 (0.3); 0.9097 (0.3); 0.0077 (1.6);
−0.0004 (42.8); −0.0086 (1.6)
Example I-T1-18: ¹H-NMR (400.0 MHz, d₆-DMSO):
δ = 8.8156 (1.0); 8.6100 (9.3); 8.3161 (1.2); 8.2652 (8.4);
8.0870 (16.0); 7.3933 (12.2); 5.7553 (1.7); 3.3194 (128.0);
3.0327 (13.4); 2.9944 (2.9); 2.6749 (1.2); 2.6706 (1.8); 2.6665 (1.3);
2.5240 (4.5); 2.5104 (109.0); 2.5061 (227.3); 2.5017 (304.5);
2.4973 (220.5); 2.4934 (108.7); 2.3327 (1.3); 2.3285 (1.7);
2.3244 (1.3); 2.0739 (0.4); 2.0084 (0.4); 1.9891 (0.4); 1.7318 (0.4);
1.7190 (0.5); 1.7076 (0.4); 1.6376 (2.3); 1.4846 (0.4); 1.4441 (2.3);
1.4305 (4.3); 1.4245 (4.4); 1.4085 (1.4); 1.2354 (3.1); 0.8542 (0.7);
0.1463 (0.8); 0.0079 (5.5); −0.0001 (165.6); −0.0084 (7.0);
−0.1495 (0.8)

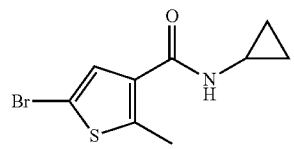

Intermediate (B); ¹H-NMR (400.0 MHz, d₆-DMSO):
δ = 8.0939 (2.6); 8.0851 (2.6); 7.3625 (16.0); 3.3216 (15.5);
2.7946 (0.5); 2.7845 (1.4); 2.7749 (2.0); 2.7663 (3.1); 2.7563 (3.2);
2.7478 (2.0); 2.7382 (1.5); 2.7280 (0.5); 2.5532 (49.0); 2.5242 (0.7);
2.5106 (16.9); 2.5065 (35.2); 2.5020 (47.1); 2.4976 (34.3);
2.4935 (16.9); 0.6823 (1.8); 0.6699 (5.2); 0.6645 (7.2); 0.6525 (6.9);
0.6465 (5.6); 0.6353 (2.6); 0.6141 (0.4); 0.5962 (0.4); 0.5698 (0.3);
0.5596 (0.4);0.5303 (2.6); 0.5198 (7.4); 0.5131 (6.6); 0.5099 (6.2);
0.5035 (5.8); 0.4916 (1.8); −0.0002 (8.9); −0.0085 (0.4)

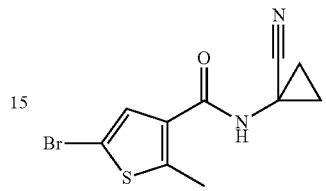

Intermediate (C); Z-2: ¹H-NMR (400.0 MHz, d₆-DMSO):
δ = 8.9557 (2.0); 7.4046 (5.3); 3.3226 (6.4); 2.5921 (16.0);
2.5069 (12.6); 2.5024 (16.8); 2.4980 (12.3); 1.5434 (1.1); 1.5294 (3.0);
1.5222 (3.0); 1.5092 (1.4); 1.2531 (1.4); 1.2399 (3.0); 1.2328 (3.2);
1.2187 (1.1); −0.0002 (3.5)

Biological Examples

*Ctenocephalides felis*—In Vitro Contact Tests with Adult Cat Fleas

For the coating of the test tubes, 9 mg of active ingredient are first dissolved in 1 ml of acetone p.a. and then diluted to the desired concentration with acetone p.a. 250 μl of the solution are distributed homogeneously on the inner walls and the base of a 25 ml glass tube by turning and rocking on an orbital shaker (rocking rotation at 30 rpm for 2 h). With 900 ppm of active ingredient solution and internal surface area 44.7 cm², given homogeneous distribution, an area-based dose of 5 μg/cm² is achieved.

After the solvent has evaporated off, the tubes are populated with 5-10 adult cat fleas (*Ctenocephalides felis*), sealed with a perforated plastic lid and incubated in a horizontal position at room temperature and ambient humidity. After 48 h, efficacy is determined. To this end, the tubes are stood upright and the fleas are knocked to the base of the tube. Fleas which remain motionless at the base or move in an uncoordinated manner are considered to be dead or moribund.

A substance shows good efficacy against *Ctenocephalides felis* if at least 80% efficacy was achieved in this test at an application rate of 5 μg/cm². 100% efficacy means that all the fleas were dead or moribund. 0% efficacy means that no fleas were harmed.

In this test, for example, the following compounds from the preparation examples shows an efficacy of 100% at an application rate of 5 μg/cm² (=500 g/ha): 1, 11, 12

*Rhipicephalus sanguineus*—In Vitro Contact Tests with Adult Brown Dog Ticks

For the coating of the test tubes, 9 mg of active ingredient are first dissolved in 1 ml of acetone p.a. and then diluted to the desired concentration with acetone p.a. 250 μl of the solution are distributed homogeneously on the inner walls and the base of a 25 ml glass tube by turning and rocking on an orbital shaker (rocking rotation at 30 rpm for 2 h). With 900 ppm of active ingredient solution and internal surface area 44.7 cm², given homogeneous distribution, an area-based dose of 5 μg/cm² is achieved.

After the solvent has evaporated off, the tubes are populated with 5-10 adult dog ticks (*Rhipicephalus sanguineus*), sealed with a perforated plastic lid and incubated in a horizontal position in the dark at room temperature and ambient humidity. After 48 h, efficacy is determined. To this end, the ticks are knocked to the base of the tube and incubated on a hotplate at 45-50° C. for not more than 5 min. Ticks which remain motionless on the base or move in such an uncoordinated manner that they are unable to deliberately avoid the heat by climbing upwards are considered to be dead or moribund.

A substance shows good activity against *Rhipicephalus sanguineus* if, in this test, an efficacy of at least 80% was achieved at an application rate of 5 µg/cm². An efficacy of 100% means that all the ticks were dead or moribund. 0% efficacy means that none of the ticks were harmed.

In this test, for example, the following compounds from the preparation examples show an efficacy of 100% at an application rate of 5 µg/cm² (=500 g/ha): 1, 2, 3, 11, 12, 14

In this test, for example, the following compounds from the preparation examples show an efficacy of 80% at an application rate of 5 µg/cm² (=500 g/ha): 15

*Boophilus microplus*—Dip Test

Test animals: cattle ticks (*Boophilus microplus*) Parkhurst strain, SP-resistant Solvent: dimethyl sulfoxide 10 mg of active ingredient are dissolved in 0.5 ml of dimethyl sulfoxide. To produce a suitable formulation, the active ingredient solution is diluted with water to the concentration desired in each case. This active ingredient formulation is pipetted into tubes. 8-10 engorged adult female cattle ticks (*Boophilus microplus*) are transferred into a further tube with holes. The tube is immersed into the active ingredient formulation, and all the ticks are completely wetted. After the liquid has run out, the ticks are transferred on filter discs into plastic dishes and stored in a climate-controlled room.

Efficacy is assessed after 7 days by laying of fertile eggs. Eggs which are not visibly fertile are stored in a climate-controlled cabinet until the larvae hatch after about 42 days. An efficacy of 100% means that none of the ticks has laid any fertile eggs; 0% means that all the eggs are fertile.

In this test, for example, the following compounds of the preparation examples show an efficacy of 100% at an application rate of 100 ppm: 1, 2, 11, 14

*Boophilus microplus*—Injection Test

Solvent: dimethyl sulfoxide

To produce a suitable active compound preparation, 10 mg of active compound are mixed with 0.5 ml of solvent and the concentrate is diluted to the desired concentration with solvent.

1 µl of the active ingredient solution is injected into the abdomen of 5 engorged adult female cattle ticks (*Boophilus microplus*). The animals are transferred into dishes and kept in a climate-controlled room.

Efficacy is assessed after 7 days by laying of fertile eggs. Eggs which are not visibly fertile are stored in a climate-controlled cabinet until the larvae hatch after about 42 days. An efficacy of 100% means that none of the ticks has laid any fertile eggs; 0% means that all the eggs are fertile.

In this test, for example, the following compounds from the preparation examples show an efficacy of 100% at an application rate of 20 µg/animal: 1, 2, 3, 4, 6, 7, 10, 11, 13, 14, 15

*Ctenocephalides felis*—Oral Test

Solvent: dimethyl sulfoxide

To produce a suitable active ingredient formulation, 10 mg of active ingredient are mixed with 0.5 ml of dimethyl sulfoxide. Dilution with citrated cattle blood gives the desired concentration.

About 20 unfed adult cat fleas (*Ctenocephalides felis*) are placed into a chamber which is closed at the top and bottom with gauze. A metal cylinder whose bottom end is closed with parafilm is placed onto the chamber. The cylinder contains the blood/active ingredient formulation, which can be imbibed by the fleas through the parafilm membrane.

After 2 days, the rate of extermination in % is determined. 100% means that all of the fleas have been killed; 0% means that none of the fleas have been killed.

In this test, for example, the following compounds of the preparation examples show an efficacy of 100% at an application rate of 100 ppm: 1, 2, 3, 4, 5, 6, 8, 10, 11, 12, 13, 14, 15

*Lucilia cuprina* Test

Solvent: dimethyl sulfoxide

To produce a suitable active ingredient formulation, 10 mg of active ingredient are mixed with 0.5 ml of dimethyl sulfoxide, and the concentrate is diluted with water to the desired concentration.

About 20 L1 larvae of the Australian sheep blowfly (*Lucilia cuprina*) are transferred into a test vessel containing minced horsemeat and the active compound preparation of the desired concentration.

After 2 days, the rate of extermination in % is determined. 100% means that all the larvae have been killed; 0% means that no larvae have been killed.

In this test, for example, the following compounds of the preparation examples show an efficacy of 100% at an application rate of 100 ppm: 1, 2, 3, 4, 10, 11, 12, 13, 14, 15

In this test, for example, the following compounds from the preparation examples show an efficacy of 95% at an application rate of 100 ppm: 6

In this test, for example, the following compounds of the preparation examples show an efficacy of 80% at an application rate of 100 ppm: 5, 8

*Musca domestica* Test

Solvent: dimethyl sulfoxide

To produce a suitable active ingredient formulation, 10 mg of active ingredient are mixed with 0.5 ml of dimethyl sulfoxide, and the concentrate is diluted with water to the desired concentration.

Vessels containing a sponge treated with sugar solution and the active ingredient formulation of the desired concentration are populated with 10 adult houseflies (*Musca domestica*).

After 2 days, the rate of extermination in % is determined. 100% means that all of the flies have been killed; 0% means that none of the flies have been killed.

In this test, for example, the following compounds of the preparation examples show an efficacy of 100% at an application rate of 100 ppm: 1, 2, 10, 11, 12, 13, 14, 15

In this test, for example, the following compounds from the preparation examples show an efficacy of 90% at an application rate of 100 ppm: 5

*Myzus persicae*—Oral Test

| Solvent: | 100 parts by weight of acetone |
|---|---|

To produce a suitable active compound preparation, 1 part by weight of active compound is dissolved with the specified amounts by weight of solvent and made up to the desired concentration with water.

50 ul of the active compound preparation are transferred to microtiter plates and made up to a final volume of 200 µl with 150 µl of IPL41 insect medium (33%+15% sugar). Then the plates are sealed with parafilm through which a mixed population of the green peach aphid (*Myzus persicae*), which is located in a second microtiter plate, can pierce and absorb the solution.

After 5 days, the efficacy in % is determined. 100% means that all the aphids have been killed; 0% means that no aphids have been killed.

In this test, for example, the following compounds from the preparation examples show an efficacy of 100% at an application rate of 4 ppm: 10, 12, 16

In this test, for example, the following compounds from the preparation examples show efficacy of 90% at an application rate of 4 ppm: 11

*Myzus persicae*—Spray Test

| Solvent: | 78 parts by weight of acetone |
| --- | --- |
| | 1.5 parts by weight of dimethylformamide |
| Emulsifier: | alkylaryl polyglycol ether |

To produce a suitable active ingredient formulation, 1 part by weight of active ingredient is dissolved with the specified parts by weight of solvent and made up to the desired concentration with water containing an emulsifier concentration of 1000 ppm. To produce further test concentrations, the formulation is diluted with emulsifier-containing water.

Discs of Chinese cabbage leaves (*Brassica pekinensis*) infested by all stages of the green peach aphid (*Myzus persicae*) are sprayed with an active compound preparation of the desired concentration.

After 5 days, the efficacy in % is determined. 100% means that all the aphids have been killed; 0% means that no aphids have been killed.

In this test, for example, the following compounds from the preparation examples show an efficacy of 100% at an application rate of 100 g/ha: 1, 2, 16

In this test, for example, the following compounds from the preparation examples show an efficacy of 90% at an application rate of 100 g/ha: 11

*Phaedon cochleariae*—Spray Test

| Solvent: | 78.0 parts by weight of acetone |
| --- | --- |
| | 1.5 parts by weight of dimethylformamide |
| Emulsifier: | alkylaryl polyglycol ether |

To produce a suitable active ingredient formulation, 1 part by weight of active ingredient is dissolved with the specified parts by weight of solvent and made up to the desired concentration with water containing an emulsifier concentration of 1000 ppm. To produce further test concentrations, the formulation is diluted with emulsifier-containing water.

Discs of Chinese cabbage leaves (*Brassica pekinensis*) are sprayed with an active compound preparation of the desired concentration and, after drying, populated with larvae of the mustard beetle (*Phaedon cochleariae*).

After 7 days, the efficacy in % is determined. 100% means that all the beetle larvae have been killed; 0% means that no beetle larvae have been killed.

In this test, for example, the following compounds from the preparation examples show an efficacy of 100% at an application rate of 100 g/ha: 1, 2, 3, 4, 5, 9, 10, 11, 12, 13, 14, 15, 16, 17, 18

In this test, for example, the following compounds from the preparation examples show efficacy of 83% at an application rate of 100 g/ha: 7, 8

*Spodoptera frugiperda*—Spray Test

| Solvent: | 78.0 parts by weight of acetone |
| --- | --- |
| | 1.5 parts by weight of dimethylformamide |
| Emulsifier: | alkylaryl polyglycol ether |

To produce a suitable active ingredient formulation, 1 part by weight of active ingredient is dissolved with the specified parts by weight of solvent and made up to the desired concentration with water containing an emulsifier concentration of 1000 ppm. To produce further test concentrations, the formulation is diluted with emulsifier-containing water.

Leaf discs of maize (*Zea mays*) are sprayed with an active ingredient formulation of the desired concentration and, after drying, populated with caterpillars of the armyworm (*Spodoptera frugiperda*).

After 7 days, the efficacy in % is determined. 100% means that all the caterpillars have been killed; 0% means that no caterpillar has been killed.

In this test, for example, the following compounds from the preparation examples show an efficacy of 100% at an application rate of 100 g/ha: 1, 2, 3, 6, 9, 10, 11, 12, 13, 14, 15, 16, 17, 18

*Tetranychus urticae*—Spray Test, OP-Resistant

| Solvent: | 78.0 parts by weight of acetone |
| --- | --- |
| | 1.5 parts by weight of dimethylformamide |
| Emulsifier: | alkylaryl polyglycol ether |

To produce a suitable active ingredient formulation, 1 part by weight of active ingredient is dissolved with the specified parts by weight of solvent and made up to the desired concentration with water containing an emulsifier concentration of 1000 ppm. To produce further test concentrations, the formulation is diluted with emulsifier-containing water.

Discs of bean leaves (*Phaseolus vulgaris*) infested with all stages of the greenhouse red spider mite (*Tetranychus urticae*) are sprayed with an active compound preparation of the desired concentration.

After 6 days, the efficacy in % is determined. 100% means that all the spider mites have been killed; 0% means that no spider mites have been killed.

In this test, for example, the following compounds from the preparation examples show an efficacy of 100% at an application rate of 100 g/ha: 10, 11, 13, 14, 15, 16, 17

In this test, for example, the following compounds from the preparation examples show efficacy of 100% at an application rate of 20 g/ha: 1, 10, 11, 17

In this test, for example, the following compounds from the preparation examples show an efficacy of 90% at an application rate of 20 g/ha: 2, 13, 15, 16

*Anopheles* Test (ANPHGB Surface Treatment)

Solvent: acetone+2000 ppm rapeseed oil methyl ester (RME)

To produce a suitable active compound formulation, the active compound is dissolved in the solvent (2 mg/ml). The active compound formulation is pipetted onto a glazed tile and, after it has dried off, adult mosquitoes of the species *Anopheles gambiae* strain RSPH (homozygot kdr) are placed onto the treated tile. The exposure time is 30 minutes.

24 hours after contact with the treated surface, mortality in % is determined. 100% means that all mosquitoes have been killed; 0% means that none of the mosquitoes have been killed.

In this test, for example, the following compounds from the preparation examples show efficacy of 80-100% at an application rate of 100 mg/m$^2$: 1, 2, 3, 8, 6, 9, 10, 14, 15.

Anopheles Test (ANPHFU Surface Treatment)

Solvent: acetone+2000 ppm rapeseed oil methyl ester (RME)

To produce a suitable active compound formulation, the active compound is dissolved in the solvent (2 mg/ml). The active compound formulation is pipetted onto a glazed tile and, after it has dried off, adult mosquitoes of the species *Anopheles funestus* strain FUMOZ-R (Hunt et al., Med Vet Entomol. 2005 September; 19(3):271-5) are placed onto the treated tile. The exposure time is 30 minutes.

24 hours after contact with the treated surface, mortality in % is determined. 100% means that all mosquitoes have been killed; 0% means that none of the mosquitoes have been killed.

In this test, for example, the following compounds from the preparation examples show efficacy of 80-100% at an application rate of 100 mg/m$^2$: 1, 2, 9, 10, 14, 15.

Aedes Test (AEDSAE Surface Treatment)

Solvent: acetone+2000 ppm rapeseed oil methyl ester (RME)

To produce a suitable active compound formulation, the active compound is dissolved in the solvent (2 mg/ml). The active compound formulation is pipetted onto a glazed tile and, after it has dried off, adult mosquitoes of the species *Aedes aegypti* strain MONHEIM are placed onto the treated tile. The exposure time is 30 minutes.

24 hours after contact with the treated surface, mortality in % is determined. 100% means that all mosquitoes have been killed; 0% means that none of the mosquitoes have been killed.

In this test, for example, the following compounds from the preparation examples show efficacy of 80-100% at an application rate of 100 mg/m$^2$: 1, 2, 9, 10, 13, 14, 15.

Contrasting Examples

*Phaedon cochleariae*—Spray Test (PHAECO)

| Solvent: | 78.0 parts by weight of acetone |
| | 1.5 parts by weight of dimethylformamide |
| Emulsifier: | alkylaryl polyglycol ether |

To produce a suitable active compound formulation, 1 part by weight of active compound is dissolved with the specified parts by weight of solvent and made up to the desired concentration with water containing an emulsifier concentration of 1000 ppm. To produce further test concentrations, the formulation is diluted with emulsifier-containing water.

Discs of Chinese cabbage leaves (*Brassica pekinensis*) are sprayed with an active compound formulation of the desired concentration and, after drying, populated with larvae of the mustard beetle (*Phaedon cochleariae*).

After the desired time, the efficacy in % is determined. 100% means that all the beetle larvae have been killed; 0% means that no beetle larvae have been killed.

In this test, for example, the following compounds from the preparation examples show a superior efficacy compared to the prior art: see Table II

*Spodoptera frugiperda*—Spray Test (SPODFR)

| Solvent: | 78.0 parts by weight of acetone |
| | 1.5 parts by weight of dimethylformamide |
| Emulsifier: | alkylaryl polyglycol ether |

To produce a suitable active compound formulation, 1 part by weight of active compound is dissolved with the specified parts by weight of solvent and made up to the desired concentration with water containing an emulsifier concentration of 1000 ppm. To produce further test concentrations, the formulation is diluted with emulsifier-containing water.

Leaf discs of maize (*Zea mays*) are sprayed with an active compound formulation of the desired concentration and, after drying, populated with caterpillars of the armyworm (*Spodoptera frugiperda*).

After the desired time, the efficacy in % is determined. 100% means that all the caterpillars have been killed; 0% means that no caterpillar has been killed.

In this test, for example, the following compounds from the preparation examples show a superior efficacy compared to the prior art: see Table II

*Myzus Persicae*—Spray Test (MYZUPE)

| Solvent: | 78.0 parts by weight of acetone |
| | 1.5 parts by weight of dimethylformamide |
| Emulsifier: | alkylaryl polyglycol ether |

To produce a suitable active compound formulation, 1 part by weight of active compound is dissolved with the specified parts by weight of solvent and made up to the desired concentration with water containing an emulsifier concentration of 1000 ppm. To produce further test concentrations, the formulation is diluted with emulsifier-containing water.

Discs of Chinese cabbage leaves (*Brassica pekinensis*) infested with all stages of the green peach aphid (*Myzus persicae*) are sprayed with an active compound formulation of the desired concentration.

After the desired time, the efficacy in % is determined. 100% means that all the aphids have been killed; 0% means that no aphids have been killed.

In this test, for example, the following compounds from the preparation examples show a superior efficacy compared to the prior art: see Table II

*Tetranychus urticae*—Spray Test; OP-Resistant (TETRUR)

| Solvent: | 78.0 parts by weight of acetone |
| | 1.5 parts by weight of dimethylformamide |
| Emulsifier: | alkylaryl polyglycol ether |

To produce a suitable active compound formulation, 1 part by weight of active compound is dissolved with the specified parts by weight of solvent and made up to the desired concentration with water containing an emulsifier concentration of 1000 ppm. To produce further test concentrations, the formulation is diluted with emulsifier-containing water.

Discs of bean leaves (*Phaseolus vulgaris*) infested with all stages of the greenhouse red spider mite (*Tetranychus urticae*) are sprayed with an active compound formulation of the desired concentration.

After the desired time, the efficacy in % is determined. 100% means that all the spider mites have been killed; 0% means that no spider mites have been killed.

In this test, for example, the following compounds from the preparation examples show a superior efficacy compared to the prior art: see Table II

TABLE II

| Substance | Structure | Object | Concentration | % efficacy | dat |
|---|---|---|---|---|---|
| Example No. 36 WO2012/000896 | 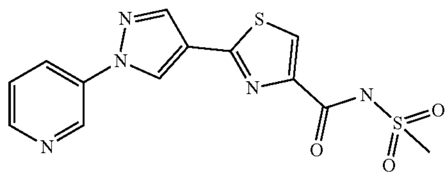 [SMILES: CS(=O)(=O)NC(=O)c1csc(-c2cnn(-c3cccnc3)c2)n1] | PHAECO | 500 g ai/ha | 0 | 7 dat |
| | | SPODFR | 500 g ai/ha | 0 | 7 dat |
| | | MYZUPE | 100 g ai/ha | 0 | 6 dat |
| | | TETRUR | 500 g ai/ha | 0 | 6 dat |
| Example No. I-T1-1 inventive | 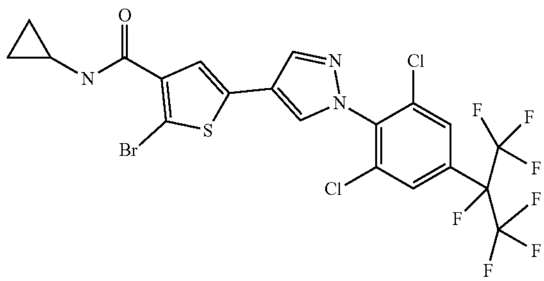 [SMILES: O=C(NC1CC1)c1cc(-c2cnn(-c3c(Cl)cc(C(F)(C(F)(F)F)C(F)(F)F)cc3Cl)c2)sc1Br] | PHAECO | 100 g ai/ha | 100 | 7 dat |
| | | SPODFR | 100 g ai/ha | 100 | 7 dat |
| | | MYZUPE | 100 g ai/ha | 100 | 5 dat |
| | | TETRUR | 100 g ai/ha | 70 | 6 dat |

The invention claimed is:

1. A compound of formula (I)

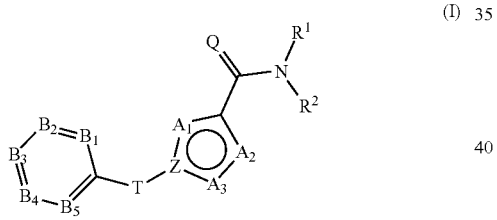

in which $R^1$ is H, $C_1$-$C_6$-alkyl, $C_2$-$C_6$-alkenyl, $C_2$-$C_6$-alkynyl, $C_3$-$C_7$-cycloalkyl, $C_1$-$C_6$-alkylcarbonyl, $C_1$-$C_6$-alkoxycarbonyl, $C_6$-,$C_{10}$-,$C_{14}$-aryl($C_1$-$C_3$)-alkyl, 3, 4, 5, 6, 7, 8, 9 or 10-membered heterocyclyl or 3, 4, 5, 6, 7, 8, 9 or 10-membered-heterocyclyl($C_1$-$C_3$)-alkyl, optionally in each case mutually independently substituted by one or more substituents, selected from the group consisting of amino, hydroxyl, halogen, nitro, cyano, isocyano, mercapto, isothiocyanato, $C_1$-$C_4$-carboxyl, carbonamide, $SF_5$, aminosulfonyl, $C_1$-$C_4$-alkyl, $C_3$-$C_4$-cycloalkyl, $C_2$-$C_4$-alkenyl, $C_5$-$C_6$-cycloalkenyl, $C_2$-$C_4$-alkynyl, N-mono-$C_1$-$C_4$-alkylamino, N,N-di-$C_1$-$C_4$-alkylamino, N—$C_1$-$C_4$-alkanoylamino, $C_1$-$C_4$-alkoxy, $C_2$-$C_4$-alkenyloxy, $C_2$-$C_4$-alkynyloxy, $C_3$-$C_4$-cycloalkoxy, $C_5$-$C_6$-cycloalkenyloxy, $C_1$-$C_4$-alkoxycarbonyl, $C_2$-$C_4$-alkenyloxycarbonyl, $C_2$-$C_4$-alkynyloxycarbonyl, $C_6$-,$C_{10}$-,$C_{14}$-aryloxycarbonyl, $C_1$-$C_4$-alkanoyl, $C_2$-$C_4$-alkenylcarbonyl, $C_2$-$C_4$-alkynylcarbonyl, $C_6$-,$C_{10}$-,$C_{14}$-arylcarbonyl, $C_1$-$C_4$-alkylsulfanyl, $C_3$-$C_4$-cycloalkylsulfanyl, $C_1$-$C_4$-alkylthio, $C_2$-$C_4$-alkenylthio, $C_5$-$C_6$-cycloalkenylthio, $C_2$-$C_4$-alkynylthio, $C_1$-$C_4$-alkylsulfenyl and $C_1$-$C_4$-alkylsulfinyl, wherein both enantiomers of the $C_1$-$C_4$-alkylsulfinyl group are included, $C_1$-$C_4$-alkylsulfonyl, N-mono-$C_1$-$C_4$-alkylaminosulfonyl, N,N-di-$C_1$-$C_4$-alkylaminosulfonyl, $C_1$-$C_4$-alkylphosphinyl, $C_1$-$C_4$-alkylphosphonyl, wherein for $C_1$-$C_4$-alkylphosphinyl or $C_1$-$C_4$-alkylphosphonyl both enantiomers are included, N—$C_1$-$C_4$-alkylaminocarbonyl, N,N-di-$C_1$-$C_4$-alkylaminocarbonyl, N—$C_1$-$C_4$-alkanoylaminocarbonyl, N—$C_1$-$C_4$-alkanoyl-N—$C_1$-$C_4$-alkylaminocarbonyl, $C_6$-,$C_{10}$-,$C_{14}$-aryl, $C_6$-,$C_{10}$-,$C_{14}$-aryloxy, benzyl, benzyloxy, benzylthio, $C_6$-,$C_{10}$-,$C_{14}$-arylthio, $C_6$-,$C_{10}$-,$C_{14}$-arylamino, benzylamino, heterocyclyl and trialkylsilyl;

$R^2$ is H or $C_1$-$C_6$-alkyl, optionally substituted by one or more substituents mutually independently selected from the group consisting of amino, hydroxyl, halogen, nitro, cyano, mercapto, $C_1$-$C_4$-carboxyl, carbonamide, aminosulfonyl, $C_1$-$C_4$-alkyl, $C_3$-$C_4$-cycloalkyl, $C_2$-$C_4$-alkenyl, $C_5$-$C_6$-cycloalkenyl, $C_2$-$C_4$-alkynyl, N-mono-$C_1$-$C_4$-alkylamino, N,N-di-$C_1$-$C_4$-alkylamino, N—$C_1$-$C_4$-alkanoylamino, $C_1$-$C_4$-alkoxy, $C_2$-$C_4$-alkenyloxy, $C_2$-$C_4$-alkynyloxy, $C_3$-$C_4$-cycloalkoxy, $C_5$-$C_6$-cycloalkenyloxy, $C_1$-$C_4$-alkoxycarbonyl, $C_2$-$C_4$-alkenyloxycarbonyl, $C_2$-$C_4$-alkynyloxycarbonyl, $C_6$-,$C_{10}$-,$C_{14}$-aryloxycarbonyl, $C_1$-$C_4$-alkanoyl, $C_2$-$C_4$-alkenylcarbonyl, $C_2$-$C_4$-alkynylcarbonyl, $C_6$-,$C_{10}$-,$C_{14}$-arylcarbonyl, $C_1$-$C_4$-alkylsulfanyl, $C_3$-$C_4$-cycloalkylsulfanyl, $C_1$-$C_4$-alkylthio, $C_2$-$C_4$-alkenylthio, $C_5$-$C_6$-cycloalkenylthio, $C_2$-$C_4$-alkynylthio, $C_1$-$C_4$-alkylsulfenyl and $C_1$-$C_4$-alkylsulfinyl, wherein both enantiomers of the $C_1$-$C_4$-alkylsulfinyl group are included, $C_1$-$C_4$-alkylsulfonyl, N-mono-$C_1$-$C_4$-alkylaminosulfonyl, N,N-di-$C_1$-$C_4$-alkylaminosulfonyl, $C_1$-$C_4$-alkylphosphinyl, $C_1$-$C_4$-alkylphosphonyl, wherein both enantiomers are included for $C_1$-$C_4$-alkylphosphinyl or $C_1$-$C_4$-alkylphosphonyl, N—$C_1$-$C_4$-alkylaminocarbonyl, N,N-di-$C_1$-$C_4$-alkylaminocarbonyl, N—$C_1$-$C_4$-alkanoylaminocarbonyl, N—$C_1$-$C_4$-alkanoyl-N—$C_1$-$C_4$-alkylaminocarbonyl, $C_6$-,$C_{10}$-,$C_{14}$-aryl, $C_6$-,$C_{10}$-,$C_{14}$-aryloxy, benzyloxy, benzylthio, $C_6$-,$C_{10}$-,$C_{14}$-arylthio, $C_6$-,$C_{10}$-,$C_{14}$-arylamino, benzylamino, heterocyclyl and trialkylsilyl;

the moieties $A_1$, $A_2$ and $A_3$ are each independently N, O, $CR^3$, S or N—$R^4$, wherein $A_1$, $A_2$, $A_3$, Z and the carbon atom of the ring form an aromatic system;

R³ is each independently H, Cl, F, I, Br or optionally halogenated C₁-C₄-alkyl;

R⁴ is each independently H or optionally halogenated C₁-C₄-alkyl;

Q is O or S;

Z is C or N;

B₁, B₂, B₄, and B₅ are each independently C—R⁵ and wherein

R⁵ is each independently H, halogen, cyano, nitro, SF₅, C₁-C₆-alkyl, C₃-C₆-cycloalkyl, C₁-C₆-alkoxy, N—C₁-C₆-alkoxyimino-C₁-C₃-alkyl, C₁-C₆-alkylsulfanyl, C₁-C₆-alkylsulfinyl, C₁-C₆-alkylsulfonyl, N—C₁-C₆-alkylamino or N,N-di-C₁-C₆-alkylamino, in each case optionally substituted by one or more substituents selected from the group consisting of amino, hydroxyl, halogen, nitro, cyano, isocyano, mercapto, isothiocyanato, C₁-C₄-carboxyl, carbonamide, SF₅, aminosulfonyl, C₁-C₄-alkyl, C₃-C₄-cycloalkyl, C₂-C₄-alkenyl, C₅-C₆-cycloalkenyl, C₂-C₄-alkynyl, N-mono-C₁-C₄-alkylamino, N,N-di-C₁-C₄-alkylamino, N—C₁-C₄-alkanoylamino, C₁-C₄-alkoxy, C₂-C₄-alkenyloxy, C₂-C₄-alkynyloxy, C₃-C₄-cycloalkoxy, C₅-C₆-cycloalkenyloxy, C₁-C₄-alkoxycarbonyl, C₂-C₄-alkenyloxycarbonyl, C₂-C₄-alkynyloxycarbonyl, C₆-, C₁₀-, C₁₄-aryloxycarbonyl, C₁-C₄-alkanoyl, C₂-C₄-alkenylcarbonyl, C₂-C₄-alkynylcarbonyl, C₆-, C₁₀-, C₁₄-arylcarbonyl, C₁-C₄-alkylsulfanyl, C₃-C₄-cycloalkylsulfanyl, C₁-C₄-alkylthio, C₂-C₄-alkenylthio, C₅-C₆-cycloalkenylthio, C₂-C₄-alkynylthio, C₁-C₄-alkylsulfenyl and C₁-C₄-alkylsulfinyl, wherein both enantiomers of the C₁-C₄-alkylsulfinyl group are included, C₁-C₄-alkylsulfonyl, N-mono-C₁-C₄-alkylaminosulfonyl, N,N-di-C₁-C₄-alkylaminosulfonyl, C₁-C₄-alkylphosphinyl, C₁-C₄-alkylphosphonyl, wherein both enantiomers are included for C₁-C₄-alkylphosphinyl or C₁-C₄-alkylphosphonyl, N—C₁-C₄-alkylaminocarbonyl, N,N-di-C₁-C₄-alkylaminocarbonyl, N—C₁-C₄-alkanoylaminocarbonyl, N—C₁-C₄-alkanoyl-N—C₁-C₄-alkylaminocarbonyl, C₆-, C₁₀-, C₁₄-aryl, C₆-, C₁₀-, C₁₄-aryloxy, benzyl, benzyloxy, benzylthio, C₆-, C₁₀-, C₁₄-arylthio, C₆-, C₁₀-, C₁₄-arylamino, benzylamino, heterocyclyl and trialkylsilyl;

B₃ is CR⁵, wherein R⁵ is perhalogenated C₁-C₄-alkyl;

T is one of the following listed 5-membered heteroaromatics T1-T4 and T6, wherein the bond to

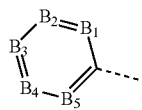

is marked with a hash #,

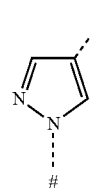

T1

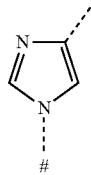

T2

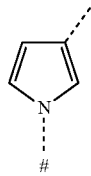

T3

T4

T6 and/or a salt, N-oxide and/or tautomeric form of a compound of formula (I).

2. The compound as claimed in claim 1, wherein R² is H or methyl.

3. The compound as claimed in claim 1, wherein T is T1, T2 or T4.

4. The compound as claimed in claim 1, wherein R¹ is benzyl, cyclopropyl or 1-CN-cyclopropyl.

5. The compound as claimed in claim 1, wherein the compound is a compound according to one of formulae of formula (Ia), (Ib), (1j), or (1k)

(Ia)

(Ib)

-continued (1j)
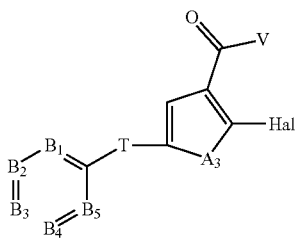

(1k)
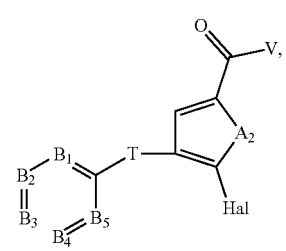

wherein V is N(R¹R²).

6. The compound as claimed in claim 1, wherein the compound is a compound of formula (I'a)

(I'a)
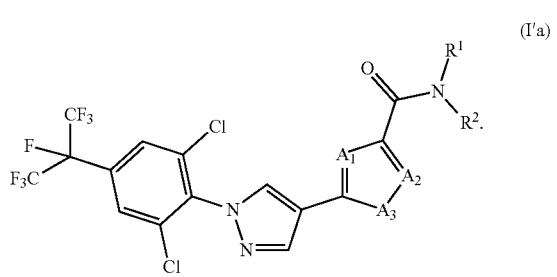

7. The compound as claimed in claim 1, wherein the compound is a compound of formula (I'b)

(I'b)
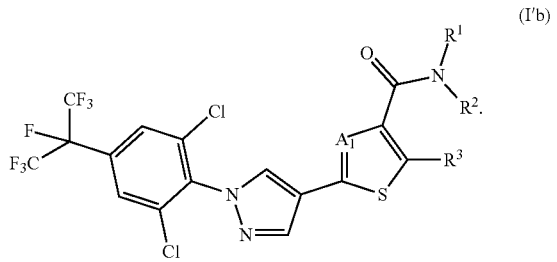

8. The compound as claimed in claim 1, wherein the compound is a compound of formula (I'c)

(I'c)
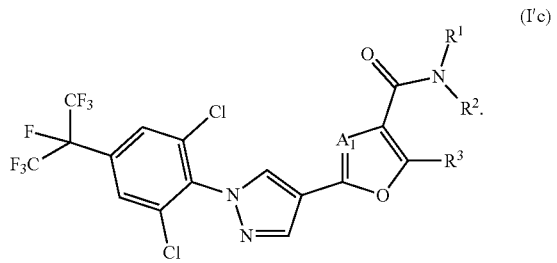

9. The compound as claimed in claim 1, wherein the compound is a compound of formula (I'd)

(I'd)
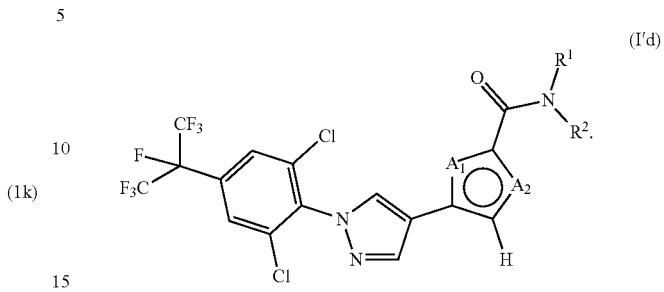

10. The compounds as claimed in claim 1, wherein $B_2$ and $B_4$ are in each case C—H.

11. The compound as claimed in claim 1, wherein $R^5$ of $B_3$ is perfluorinated $C_1$-$C_4$-alkyl.

12. An insecticidal composition comprising at least one compound as claimed in claim 1 and an extender and/or a surface-active substance.

13. A method for protecting transgenic or conventional seed and/or a plant that arises therefrom from infestation by one or more pests, comprising treating the seed with at least one compound as claimed in claim 1.

14. A product comprising a compound as claimed in claim 1.

15. A seed in which a compound as claimed in claim 1 has been applied to the seed as a constituent of a coating or as a further layer or further layers in addition to a coating.

16. The compound as claimed in claim 1, wherein $R^1$ is $C_3$-$C_7$-cycloalkyl optionally substituted by halogen or cyano, or $C_6$-,$C_{10}$-,$C_{14}$-aryl($C_1$-$C_3$)-alkyl, wherein $C_6$-,$C_{10}$-,$C_{14}$-Aryl may optionally be substituted mutually independently by one or more substituents selected from the group consisting of amino, hydroxyl, halogen, nitro, cyano, isocyano, mercapto and $C_1$-$C_4$-alkyl, or $C_1$-$C_6$-alkylcarbonyl;

the moieties $A_1$, $A_2$ and $A_3$ are each independently N, CR³, S or N—R⁴, wherein $A_1$, $A_2$, $A_3$, Z and the carbon atom of the ring form an aromatic system;

$R^3$ is each independently H, Cl, F, I, Br or optionally halogenated methyl;

$R^4$ is each independently H or optionally halogenated methyl;

Q is O;

Z is C.

17. The compound as claimed in claim 1, wherein $R^1$ is $C_3$-cycloalkyl optionally substituted by cyano or $C_6$-aryl($C_1$-$C_3$)-alkyl.

18. The compound as claimed claim 1, wherein T is T1.

19. A product comprising an insecticidal composition as claimed in claim 12.

* * * * *